US012357799B2

(12) United States Patent
Kapur et al.

(10) Patent No.: US 12,357,799 B2
(45) Date of Patent: Jul. 15, 2025

(54) SYSTEMS AND METHODS FOR SELECTIVELY OCCLUDING THE SUPERIOR VENA CAVA FOR TREATING HEART CONDITIONS

(71) Applicant: Tufts Medical Center, Inc., Boston, MA (US)

(72) Inventors: Navin K. Kapur, Hanover, MA (US); Richard Karas, Franklin, MA (US)

(73) Assignee: Tufts Medical Center, Inc., Boston, MA (US)

( * ) Notice: Subject to any disclaimer, the term of this patent is extended or adjusted under 35 U.S.C. 154(b) by 265 days.

(21) Appl. No.: 18/170,456

(22) Filed: Feb. 16, 2023

(65) Prior Publication Data
US 2023/0241361 A1    Aug. 3, 2023

Related U.S. Application Data

(63) Continuation of application No. 17/100,680, filed on Nov. 20, 2020, now Pat. No. 11,612,725, which is a
(Continued)

(51) Int. Cl.
*A61B 5/02* (2006.01)
*A61B 5/00* (2006.01)
(Continued)

(52) U.S. Cl.
CPC ... *A61M 25/10184* (2013.11); *A61B 5/02028* (2013.01); *A61B 5/02152* (2013.01);
(Continued)

(58) Field of Classification Search
CPC ......... A61B 5/0215; A61B 5/026; A61B 5/02; A61B 5/02028; A61B 5/0205;
(Continued)

(56) References Cited

U.S. PATENT DOCUMENTS 4,546,759 A   10/1985 Solar
4,576,181 A    3/1986 Wallace et al.
(Continued)

FOREIGN PATENT DOCUMENTS

CN   1819855 A    8/2006
EP   2353501 A1   8/2011
(Continued)

OTHER PUBLICATIONS

Atherton, et al., Diastolic Ventricular Interaction In Chronic Heart Failure, Lancet, 349(9067):1720-1724 (1997).
(Continued)

*Primary Examiner* — Deanna K Hall
(74) *Attorney, Agent, or Firm* — Greenberg Traurig, LLP; Christopher C. Bolten; Albert K. Heng

(57) ABSTRACT

Systems and methods and devices are provided for treating conditions such as heart failure and/or pulmonary hypertension by at least partially occluding flow through the superior vena cava for an interval spanning multiple cardiac cycles. A catheter with an occlusion device is provided along with a controller that actuates a drive mechanism to provide at least partial occlusion of the patient's superior vena cava, which reduces cardiac filling pressures, and induces a favorable shift in the patient's Frank-Starling curve towards healthy heart functionality and improved cardiac performance. The occlusion device may include a lumen obstructed by a relief valve that may permit fluid flow through the occlusion device to release an excessive buildup of pressure.

25 Claims, 47 Drawing Sheets

Related U.S. Application Data continuation of application No. 16/168,357, filed on Oct. 23, 2018, now Pat. No. 10,842,974, which is a continuation-in-part of application No. 15/753,300, filed as application No. PCT/US2016/047055 on Aug. 15, 2016, now Pat. No. 10,758,715, which is a continuation-in-part of application No. 15/203,437, filed on Jul. 6, 2016, now Pat. No. 10,279,152, which is a continuation of application No. 14/828,429, filed on Aug. 17, 2015, now Pat. No. 9,393,384.

(60) Provisional application No. 62/642,569, filed on Mar. 13, 2018, provisional application No. 62/576,529, filed on Oct. 24, 2017.

(51) Int. Cl.
| | |
|---|---|
| *A61B 5/0215* | (2006.01) |
| *A61B 5/024* | (2006.01) |
| *A61B 5/026* | (2006.01) |
| *A61B 5/027* | (2006.01) |
| *A61B 17/12* | (2006.01) |
| *A61B 17/132* | (2006.01) |
| *A61B 17/135* | (2006.01) |
| *A61M 25/10* | (2013.01) |
| *A61B 17/00* | (2006.01) |
| *A61B 90/00* | (2016.01) |

(52) U.S. Cl.
CPC .......... *A61B 5/02444* (2013.01); *A61B 5/026* (2013.01); *A61B 5/027* (2013.01); *A61B 5/6853* (2013.01); *A61B 17/12036* (2013.01); *A61B 17/1204* (2013.01); *A61B 17/12109* (2013.01); *A61B 17/12136* (2013.01); *A61B 17/12172* (2013.01); *A61B 17/1322* (2013.01); *A61B 17/1355* (2013.01); *A61B 2017/00022* (2013.01); *A61B 2017/00044* (2013.01); *A61B 2017/00221* (2013.01); *A61B 2017/00398* (2013.01); *A61B 2017/00734* (2013.01); *A61B 2017/00889* (2013.01); *A61B 2090/065* (2016.02); *A61B 2562/0247* (2013.01); *A61M 2025/1052* (2013.01); *A61M 2205/3331* (2013.01); *A61M 2230/005* (2013.01); *A61M 2230/30* (2013.01)

(58) Field of Classification Search
CPC ............ A61B 5/02152; A61B 5/02156; A61B 5/02158; A61B 17/12; A61B 17/1204; A61B 17/12036; A61B 17/12109; A61B 17/12136; A61M 1/125; A61M 2025/1052; A61M 2205/3331; A61M 2230/005; A61M 2230/30; A61M 25/10184
See application file for complete search history.

(56) References Cited

U.S. PATENT DOCUMENTS

| | | |
|---|---|---|
| 4,610,256 A | 9/1986 | Wallace |
| 4,846,787 A | 7/1989 | Aall-Flood et al. |
| 4,949,723 A | 8/1990 | Wallace et al. |
| 5,021,046 A | 6/1991 | Wallace |
| 5,097,840 A | 3/1992 | Wallace et al. |
| 5,330,451 A | 7/1994 | Gabbay |
| 5,458,574 A | 10/1995 | Machold et al. |
| 6,146,354 A | 11/2000 | Beil |
| 6,485,500 B1 | 11/2002 | Kokish et al. |
| 6,726,651 B1 | 4/2004 | Robinson et al. |
| 6,790,043 B2 | 9/2004 | Aboud |
| 6,843,779 B1 | 1/2005 | Andrysiak et al. |
| 7,476,200 B2 | 1/2009 | Tal |
| 7,896,840 B2 | 3/2011 | Spencer et al. |
| 7,909,794 B2 | 3/2011 | Briscoe et al. |
| 7,909,844 B2 | 3/2011 | Alkhatib et al. |
| 7,914,643 B2 | 3/2011 | Simpson |
| 7,951,259 B2 | 5/2011 | Duchamp et al. |
| 7,959,667 B2 | 6/2011 | Ta et al. |
| 7,967,781 B2 | 6/2011 | Simpson et al. |
| 7,972,299 B2 | 7/2011 | Carter et al. |
| 8,449,565 B2 | 5/2013 | Duhay |
| 8,646,325 B2 | 2/2014 | Hoem et al. |
| 8,679,052 B2 | 3/2014 | Bellantone |
| 8,876,850 B1 | 11/2014 | Vollmers et al. |
| 8,968,239 B2 | 3/2015 | Herrera |
| 9,393,384 B1 | 7/2016 | Kapur et al. |
| 9,878,080 B2 | 1/2018 | Kaiser et al. |
| 9,901,722 B2 | 2/2018 | Nitzan et al. |
| 10,279,152 B2 | 5/2019 | Kapur et al. |
| 10,639,460 B2 | 5/2020 | Nitzan et al. |
| 10,653,871 B2 | 5/2020 | Nitzan et al. |
| 10,758,715 B2 | 9/2020 | Kapur et al. |
| 10,842,974 B2 | 11/2020 | Kapur et al. |
| 10,926,069 B2 | 2/2021 | Nitzan et al. |
| 11,872,361 B2 | 1/2024 | Kapur et al. |
| 2003/0186203 A1 | 10/2003 | Aboud |
| 2004/0022640 A1 | 2/2004 | Siess et al. |
| 2004/0064090 A1 | 4/2004 | Keren et al. |
| 2004/0167376 A1 | 8/2004 | Peters et al. |
| 2005/0015048 A1 | 1/2005 | Chiu et al. |
| 2006/0064059 A1 | 3/2006 | Gelfand et al. |
| 2006/0206029 A1 | 9/2006 | Yair |
| 2008/0294070 A1 | 11/2008 | Kinori |
| 2009/0131785 A1 | 5/2009 | Lee et al. |
| 2010/0318114 A1 | 12/2010 | Pranevicius et al. |
| 2010/0331876 A1 | 12/2010 | Cedeno |
| 2011/0202084 A1 | 8/2011 | Hoem et al. |
| 2011/0282274 A1 | 11/2011 | Fulton, III |
| 2011/0295177 A1 | 12/2011 | Mohl |
| 2011/0295302 A1 | 12/2011 | Mohl |
| 2012/0029466 A1 | 2/2012 | Callaghan et al. |
| 2013/0023909 A1 | 1/2013 | Duhay |
| 2015/0201944 A1 | 7/2015 | Starnes |
| 2015/0223707 A1 | 8/2015 | Ludoph |
| 2017/0049946 A1 | 2/2017 | Kapur et al. |
| 2018/0000488 A1 | 1/2018 | Hu et al. |
| 2018/0243541 A1 | 8/2018 | Kapur et al. |
| 2019/0070348 A1 | 3/2019 | Frost |
| 2019/0126014 A1 | 5/2019 | Kapur et al. |
| 2019/0255302 A1 | 8/2019 | Kapur et al. |
| 2020/0038566 A1 | 2/2020 | Johnson et al. |
| 2021/0077792 A1 | 3/2021 | Kapur et al. |
| 2022/0104828 A1 | 4/2022 | Keating et al. |

FOREIGN PATENT DOCUMENTS

| | | |
|---|---|---|
| EP | 2353503 A1 | 8/2011 |
| WO | WO-9300037 A1 | 1/1993 |
| WO | WO-2004073796 A2 | 9/2004 |
| WO | WO-2013061281 A1 | 5/2013 |
| WO | WO-2015009028 A1 | 1/2015 |
| WO | WO-2015109028 A1 | 7/2015 |
| WO | WO-2017031068 A1 | 2/2017 |
| WO | WO-2017081561 A1 | 5/2017 |
| WO | WO-2019083989 A1 | 5/2019 |
| WO | WO-2019140073 A1 | 7/2019 |
| WO | WO-2020061143 A1 | 3/2020 |
| WO | WO-2020097428 A1 | 5/2020 |

OTHER PUBLICATIONS

Bannon, et al., Anatomic Considerations for Central Venous Cannulation, 4 Risk Management and Healthcare Policy, 4:27-39 (2011).

Bilecen, et al., MR Angiography With Venous Compression, Radiology, 233(2):617-619 (Nov. 2004).

Delis, et al., Effect of Posture on Popliteal Artery Hemodynamics, 135(3):265-269 (Mar. 2000).

Difference Between Superior and Inferior Vena Cava, Pediaa (Aug.

(56) References Cited

OTHER PUBLICATIONS 28, 2018), https://pediaa.com/difference-between-superior-and-inferior-vena-cava/.

Extended EP Search Report dated Oct. 20, 2021 in EP Patent Application Serial No. 21177661.2.

Hansen, et al., Veno-occlusive unloading of the heart reduces infarct size in experimental ischemia-reperfusion, *Scientific Reports*, 11(1):1-9 (Feb. 2021).

Herrera, et al., First Percutaneous Transluminal Caval Flow Restriction in a Patient With Congestive Heart Failure, Abstract No. TCT-428, New Devices and Innovation, www.jacctctabstracts 2014.com, vol. 64/11/Suppl B, Sep. 13-17, 2014.

International Search Report & Written Opinion dated Jan. 28, 2019 in Int'l PCT Patent Appl. Serial No. PCT/US2018/057085.

International Search Report & Written Opinion dated Feb. 18, 2021 in Int'l PCT Patent Appl. Serial No. PCT/US2020/061386.

International Search Report & Written Opinion dated Oct. 18, 2016 in Int'l PCT Patent Application Serial No. PCT/US2016/047055.

Ishiguchi, et al., Endovascular Stent-Graft Deployment: Temporary Vena Caval Occlusion with Balloons to Control Aortic Blood Flow-Experimental Canine Study and Initial Clinical Experience, Radiology, 215:(2):594-599 (2000).

Kaiser, et al., First-in-Human Experience of Mechanical Preload Control in Patients With HFpEF During Exercise, *J. Am. Coll. Cardiol. Basic Trans. Science*, pp. 1-10 (2021), https://doi.org/10.1016/j.jacbts.2020.12.007.

Kappagoda, et al., Effect of Stimulating Right Atrial Receptors On Urine Floe In The Dog, J. Physiol, 235:493-502 (1973).

Kapur, et al., First-in-human experience with occlusion of the superior vena cava to reduce cardiac filling pressures in congestive heart failure, Catheter Cardiovasc. Interv., 93:1205-1210 (2019).

Kapur, et al., Intermittent Occlusion of the Superior Vena Cava Reduces Cardiac Filling Pressures in Preclinical Models of Heart Failure, Journal of Cardiovascular Translational Research, published on: Nov. 26, 2019, https://doi.org/1 0.1 007/s12265-019-09916-y.

Kass, et al., Use of a conductance (volume) catheter and transient inferior vena caval occlusion for rapid determination of pressure-volume relationships in man, Cathet. Cardiovasc. Diagn., 15(3):192-202 (1988).

Lee et al., Partial right atrial inflow occlusion for controlled systemic hypotension during thoracic endovascular aortic repair, *J. Vasc. Surg.*, 48(2):494-498 (2008).

Low, Phillip A., "Venoarteriolar Reflex," Primer On The Autonomic Nervous System, Second Edition, Chapter 38, pp. 152-153 (2004).

Mehta, M.D., Manish, Compliant Occlusion Balloons—Use of complaint occlusion balloons during EVAR for AAA rupture, insert to *Endovascular Today*, pp. 29-31 (Nov. 2008).

Mork, et al., Impaired Neurogenic Control of Skin Perfusion In Erythromelalgia, Journal of Investigative Dermatology, 118(4):699-703 (Apr. 2002).

Moscucci, M., Grossman & Baim's Cardiac Catheterization, Angiography, and Intervention, 8th Edition, 2014.

Rachapalli, et al., Superior Vena Cava Syndrome: Role of the Interventionalist, Canadian Association of Radiologists Journal, 65:168-176 (2014).

Rodrigues, et al., Effect of baroreceptor denervation on the autonomic control of arterial pressure in conscious mice, *Exp. Physiol.*, 96(9):853-862 (2011).

Rosenblum, et al., Conceptual Considerations For Device-Based Therapy in Acute Decompensated Heart Failure, *Circulation: Heart Failure*, 13(4):e006731 (Apr. 2020).

Ross, et al., Studies on Starling's Law of the Heart, IX. The Effects of Impeding Venous Return on Performance of the Normal and Failing Human Left Ventricle, *Circulation*, 30:719-727 (1964).

Shimizu, et al., Embolization of a Fractured Central Venous Catheter Placed Using The Internal Jugular Approach, International Journal of Surgery Case Reports, 5(5):219-221 (Jan. 2014).

Swan, et al., Catheterization Of The Heart In Man With Use Of A Flow-Directed Balloon-Tipped Catheter, New England Journal of Medicine, 283(9):447-451 (Aug. 1970).

Tucker, et al., Anatomy, Abdomen and Pelvis, Inferior Vena Cava, Jul. 27, 2021, available at https://www.ncbi.nlm.nih.gov/books/NBK482353/.

Tzifa, et al., Endovascular Treatment for Superior Vena Cava Occlusion or Obstruction in a Pediatric and Young Adult Population, A 22-Year Experience, Journal of the American College of Cardiology, 49(9):1003-1009 (2007).

Van Fossen, et al., Safety and efficacy of inferior vena caval occlusion to rapidly alter ventricular loading conditions in idiopathic dilated cardiomyopathy, The American Journal of Cardiology, 59(9):937-942 (1987).

Yancy, et al., 2013 ACCF/AHA Guideline for the Management of Heart Failure-A Report of the American College of Cardiology Foundation/American Heart Association Task Force on Practice Guidelines, Circulation, 128:e240-e327 (2013).

International Search Report & Written Opinion dated Aug. 23, 2023 in Int'l PCT Patent Appl. Serial No. PCT/US2023/024440.

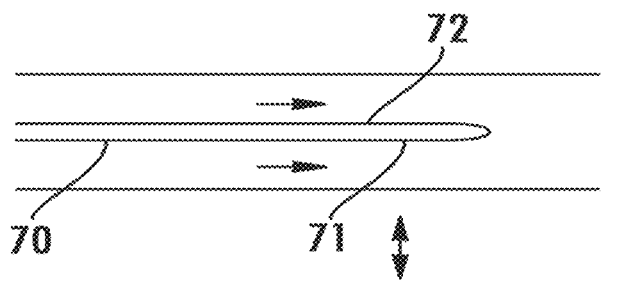
FIG. 8A
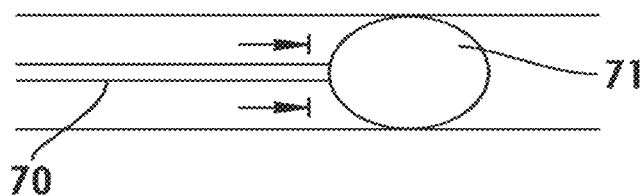
FIG. 8B
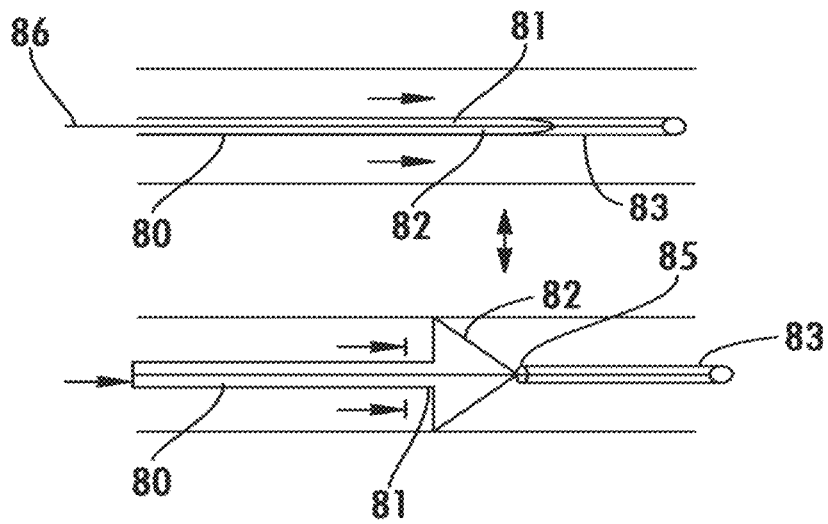
FIG. 9A
FIG. 9B
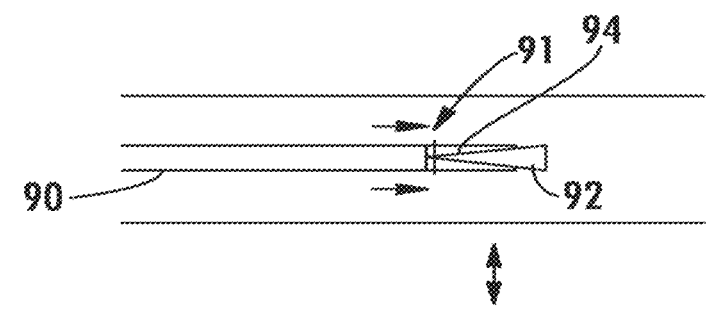
FIG. 10A
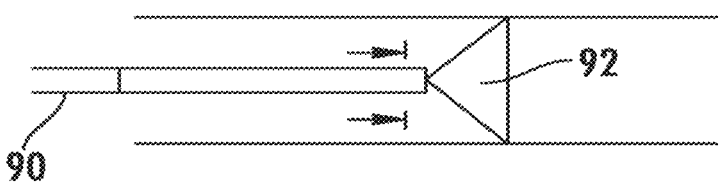
FIG. 10B

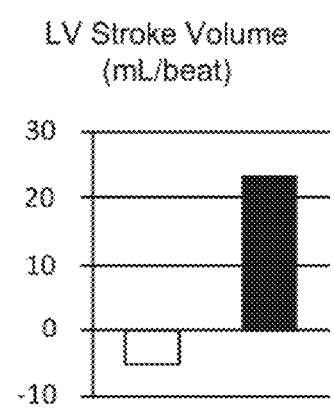
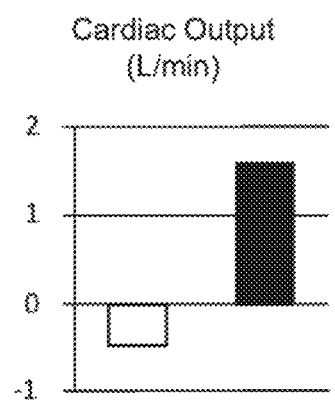
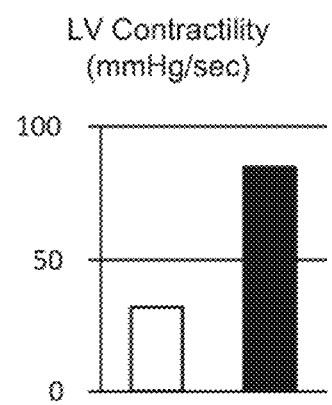
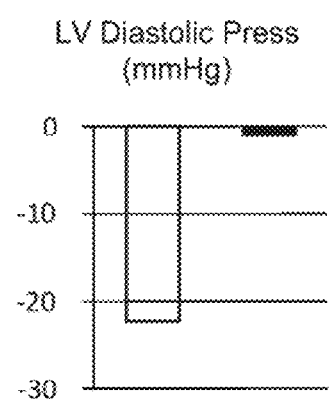
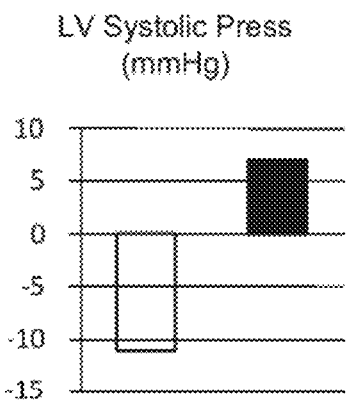
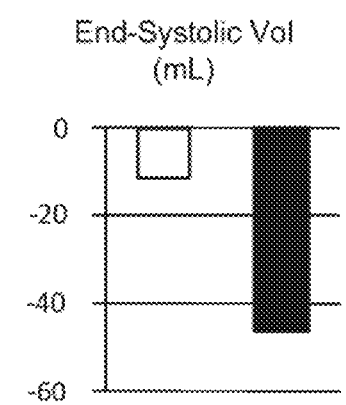
FIG. 15

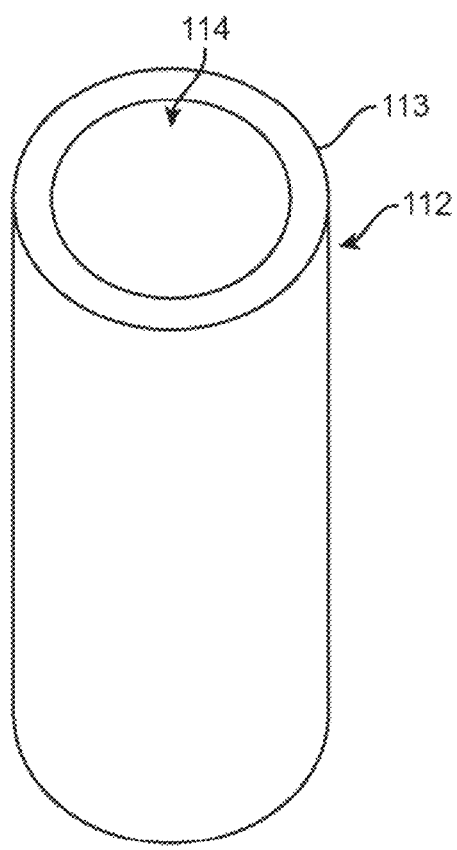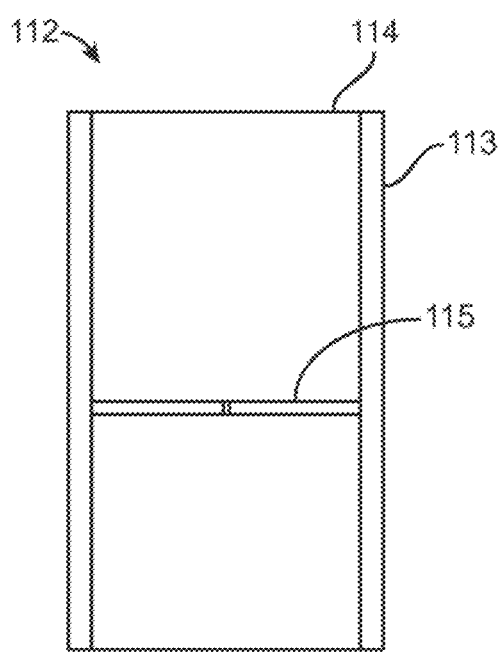
FIG. 32
FIG. 33

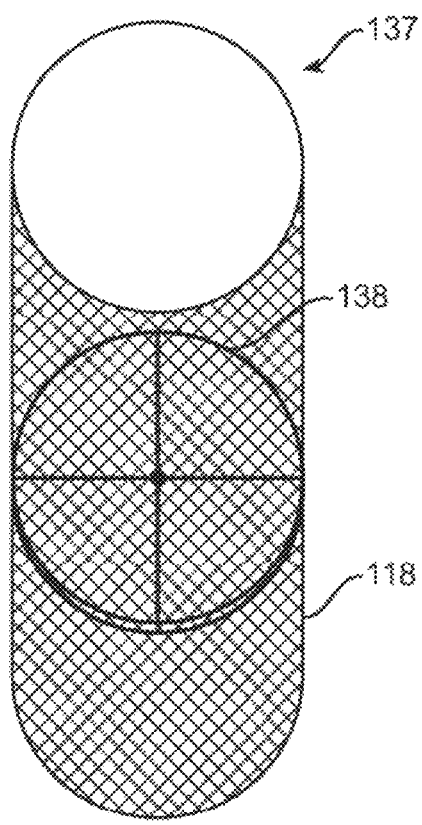 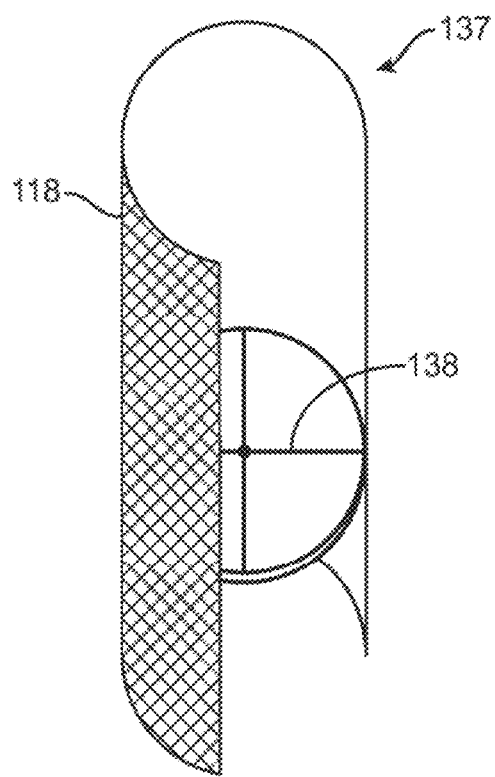
FIG. 40A                    FIG. 40B

SYSTEMS AND METHODS FOR SELECTIVELY OCCLUDING THE SUPERIOR VENA CAVA FOR TREATING HEART CONDITIONS

CROSS-REFERENCE TO RELATED APPLICATIONS

This application is a continuation of U.S. patent application Ser. No. 17/100,680, filed Nov. 20, 2020, which is a continuation of U.S. patent application Ser. No. 16/168,357, filed Oct. 23, 2018, now U.S. Pat. No. 10,842,974, which claims priority to U.S. Provisional Application Ser. No. 62/642,569, filed Mar. 13, 2018, and U.S. Provisional Application Ser. No. 62/576,529, filed Oct. 24, 2017, and which is also a continuation-in-part of U.S. patent application Ser. No. 15/753,300, filed Feb. 17, 2018, now U.S. Pat. No. 10,758,715, which is a national stage application of PCT/US2016/047055, filed Aug. 15, 2016, which is a continuation-in-part of U.S. patent application Ser. No. 15/203,437, filed Jul. 6, 2016, now U.S. Pat. No. 10,279,152, which is a continuation of U.S. patent application Ser. No. 14/828,429, filed Aug. 17, 2015, now U.S. Pat. No. 9,393,384, the entire contents of each of which are incorporated herein by reference.

FIELD OF THE INVENTION

The disclosure relates to methods and systems for improving cardiac function in patients suffering from heart failure, including patients with reduced ejection fraction, and for treating pulmonary hypertension and/or cardiorenal syndrome.

BACKGROUND OF THE INVENTION

Heart failure is a major cause of global mortality. Heart failure often results in multiple long-term hospital admissions, especially in the later phases of the disease. Absent heart transplantation, the long term prognosis for such patients is bleak, and pharmaceutical approaches are palliative only. Consequently, there are few effective treatments to slow or reverse the progression of this disease.

Heart failure can result from any of multiple initiating events. Heart failure may occur as a consequence of ischemic heart disease, hypertension, valvular heart disease, infection, inherited cardiomyopathy, pulmonary hypertension, or under conditions of metabolic stress including pregnancy. Heart failure also may occur without a clear cause—also known as idiopathic cardiomyopathy. The term heart failure encompasses left ventricular, right ventricular, or biventricular failure.

While the heart can often initially respond successfully to the increased workload that results from high blood pressure or loss of contractile tissue, over time this stress induces compensatory cardiomyocyte hypertrophy and remodeling of the ventricular wall. In particular, over the next several months after the initial cardiac injury, the damaged portion of the heart typically will begin to remodel as the heart struggles to continue to pump blood with reduced muscle mass or less contractility. This in turn often leads to overworking of the myocardium, such that the cardiac muscle in the compromised region becomes progressively thinner, enlarged and further overloaded. Simultaneously, the ejection fraction of the damaged ventricle drops, leading to lower cardiac output and higher average pressures and volumes in the chamber throughout the cardiac cycle, the hallmarks of heart failure. Not surprisingly, once a patient's heart enters this progressively self-perpetuating downward spiral, the patient's quality of life is severely affected and the risk of morbidity skyrockets. Depending upon a number of factors, including the patient's prior physical condition, age, sex and lifestyle, the patient may experience one or several hospital admissions, at considerable cost to the patient and social healthcare systems, until the patient dies either of cardiac arrest or any of a number of co-morbidities including stroke, kidney failure, liver failure, or pulmonary hypertension.

Currently, there are no device-based solutions that specifically target a reduction in preload to limit the progression of heart failure. Pharmaceutical approaches are available as palliatives to reduce the symptoms of heart failure, but there exists no pharmaceutical path to arresting or reversing heart failure. Moreover, the existing pharmaceutical approaches are systemic in nature and do not address the localized effects of remodeling on the cardiac structure. It therefore would be desirable to provide systems and methods for treating heart failure that can arrest, and more preferably, reverse cardiac remodeling that result in the cascade of effects associated with this disease.

Applicants note that the prior art includes several attempts to address heart failure. Prior to applicants' invention as described herein, there are no effective commercial devices available to treat this disease. Described below are several known examples of previously known systems and methods for treating various aspects of heart failure, but none appear either intended to, or capable of, reducing left ventricular end diastolic volume ("LVEDV"), left ventricular end diastolic pressure ("LVEDP"), right ventricular end diastolic volume ("RVEDV"), or right ventricular end diastolic pressure ("RVEDP") without causing possibly severe side-effects.

For example, U.S. Pat. No. 4,546,759 to Solar describes a triple balloon catheter designed for placement such that a distal balloon intermittently occludes the superior vena cava, a proximal balloon intermittently occludes the inferior vena cava, and an intermediate balloon expands synchronously with occurrence of systole of the right ventricle, thereby enhancing ejection of blood from the right ventricle. The patent describes that the system is inflated and deflated in synchrony with the normal heart rhythm, and is designed to reduce the load on the right ventricle to permit healing of injury or defect of the right ventricle. It does not describe or suggest that the proposed regulation of flow into and out of the right ventricle will have an effect on either LVEDV or LVEDP, nor that it could be used to arrest or reverse acute/chronic heart failure.

U.S. Patent Publication No. US 2006/0064059 to Gelfand describes a system and method intended to reduce cardiac infarct size and/or myocardial remodeling after an acute myocardial infarction by reducing the stress in the cardiac walls. The system described in the patent includes a catheter having a proximal portion with an occlusion balloon configured for placement in the inferior vena cava and a distal portion configured for placement through the tricuspid and pulmonary valves into the pulmonary artery. The patent application describes that by partially occluding the inferior vena cava, the system regulates the amount of blood entering the ventricles, and consequently, reduces the load on the ventricles, permitting faster healing and reducing the expansion of the myocardial infarct. The system described in Gelfand includes sensors mounted on the catheter that are read by a controller to adjust regulation of the blood flow entering the heart, and other measured parameters, to within predetermined limits. The patent application does not describe or suggest that the system could be used to treat, arrest or reverse congestive heart failure once the heart has already undergone the extensive remodeling typically observed during patient re-admissions to address the symptoms of congestive heart failure.

U.S. Patent Publication No. US 2010/0331876 to Cedeno describes a system and method intended to treat congestive heart failure, similar in design to described in Gelfand, by regulating the return of venous blood through the inferior vena cava. The system described in Cedeno describes that a fixed volume balloon disposed in the inferior vena cava will limit blood flow in the inferior vena cava (IVC). The degree of occlusion varies as the vessel expands and contracts during inspiration and expiration, to normalize venous blood return. The patent application further describes that the symptoms of heart failure improve within three months of use of the claimed system. Although the system and methods described in Cedeno appear promising, there are a number of potential drawbacks to such a system that applicants' have discovered during their own research. Applicants have observed during their own research that fully occluding the inferior vena cava not only reduces left ventricular volume, but significantly reduces left ventricular systolic pressure, leading to reduced systemic blood pressure and cardiac output. Moreover, full inferior vena cava occlusion may increase venous congestion within the renal, hepatic, and mesenteric veins; venous congestion is a major cause of renal failure in congestive heart failure patients.

There are several major limitations to approaches that involve partial or full occlusion of the IVC to modulate cardiac filling pressures and improve cardiac function. First, the IVC has to be reached via the femoral vein or via the internal jugular vein. If approached via the femoral vein, then the patient will be required to remain supine and will be unable to ambulate. If approached via the jugular or subclavian veins, the apparatus would have to traverse the superior vena cava and right atrium, thereby requiring cardiac penetration, which predisposes to potential risk involving right atrial injury, induction of arrhythmias including supraventricular tachycardia or bradycardia due to heart block. Second, the IVC approach described by Cedeno and colleagues depends on several highly variable indices (especially in the setting of congestive heart failure): 1) IVC diameter, which is often dilated in patients with heart failure; b) intermittent (full or partial) IVC occlusion may cause harm by increasing renal vein pressure, which reduces glomerular filtration rates and worsens kidney dysfunction; c) dependence on the patient's ability to breathe, which is often severely impaired in HF (A classic breathing pattern in HF is known as Cheynes Stokes respiration, which is defined by intermittent periods of apnea where the IVC may collapse and the balloon will cause complete occlusion resulting in lower systemic blood pressure and higher renal vein pressure); d) if prolonged cardiac unloading is required to see a clinical improvement or beneficial changes in cardiac structure or function, then IVC occlusion will not be effective since sustained IVC occlusion will compromise blood pressure and kidney function. Third, the approach defined by Cedeno will require balloon customization depending on IVC size, which may be highly variable. Fourth, many patients with heart failure have IVC filters due to an increased propensity for deep venous thrombosis, which would preclude broad application of IVC therapy.

Pulmonary hypertension (PH) is also a major cause of morbidity and mortality worldwide. While heart failure is a common cause of pulmonary hypertension, as mentioned above, pulmonary hypertension may also be caused by primary lung disease. Today, pharmacologic treatments may reduce pulmonary artery systolic pressure (PASP) and improve symptoms and ultimately survival for patients with pulmonary hypertension. However, there are drawbacks to pharmacologic treatments such as costs and side effects.

In view of the foregoing drawbacks of the previously known systems and methods for regulating venous return to address heart failure, it would be desirable to provide systems and methods for treating acute and chronic heart failure that reduce the risk of exacerbating co-morbidities associated with the disease.

It further would be desirable to provide systems and methods for treating acute and chronic heart failure that arrest or reverse cardiac remodeling, and are practical for chronic and/or ambulatory use.

It still further would be desirable to provide systems and methods for treating heart failure that permit patients suffering from this disease to have improved quality of life, reducing the need for hospital admissions and the length of hospital stays, and the associated burden on societal healthcare networks.

It also would be desirable to provide systems and methods that permit treatment of pulmonary hypertension and cardiorenal syndrome.

SUMMARY OF THE INVENTION

In view of the drawbacks of the previously known systems and methods for treating heart failure, it would be desirable to provide systems and methods for treating acute and/or chronic heart failure that can arrest, and more preferably, reverse cardiac remodeling that result in the cascade of effects associated with this disease.

It further would be desirable to provide systems and methods for arresting or reversing cardiac remodeling in patients suffering from heart failure that are practical for ambulatory and/or chronic use.

It still further would be desirable to provide systems and methods for treating heart failure that reduce the risk of exacerbating co-morbidities associated with the disease, such as venous congestion resulting in renal and hepatic complications.

It also would be desirable to provide systems and methods for treating heart failure that permit patients suffering from this disease to have improved quality of life, while reducing the need for hospital re-admissions and the associated burden on societal healthcare networks.

It further would be desirable to provide systems and methods for treating pulmonary hypertension that permit patients suffering from this disease to have improved quality of life. In addition, it would be desirable to provide systems and methods for treating heart attacks, acute heart failure, chronic heart failure, heart failure with preserved ejection fraction, right heart failure, constrictive and restrictive cardiomyopathies, and cardio-renal syndromes (Types 1-5).

These and other advantages are provided by the present invention, which provides systems and methods for regulating venous blood return to the heart through the superior vena cava ("SVC"), over intervals spanning several cardiac cycles, to reduce ventricular overload, and to reduce cardiac preload and pulmonary artery pressure without increasing renal vein pressure. In accordance with the principles of the present invention, venous regulation via the SVC can be used to reduce LVEDP, LVEDV, RVEDP, and/or RVEDV, and to arrest or reverse ventricular myocardial remodeling. Counter-intuitively, applicants have observed in preliminary animal testing that intermittent partial occlusion of the SVC does not lead to stagnation of cerebral flow or observable adverse side effects. More importantly, applicants' preliminary animal testing reveals that occlusion of the SVC results in significant reduction in both RVEDP and LVEDP, while improving total cardiac output and without a significant reduction on left ventricular systolic pressure ("LVSP"). Accordingly, unlike the approach discussed in the foregoing published Cedeno patent application, the present invention provides a beneficial reduction in LVEDP, LVEDV, RVEDP, and/or RVEDV, with negligible impact on LVSP, but improved stroke volume (cardiac output), and reduced risk for venous congestion resulting in increased co-morbidities. The systems and methods described herein provide acute improvement in cardiac filling pressures and function to benefit patients at risk for acutely decompensated heart failure.

There are several major advantages to targeting SVC flow (instead of IVC flow). First, device placement in the SVC avoids use of the femoral veins and avoids cardiac penetration. This allows for development of a fully implantable, and even ambulatory, system for acute or chronic therapy. Second, SVC occlusion can be intermittent or prolonged depending on the magnitude of unloading required. Unlike IVC occlusion, prolonged SVC occlusion maintains systemic blood pressure and improves cardiac output. This allows for sustained unloading of both the right and left ventricle, which allows for both acute hemodynamic benefit and the potential for long term beneficial effects on cardiac structure or function. Third, unlike IVC occlusion, SVC occlusion does not depend on patient respiration. Fourth, by developing an internal regulator of SVC occlusion driven by mean right atrial pressure or the pressure differential across the occlusion balloon, the SVC device can be programmed and personalized for each patient's conditions. Fifth, by placing the device in the SVC, the device can be used in patients with existing IVC filters.

In accordance with another aspect of the present invention, partial or total intermittent occlusion of the SVC over multiple cardiac cycles is expected to permit the myocardium to heal, such that the reduced wall stress in the heart muscle arrests or reverses the remodeling that is symptomatic of the progression of heart failure. Without wishing to be bound by theory, applicants believe that intermittent occlusion of the SVC permits the heart, when implemented over a period of hours, days, weeks, or months, to transition from a Starling curve indicative of heart failure with reduced ejection fraction towards a Starling curve having LVEDP and LVEDP more indicative of normal cardiac function. Consequently, applicant's preliminary animal testing suggests that use of the inventive system over a period of hours, days, weeks, or months, e.g., 3-6 months, may not only arrest the downward spiral typical of the disease, but also may enable the heart to recover function sufficiently for the patient to terminate use of either the system of the present invention, pharmaceutical treatments, or both.

In accordance with another aspect of the disclosure, a system is provided that comprises a catheter having a flow limiting element configured for placement in or on the SVC, and a controller for controlling actuation of the flow limiting element. The controller is preferably programmed to receive an input indicative of fluctuations in the patient's hemodynamic state and to regulate actuation/deactivation of the flow limiting element responsive to that input. The fluctuations in the patient's hemodynamic state may result from the patient's ambulatory activity. The controller may be programmed at the time of implantation of the catheter to retain full or partial occlusion of the SVC over a predetermined number of heart cycles or predetermined time interval based on the patient's resting heart rate, and this preset number of cycles or time interval may be continually adjusted by the controller responsive to the patient's heart rate input. The controller may further receive signals from sensors and/or electrodes indicative of sensed parameters reflecting the hemodynamic state, e.g., blood flow rate, blood volume, pressure including cardiac filling pressure, and the controller may continually adjust the preset number of cycles or time interval responsive to the sensed parameter(s).

In one preferred embodiment, the catheter is configured to be implanted intravascularly (e.g., via the patient's left subclavian vein), so that the flow limiting element is disposed within the SVC just proximal of the right atrium. A proximal end of the catheter may be coated or impregnated with an antibacterial agent to enable prolonged use of the catheter with reduced risk of infection at the site where the catheter passes percutaneously. The controller preferably is battery-powered, and includes a quick-connect coupling that permits the actuation mechanism of the controller to operatively couple to the flow limiting element. In a preferred embodiment, the controller is sufficiently small such that it may be worn by the patient in a harness around the shoulder. In contrast to previously-known systems, which tether the patient to a bed or acute-care setting, the system of the present invention is configured so that the patient can be ambulatory and go about most daily activities, thereby enhancing the patient's quality-of-life and improving patient compliance with the course of treatment using the inventive system. In one embodiment, the controller is configured for implantation at a suitable location within the patient, e.g., subcutaneously under the clavicle. In such an embodiment, the implantable controller is configured for bidirectional communication with an external controller, e.g., mobile device or system-specific device. The external controller may be configured to charge the battery of the implantable controller, e.g., via respective inductive coils in each controller, and may receive data indicative of the sensed parameters including heart rate, blood flow rate, blood volume, pressure including cardiac filling pressure. One or more external power sources may be in electrical communication with the implantable controller and also may be configured to provide power to the controller to charge the battery of the implantable controller. The one or more external power sources may generate an alert when a power level of the one or more external power sources is below a threshold power level.

In a preferred embodiment, the flow limiting element comprises a non-compliant or semi-compliant balloon or balloons affixed to a distal region of the catheter, such that the controller actuates the balloon by periodically inflating and deflating the balloon to selectively fully or partially occlude the SVC and/or the azygos vein. For example, the controller may be programmed to intermittently actuate the flow limiting element to at least partially occlude the SVC for a first predetermined time interval and to contract for a second predetermined time interval over multiple cardiac cycles. The first predetermined time interval may be at least five times greater than the second predetermined time interval. For example, the first predetermined time interval may be 4-6 minutes, while the second predetermined time interval is 1-30 seconds. In alternative embodiments, the flow limiting element may comprise membrane covered umbrellas, baskets or other mechanical arrangement capable of being rapidly transitioned between deployed and contracted positions, e.g., by a driveline connected to the controller. In still further embodiments, the flow limiting element may take the form of a butterfly valve or ball valve, provided the flow limiting element does not create stagnant flow zones in the SVC when in the contracted or open position. In yet further embodiments, the flow limiting element comprises a cuff configured to be applied to the exterior of the SVC and operates by narrowing or occluding the SVC when inflated.

The inventive system may include a sensor disposed on the catheter for placement within the venous or arterial vasculature to measure the patient's heart rate or blood pressure. The sensor preferably generates an output signal that is used as an input to the controller to adjust the degree or timing of the occlusion created by the flow limiting element. In another embodiment, the controller may be configured to couple to a third-party heart rate or blood pressure sensor, such as those typically used by sporting enthusiasts, e.g., the Fitbit, via available wireless standards, such as Bluetooth, via the patient's smartphone. In this embodiment, the cost, size and complexity of the controller may be reduced by integrating it with commercially available third-party components.

In accordance with another aspect of the disclosure, a method for controlling blood flow in a patient comprises inserting and guiding to the vena cava of a patient a venous occlusion device, coupling the occlusion device to a controller worn externally by, or implanted in, the patient; and activating the venous occlusion device intermittently, for intervals spanning multiple cardiac cycles, so that over a period of several minutes, hours, days, weeks, or months, remodeling of the myocardium is arrested or reversed.

In accordance with another aspect of the disclosure, a system for use in combination with a ventricular assist device (VAD) for improving efficiency and functionality of the VAD, and for reducing the risk of adverse effects of the VAD, is provided. The system includes a catheter having a proximal end and a distal region, the catheter sized and shaped for placement (e.g., intravascular placement, such as through a subclavian or jugular vein of the patient) so that the distal region is disposed in a superior vena cava (SVC) of the patient. The system also includes a flow limiting element, e.g., an SVC occlusion balloon, disposed on the distal region of the catheter, the flow limiting element selectively actuated to at least partially occlude the SVC, and a controller operatively coupled to the catheter to intermittently actuate the flow limiting element to at least partially occlude the SVC for an interval spanning a single or multiple cardiac cycles, thereby reducing cardiac preload and pulmonary artery pressure to improve cardiac performance. For example, the controller may reduce cardiac preload during the interval sufficiently to improve cardiac performance as measured by at least one of: reduced cardiac filling pressures, increased left ventricular relaxation, increased left ventricular capacitance, increased left ventricular stroke volume, increased lusitropy, reduced left ventricular stiffness or reduced cardiac strain.

The system further may include a first pressure sensor disposed on the catheter proximal to the flow limiting element, the first pressure sensor outputting a first pressure signal, and a second pressure sensor disposed on the catheter and distal to the flow limiting element, the second pressure sensor outputting a second pressure signal, wherein the controller generates a first signal corresponding to a difference between the first pressure signal and the second pressure signal, the first signal indicative of a degree of occlusion of the flow limiting element. The controller may use the first signal to determine when to actuate the flow limiting element to at least partially occlude the SVC and when to cease actuation of the flow limiting element. The controller also may be programmed to activate an alarm as a safety signal for the operator based on the first signal. In one embodiment, the controller is configured for implantation at a suitable location within the patient, e.g., subcutaneously under the clavicle.

In addition, the controller may be programmed to intermittently actuate the flow limiting element to at least partially occlude the SVC for a first predetermined time interval and to contract for a second predetermined time interval over multiple cardiac cycles. The first predetermined time interval may be at least ten times greater than the second predetermined time interval. For example, the first predetermined time interval may be 4-6 minutes, while the second predetermined time interval is 1-10 seconds.

In one preferred embodiment, the flow limiting element is an inflatable cylindrical balloon, the inflatable cylindrical balloon having a relief valve coupled to the inflatable cylindrical balloon having an open and closed position. The relief valve may be opened at a predetermined pressure between 30-60 mmHg to permit fluid to flow through the SVC to a right atrium of the patient. The system further may include an azygos vein occlusion balloon disposed on the catheter proximal to the flow limiting element. The azygos vein occlusion balloon may be selectively actuated to at least partially occlude an azygos vein of the patient, and the azygos vein occlusion balloon and the SVC occlusion balloon may be independently actuated. In addition, the system permits operation of the VAD at slower speeds to achieve a hemodynamic response equivalent to or greater than a VAD-only hemodynamic response at higher speeds In addition, the system may include a left ventricular assist device (LVAD), the LVAD including a catheter having a proximal end and a distal region, the distal region having an inflow end and an outflow end, the catheter sized and shaped for placement through a femoral artery of the patient so that the inflow end is disposed in a left ventricle of the patient and the outflow end is disposed in an aorta of the patient. The LVAD also includes a pump, e.g., an impeller pump, disposed on the distal region of the catheter, wherein the pump may be selectively actuated to pump blood from the left ventricle through the inflow end and expel blood into the aorta via the outflow end, and an LVAD controller operatively coupled to the LVAD to actuate the pump to pump blood from the left ventricle to the aorta, thereby unloading the left ventricle and increasing coronary and systemic perfusion. The LVAD controller operatively coupled to the catheter of the system may regulate the activation and deactivation of the flow limiting element to at least partially occlude the SVC simultaneously as the LVAD controller actuates the pump to pump blood from the left ventricle to the aorta.

Alternatively or in addition to, the system may further include a right ventricular assist device (RVAD), the RVAD including a pump, e.g., an impeller pump, that may be selectively actuated to pump blood from the SVC through an inflow end of the RVAD and expel blood into a pulmonary artery via an outflow end of the RVAD. The controller also may be operatively coupled to the RVAD to actuate the pump to pump blood from the SVC to the pulmonary artery, thereby unloading the right ventricle. For example, the controller may actuate the flow limiting element to at least partially occlude the SVC simultaneously as the controller actuates the pump to pump blood from the SVC to the pulmonary artery.

In another preferred embodiment, the RVAD includes a catheter having a proximal end and a distal region, the distal region having an inflow end and an outflow end, the catheter sized and shaped for placement through a femoral vein of the patient so that the outflow end is disposed in a pulmonary artery of the patient and the inflow end is disposed in an IVC of the patient. The RVAD also includes a pump, e.g., an impeller pump, disposed on the distal region of the catheter, wherein the pump may be selectively actuated to pump blood from the IVC through the inflow end and expel blood into the pulmonary artery via the outflow end, and an RVAD controller operatively coupled to the RVAD to actuate the pump to pump blood from the IVC to the pulmonary artery, thereby unloading the right ventricle. The RVAD controller operatively coupled to the catheter of the system may regulate the activation and deactivation of the flow limiting element to at least partially occlude the SVC simultaneously as the RVAD controller actuates the pump to pump blood from the IVC to the pulmonary artery.

BRIEF DESCRIPTION OF THE DRAWINGS

The characteristics and advantages of the present invention will become apparent from the detailed description of the embodiment of the disclosure presented below in conjunction with the attached drawings, in which:

FIGS. 8A and 8B are schematic drawings of a flow limiting element comprising a ball-shaped balloon shown in its expanded and contracted states, respectively.

FIGS. 9A and 9B are schematic drawings of a flow limiting element comprising a spring-loaded plug shown in its expanded and contracted states, respectively.

FIGS. 10A and 10B are schematic drawings of a flow limiting element comprising an alternative embodiment of a spring-loaded plug shown in its expanded and contracted states, respectively.

FIGS. 15-22 show test results for swine subjects subjected to heart failure.

FIG. 32 is a perspective view of the cylindrical flow limiting element.

FIG. 33 is a cross-sectional view of the cylindrical flow limiting element showing the relief valve.

FIGS. 40A-B are perspective and cutaway views of a stent coupled to a relief valve.

DETAILED DESCRIPTION OF THE INVENTION

Figure 1A:
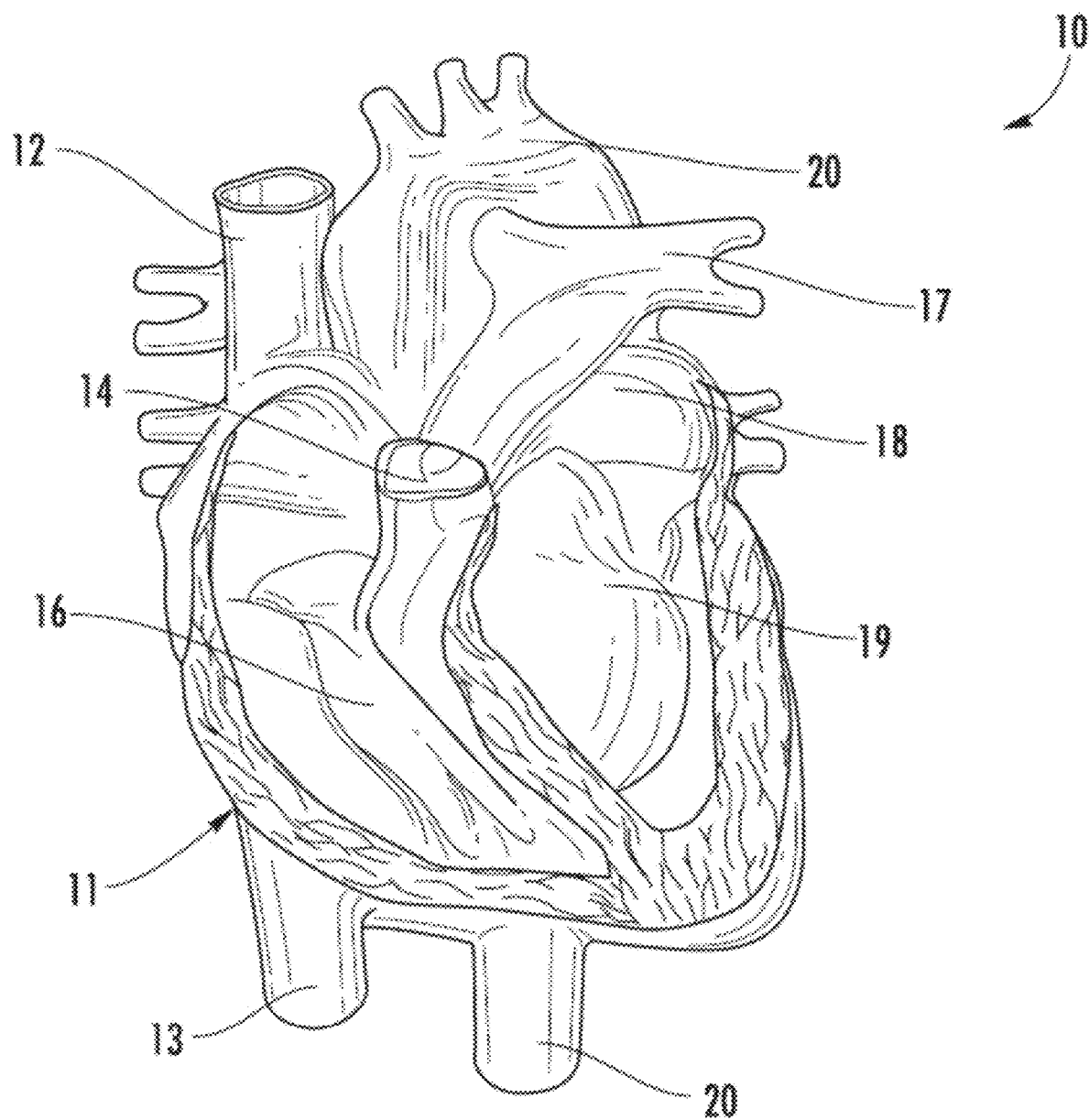
FIG. 1A is a frontal, partially broken-away view of the major arteries and veins of the heart.
Figure 1B:
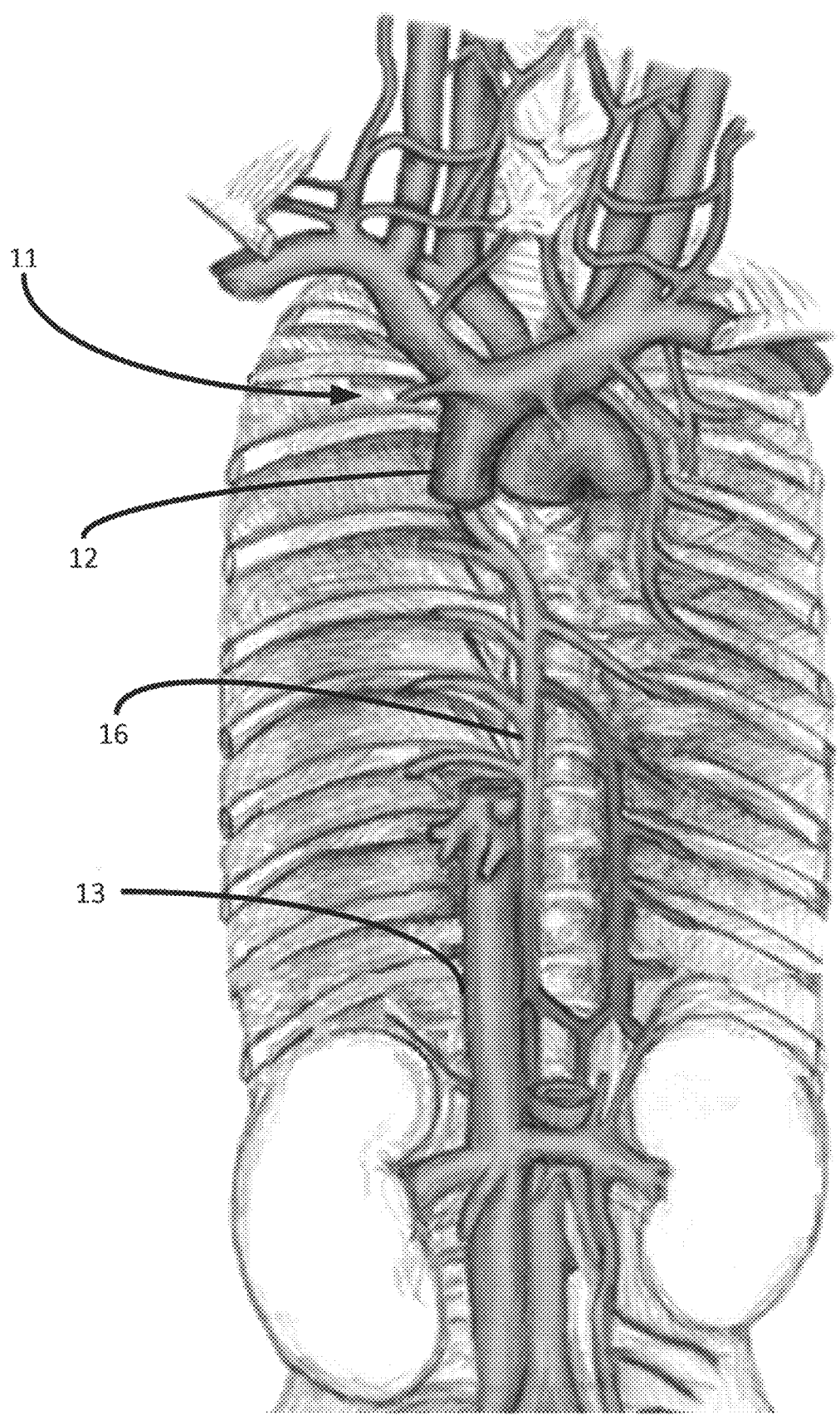
FIG. 1B illustrates the vena cava including major veins associated with the vena cava.

Referring to FIGS. 1A and 1B, the human anatomy in which the present invention is designed for placement and operation is described as context for the system and methods of the present invention.

More particularly, referring to FIG. 1A, deoxygenated blood returns to heart 10 through vena cava 11, which comprises superior vena cava 12 and inferior vena cava 13 coupled to right atrium 14 of the heart. Blood moves from right atrium 14 through tricuspid valve 15 to right ventricle 16, where it is pumped via pulmonary artery 17 to the lungs. Oxygenated blood returns from the lungs to left atrium 18 via the pulmonary vein. The oxygenated blood then enters left ventricle 19, which pumps the blood through aorta 20 to the rest of the body.

As shown in FIG. 1B, superior vena cava 12 is positioned at the top of vena cava 11, while inferior vena cava 13 is located at the bottom of the vena cava. FIG. 1B also shows azygos vein 16 and some of the major veins connecting to the vena cava. As noted herein, occlusion of the inferior vena cava 13 may pose risks of venous congestion, and in particular, potential blockage or enlargement of the hepatic veins and/or suprarenal vein that may worsen, rather than improve, the patient's cardiovascular condition and overall health.

In accordance with one aspect of the present invention, applicants have determined that selective intermittent occlusion of the superior vena cava ("SVC") poses fewer potential adverse risks than occlusion of the inferior vena cava ("IVC"). Moreover, applicants' animal and human testing reveals that controlling the return of venous blood to the right ventricle by partially or fully occluding the SVC beneficially lowers RVEDP, RVEDV, LVEDP and LVEDV without adversely reducing left ventricular systolic pressure (LVSP).

Applicants understand that selective intermittent occlusion of the SVC will reduce the risk of worsening congestion of the kidneys, which is a major cause of 'cardio-renal' syndrome, as compared to IVC occlusion. Cardio-renal syndrome is impaired renal function due to volume overload and neurohormonal activation in patients with heart failure. Volume overload may occur where the weakened heart cannot pump as much blood, which leads to less blood flow through the kidneys. With less blood flow through the kidneys, less blood is filtered by the kidneys and less water is released via urination causing excess volume to be retained in the body. With the excess volume, the heart pumps with increasingly less efficiency and the patient ultimately spirals toward death as the body becomes progressively more congested.

Applicants understand that IVC occlusion generally reduces the blood flow through the kidneys as the occluded IVC increases pressure in the renal vein, thereby reducing the kidneys ability to filter out fluid. IVC occlusion further causes blood to back-up and otherwise prevents deoxygenated blood from returning to the heart. As a result, renal function may too be reduced, worsening congestion. However, SVC occlusion ultimately increases flow to the kidneys thereby improving renal function. Specifically, by reducing flow into the right atrium via SVC occlusion, volume within the left ventricle is ultimately reduced, permitting the muscle fibers to stretch within a normal range, naturally increasing contractility and allowing the heart to drive more fluid to the kidneys. The kidneys may then extract water, which may be removed from the body through urination. It is further understood that during SVC occlusion, a negative pressure sink is created in the right atrium caused by an abrupt reduction in right atrial pressure and volume. As a result, flow from the renal vein may be accelerated thereby enhancing renal decongestion and promoting blood flow across the kidney, increasing urine output. Accordingly, SVC occlusion may benefit patients with heart failure and/or cardiorenal syndrome by reducing cardiac and pulmonary pressures and promoting decongestion.

In addition, implantation in the SVC permits a supra-diaphragmatic device implant that could not be used in the IVC without cardiac penetration and crossing the right atrium. Further, implantation of the occluder in the SVC avoids the need for groin access as required by IVC implantation, which would limit mobility making an ambulatory device impractical for short term or long term use. In addition, minor changes in IVC occlusion (time or degree) may cause more dramatic shifts in preload reduction and hence total cardiac output/systemic blood pressure whereas the systems and methods of the present invention as expected to permit finely tuned decrease in venous return (preload reduction).

Applicants understand that intermittent occlusion of the SVC (i.e., cardio-pulmonary unloading) over a period of time (e.g., minutes, hours, days, weeks, or months) will beneficially permit a patients' heart to discontinue or recover from remodeling of the myocardium. Applicants' animal and human testing indicates that the system enables the myocardium to transition from pressure-stroke volume curve indicative of heart failure towards a pressure-stroke volume curve more closely resembling that of a healthy heart.

In general, the system and methods of the present invention may be used to treat any disease to improve cardiac function by arresting or reversing myocardial remodeling, and particularly those conditions in which a patient suffers from heart failure. Such conditions include but are not limited to, e.g., systolic heart failure, diastolic (non-systolic) heart failure, decompensated heart failure patients in (ADHF), chronic heart failure, acute heart failure and pulmonary hypertension, heart attacks, heart failure with preserved ejection fraction, right heart failure, constrictive and restrictive cardiomyopathies, and cardio-renal syndromes (Types 1-5). The system and methods of the present invention also may be used as a prophylactic to mitigate the aftermath of acute right or left ventricle myocardial infarction, pulmonary hypertension, RV failure, post-cardiotomy shock, or post-orthotopic heart transplantation (OHTx) rejection, or otherwise may be used for cardiorenal applications and/or to treat renal dysfunction, hepatic dysfunction, or lymphatic congestion. Also, the system and methods of the present invention may reduce hospital stays caused by various ailments described herein, including at least acute exacerbation.

Figure 2A:
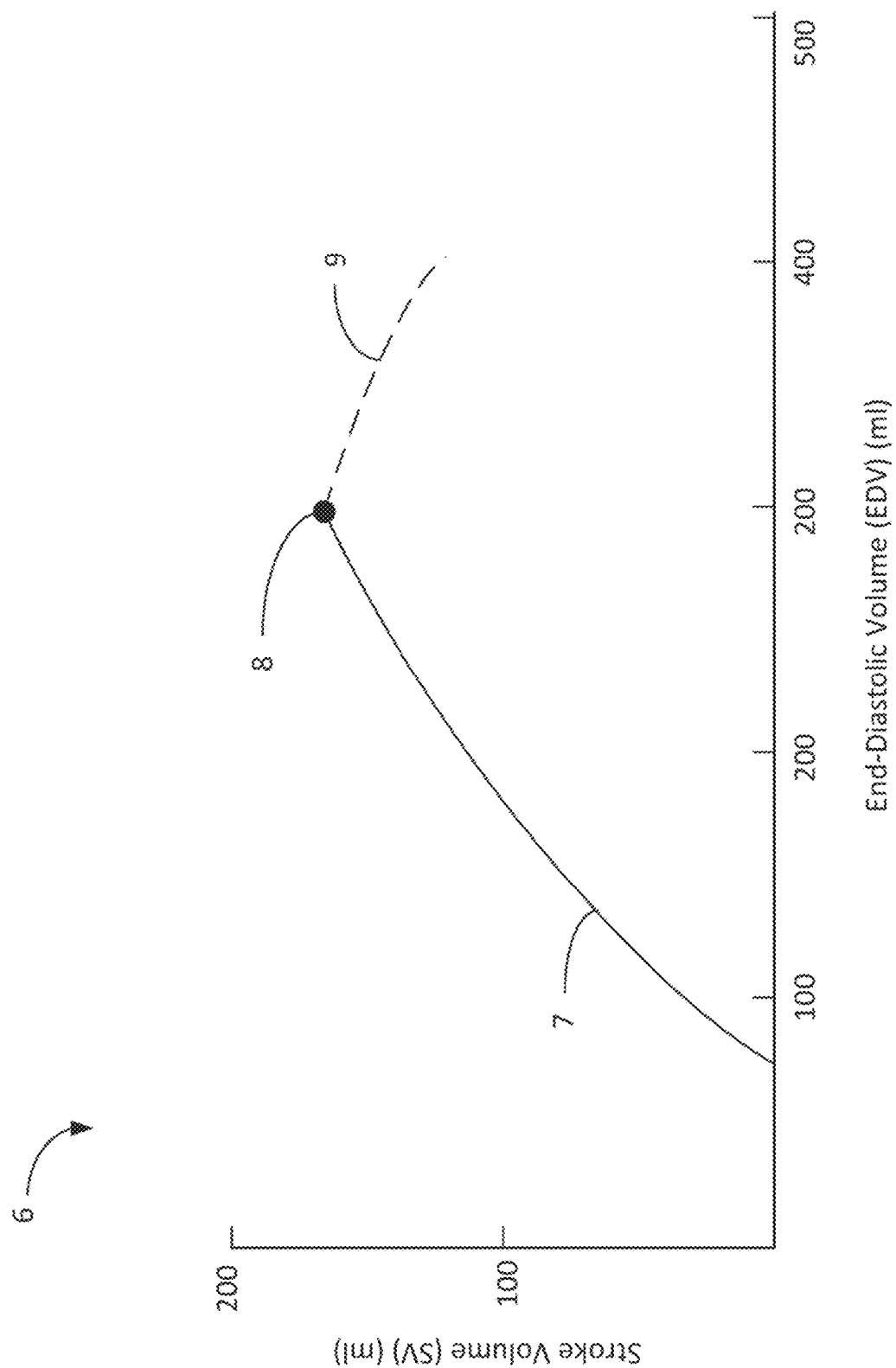
FIGS. 2A and 2B illustrate Frank-Starling curves for normal and afflicted cardiac conditions.
Figure 2B:
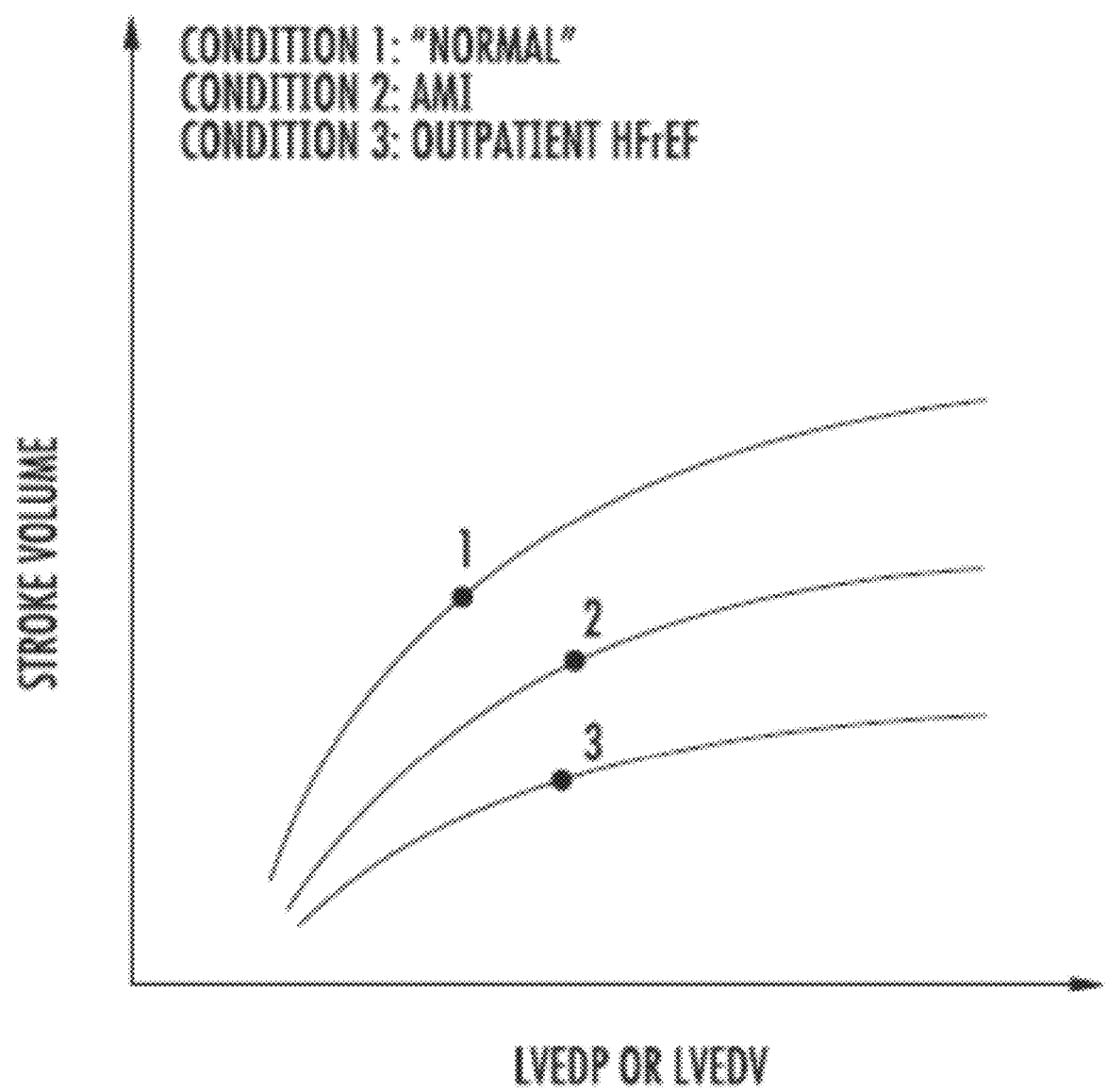

The relationship between left ventricular pressure or left ventricular volume and stroke volume is often referred to as the Frank-Starling relationship, or "Starling curve" and is illustrated in FIGS. 2A-2B. That relationship states that cardiac stroke volume is dependent on preload, contractility, and afterload. Preload refers to the volume of blood returning to the heart; contractility is defined as the inherent ability of heart muscle to contract; and afterload is determined by vascular resistance and impedance. In heart failure due to diastolic or systolic dysfunction, reduced stroke volume leads to increased volume and pressure increase in the left ventricle, which can result in pulmonary edema. Increased ventricular volume and pressure also results in increased workload and increased myocardial oxygen consumption. Such over-exertion of the heart results in worsening cardiac function as the heart becomes increasingly deprived of oxygen due to supply and demand mismatch. Furthermore, as volume and pressure build inside the heart, contractile function worsens due to stretching of cardiac muscle. This condition is termed "congestive heart failure."

Referring to FIG. 2A, a series of Starling curves are illustrated, in which topmost curve (curve 1) depicts functioning of a normal heart. As shown in the curve, stroke volume increases with increasing LVEDP or LVEDV, and begins to flatten out, i.e., the slope of the curve decreases, only at very high pressures or volumes. A patient who has just experienced an acute myocardial infarction ("AMI"), as indicated by the middle curve (curve 2), will exhibit reduced stroke volume at every value of LVEDV or LVEDP. However, because the heart has just begun to experience the overload caused by the localized effect of the infarct, myocardial contractility of the entire ventricle is still relatively good, and stroke volume is still relatively high at low LVEDP or LVEDV. By contrast, a patient who has suffered from cardiac injury in the past may experience progressive deterioration of cardiac function as the myocardium remodels over time to compensate for the increased workload and reduced oxygen availability, as depicted by the lowermost curve (curve 3) in FIG. 2A. As noted above, this can lead to progressively lower stroke volume as the ventricle expands due to generally higher volume and pressure during every phase of the cardiac cycle. As will be observed from comparison of curves 1 and 3, the stroke volume continues to decline as the LVEDP or LVEDV climb, until eventually the heart gives out or the patient dies of circulatory-related illness.

FIG. 2B provides an alternative formulation of a Frank-Starling curve, curve 6, illustrating the differences between functioning of a healthy heart and one in heart failure. Line 7, up to point 8, illustrates a Frank-Starling curve for a normal healthy heart As discussed with respect to FIG. 2A, for a normal heart, as the end-diastolic volume increases, the stroke volume increases. For a healthy heart, however, beyond point 8, increased end-diastolic volume no longer results in increased stroke volume, and continued increases in end-diastolic volume do not result in further increases in stroke volume. This phenomenon is shown that the solid flat line that extends substantially horizontally beyond point 8. Decreasing dotted line 9, which extends beyond 8, in FIG. 2B, represents a Frank-Starling curve for a patient in heart failure. Dotted line 9 indicates that for patients with heart failure, further increases in end-diastolic volume do not result in a substantially flat stroke volume, but instead stroke volume decreases. Accordingly, increasing EDV for patients with HF results in further reduction in SV, leading to a downward spiral in heart function, and ultimately death. FIG. 2B reflects a phenomenon referred to as "diastolic ventricular interaction," which arises in part due to the structural arrangement of the cardiac chambers. As discussed, for example, in an article entitled "Diastolic ventricular interaction in chronic heart failure," Lancet 1997; 349:1720-24 by J. Atherton et al., the pericardium constrains the extent to which the ventricles of a failing heart can expand. Consequently, as right ventricular end diastolic volume increases, it necessarily causes a reduction in the end diastolic volume of the left ventricle. As reported in that article, reduction in right ventricular diastolic filling caused by external lower body suction allows augmented left ventricular diastolic filling.

Applicants understand that the foregoing phenomenon can advantageously be utilized in the context of the present invention to improve cardiac performance. In particular, in heart failure and the presence of pulmonary hypertension, right ventricular congestion due to increased volume overload can push the interventricular septum towards the left ventricular cavity, thereby reducing LV stroke volume and cardiac output. By occluding flow through the SVC, right ventricular pressure and volume are reduced. This in turn will shift the interventricular septum away from the LV cavity, allowing for increased left ventricular stroke volume and enhanced cardiac output. For these reasons, SVC occlusion in accordance with the principles of the present invention may favorably alter diastolic ventricular interaction and enhance cardiac output. Specifically, with respect to diastolic heart failure, SVC occlusion in accordance with the principles of the present invention may provide a reduction in cardiac filling pressures, increased LV relaxation (tau), increased LV capacitance, increased lusitropy, reduced LV stiffness, and reduced cardiac strain. The effect of the SVC occlusion of the present invention can thus be visualized as shifting dotted line 9 of Frank-Starling curve 6 in FIG. 2B for a patient in heart failure towards lower EDV, which in effect moves the cardiac performance upwards and closer towards the flat portion of the curve that extends beyond point 8 for a healthy patient. The system and methods of inducing at least partial intermittent SVC occlusion of the present invention for patients in HF therefore improves heart function by moving a patient's heart contractility toward a healthy range of the patient's Frank-Starling curve.

Figure 3:
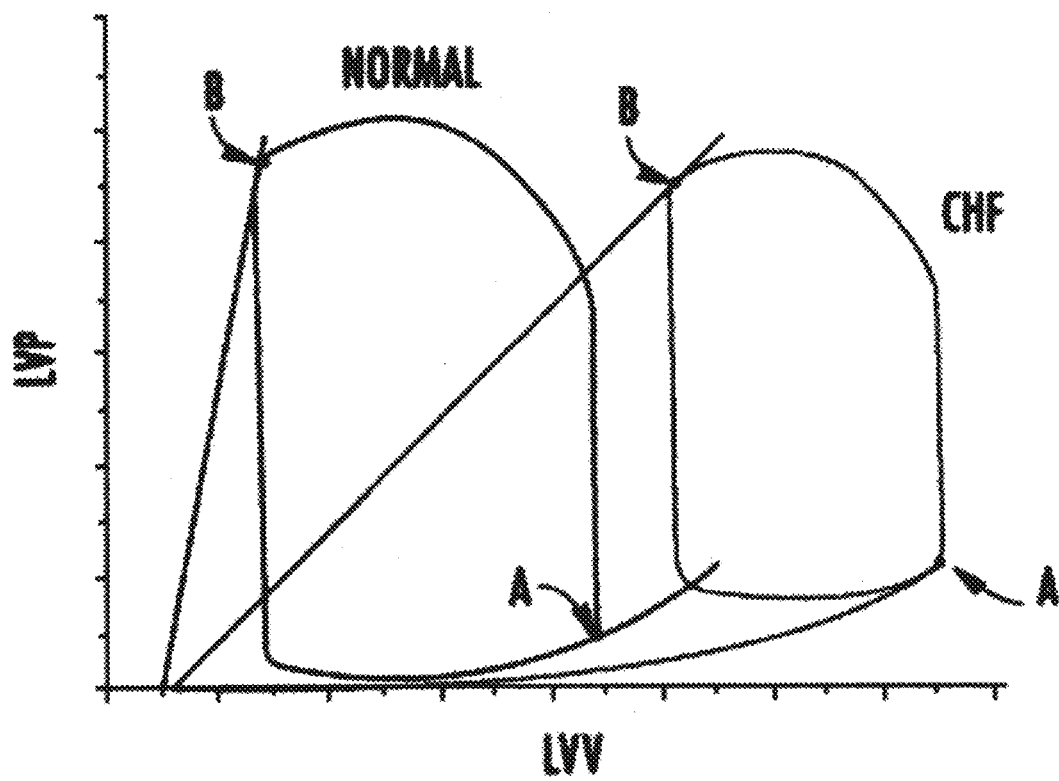
FIG. 3 is a graph of exemplary pressure-volume loop curves of left ventricular pressure versus left ventricular volume throughout a cardiac cycle for a patient having normal cardiac function and a patient suffering from congestive heart failure.

FIG. 3 illustratively shows pressure-volume loops for a normal heart, labeled "normal", corresponding to curve 1 in FIG. 2B, and a heart suffering from congestive heart failure, labeled "CHF" (curve 3 in FIG. 2B). For each loop, the ventricular volume and pressure at the end of diastole correspond to the lower-most, right-most corner of the loop (point A), while the upper-most, left-most corner of each loop corresponds to the beginning systole (point B). The stroke volume for each pressure-volume loop corresponds to the area enclosed within the loop. Accordingly, the most beneficial venous regulation regime is one that reduces the volume and pressure at point A while not also causing negligible reduction in point B, thereby maximizing the stroke volume.

In accordance with one aspect of the present invention, the system and methods are designed, over the course of hours, days, weeks, or months, to shift or transition the Starling curve of the patient's heart leftwards on the diagram of FIG. 2B (or to move the pressure-volume loop in FIG. 3 leftwards and downwards). This may be accomplished by intermittently fully or partially occluding the SVC to reduce the volume and hence pressure of blood entering the right ventricle, and which must then be pumped by the left ventricle. Applicants' preliminary animal testing indicates that such intermittent occlusion, maintained over several cardiac cycles, reduces the workload and wall stress in the myocardium throughout the cardiac cycle, reduces myocardial oxygen consumption, and improves contractile function.

Figure 4A:
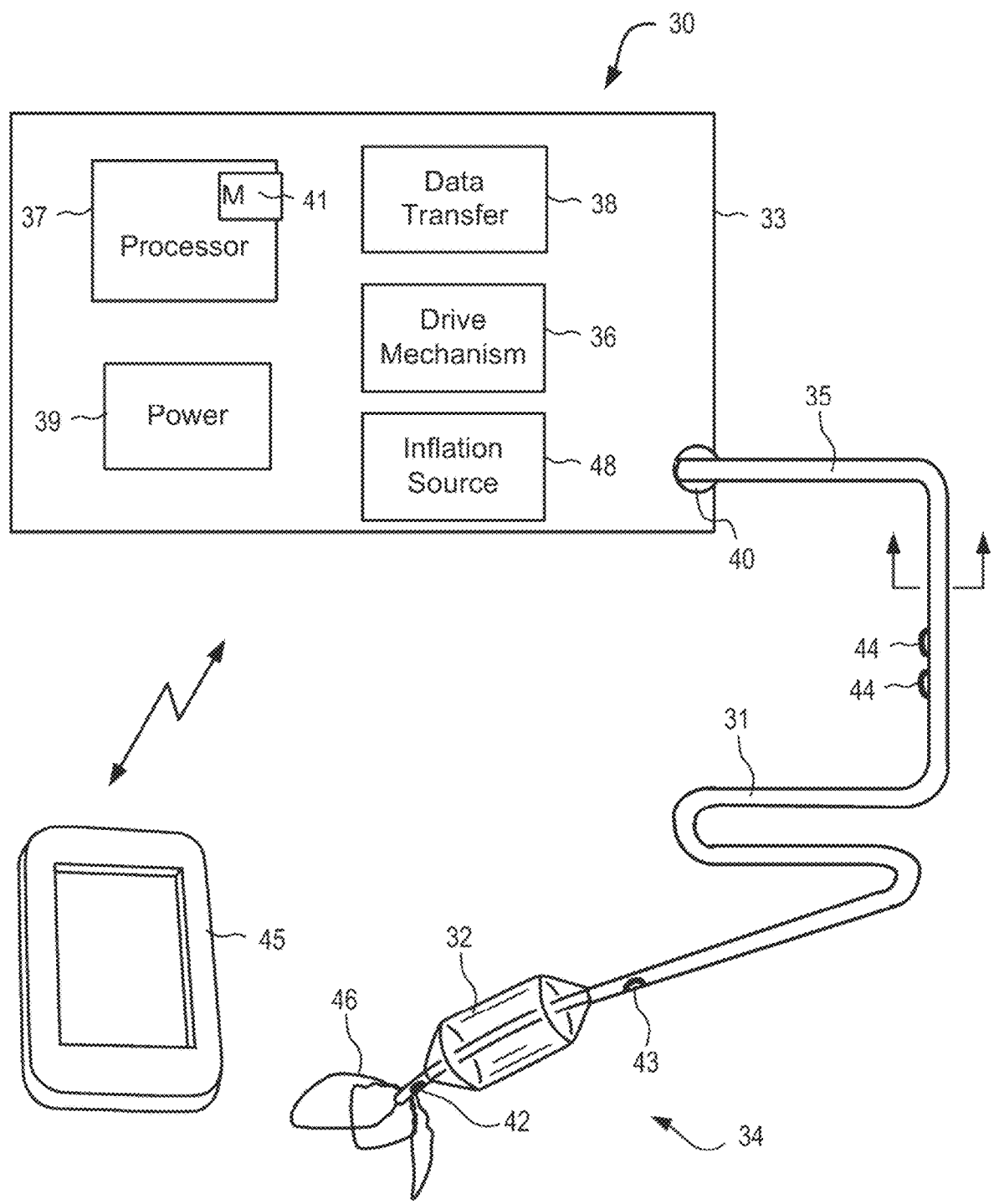
FIG. 4A is a schematic drawing of a system constructed in accordance with the principles of the present invention.

Referring now to FIG. 4A, exemplary system 30 of the present invention is described. System 30 includes catheter 31 having flow limiting element 32 coupled to controller 33 programmed to intermittently actuate flow limiting element 32. As discussed below, system 30 optionally may be configured to transfer information bi-directionally with conventional computing device 45 such as a smartphone, laptop, smartwatch, or tablet, illustratively an Apple iPhone 5 or iPad, available from Apple Inc., Cupertino, California, on which a special-purpose application has been installed to communicate and/or control controller 33.

Preferably, catheter 31 comprises a flexible tube having distal portion 34 configured for placement in the SVC. Distal portion 34 includes flow limiting element 32 that, in use, is disposed in superior vena cava 12 (see FIG. 1B) of a patient to selectively impede blood flow into right atrium 14. In this embodiment, flow limiting element 32 illustratively comprises a balloon capable of transitioning between a contracted state, allowing transluminal placement and an expanded, deployed state. Flow limiting element 32 preferably is sized and shaped so that it partially or fully occludes flow in the SVC in the expanded state. Catheter 31 is coupled at proximal end 35 to controller 33, which houses drive mechanism 36 (e.g., motor, pump) for actuating flow limiting element 32, processor 37 programmed to control signals to drive mechanism 36, and optional sensor 42 for monitoring a physiologic parameter of the patient, such as heart rate or blood pressure.

Controller 33 may include source of inflation medium 48 (e.g., gas or fluid) and drive mechanism 36 may transfer the inflation medium between the source and flow limiting element 32 responsive to commands from processor 37. When flow limiting element 32 is inflated with inflation medium, it partially or fully occludes venous blood flow through the SVC; when the inflation medium is withdrawn, flow limiting element 32 deflates to remove the occlusion, thereby permitting flow to resume in the SVC. Flow limiting element 32 may be a balloon that preferably comprises a compliant or semi-compliant material, e.g., nylon, which permits the degree of expansion of the balloon to be adjusted to effectuate the desired degree of partial or complete occlusion of the SVC. In addition, catheter 31, when partially external, provides a fail-safe design, in that flow limiting element 32 only can be inflated to provide occlusion when the proximal end of catheter 31 is coupled to controller 33. Such a quick-disconnect coupling 40 at proximal end 35 permits the catheter to be rapidly disconnected from controller 33 for cleaning and/or emergency.

Controller 33 preferably also includes power supply 39 (e.g., battery) that provides the power needed to operate processor 37, drive mechanism 36 and data transfer circuit 38. Controller 33 may be sized and of such a weight that it can be worn in a harness under the patient's clothing, so that the system can be used while the patient is ambulatory or such that controller 33 may be implanted within the patient. As discussed herein below, processor 37 includes memory 41 for storing computer software for operating the controller 33. Controller 33 may be configured for implantation at a suitable location within the patient, e.g., subcutaneously under the clavicle. In such an embodiment, the implantable controller is configured for bidirectional communication with an external controller, e.g., computing device 45 or system-specific device. An external controller may be used to charge the battery of the implantable controller, e.g., via respective inductive coils in or coupled to each controller, and may receive data indicative of the sensed parameters resulting from the patient's ambulatory activity including heart rate, blood flow rate, blood volume, pressure including cardiac filling pressure.

In one embodiment, data transfer circuit 38 monitors an input from an external sensor, e.g., positioned on catheter 31, and provides that signal to processor 37. Processor 37 is programmed to receive the input from data transfer circuit 38 and adjust the interval during which flow limiting element 32 is maintained in the expanded state, or to adjust the degree of occlusion caused by flow limiting element 32. Thus, for example, catheter 31 may have optional sensor 42 positioned within distal portion 34 of the catheter to measure parameters, e.g., heart rate, blood flow rate, blood volume, pressure including cardiac filling pressure and central venous pressure. The output of sensor 42 is relayed to data transfer circuit 38 of controller 33, which may pre-process the input signal, e.g., decimate and digitize the output of sensor 42, before it is supplied to processor 37. The signal provided to processor 37 allows for assessment of the effectiveness of the flow limiting element, e.g., by showing reduced venous pressure during occlusion and during patency, and may be used for patient or clinician to determine how much occlusion is required to regulate venous blood return based on the severity of congestion in the patient. Additionally, sensor 43 may be included on catheter 31 proximal to flow limiting element 32, to measure parameters, e.g., heart rate, blood flow rate, blood volume, pressure including cardiac filling pressure and central venous pressure. Sensor 43 may be used to determine the extent of occlusion caused by element 32, for example, by monitoring the pressure drop across the flow limiting element.

As another example, catheter 31 may include electrodes 44 for sensing the patient's heart rate. Applicants understand that it may be desirable to adjust the interval during which occlusion of the SVC is maintained responsive to the patient's ambulatory activities, which typically will be reflected in the patient's hemodynamic state by a sensed physiological parameter(s), e.g., heart rate, blood flow rate, blood volume, pressure including cardiac filling pressure and/or central venous pressure. Accordingly, electrodes 44 may provide a signal to data transfer circuit 38, which in turn processes that signal for use by the programmed routines run by processor 37. For example, if the occlusion is maintained for a time programmed during initial system setup to reflect that the patient is resting, e.g., so that flow limiting element is deployed for 5 seconds and then released for two seconds before being re-expanded, it may be desirable to reduce the occluded time interval to 4 seconds or more depending upon the level of physical activity of the patient, as detected by a change in heart rate, blood flow rate, blood volume, pressure including cardiac filling pressure and/or central venous pressure above or below predetermined thresholds. Alternatively, processor 37 may be programmed to maintain partial or full occlusion in the SVC for a preset number of cardiac cycles determined at the time of initial implantation of the catheter. Sensor inputs provided to data transfer circuit 38, such as hemodynamic state, also may be used to adjust the duty cycle of the flow limiting element responsive to the patient's detected level of activity. In addition, processor 37 may be programmed to maintain partial or full occlusion in the SVC for a preset number of cardiac cycles after adjustment to the predetermined occlusion interval is made.

Data transfer circuit 38 also may be configured to provide bi-directional transfer of data, for example, by including wireless circuitry to transfer data from controller 33 to an external unit for display, review or adjustment. For example, data transfer circuit may include Bluetooth circuitry that enables controller 33 to communicate with patient's computing device 45. In this manner, controller may send information regarding functioning of the system directly to computing device 45 for display of vital physiologic or system parameters using a suitably configured mobile application. In addition, the patient may review the data displayed on the screen of computing device 45 and determine whether he or she needs to seek medical assistance to address a malfunction or to adjust the system parameters. Further, the mobile application resident on computing device 45 may be configured to automatically initiate an alert to the clinician's monitoring service via the cellular telephone network.

Optionally, data transfer circuit 38 may be configured to synchronize to receive data from other mobile applications on computing device 45, and thus reduce the cost and complexity of the inventive system. For example, a number of third party vendors, such as Fitbit, Inc., San Francisco, California, market monitors that measure physiologic parameters in real time, such as the Charge HR wristband monitor, that measures physical activity and heart rate. In accordance with one aspect of the disclosure, data transfer circuit 38 can be programmed to receive an input from such a third-party monitor via wireless communication with computing device 45, and that processor 37 may be programmed to control activation of drive mechanism 36 responsive to that input. In this embodiment, the catheter need not include optional sensor 42, sensor 43 or electrodes 44, thereby greatly simplifying the construction of catheter 31 and coupling 40.

Catheter 31 may include anchor member 46 configured to anchor flow limiting element 32 within the SVC. Anchor member 46 may be contractible for delivery in a contracted state and expandable upon release from a delivery device, e.g., a sheath. Anchor member 46 may be coupled to catheter proximal or distal to flow limiting element 32 and/or may be coupled to flow limiting element 32. The system shown in FIG. 4A may effectively shift a patient's heart contractility into a healthy range of the Frank-Starling curve illustrated in FIG. 2A.

Figure 4B:
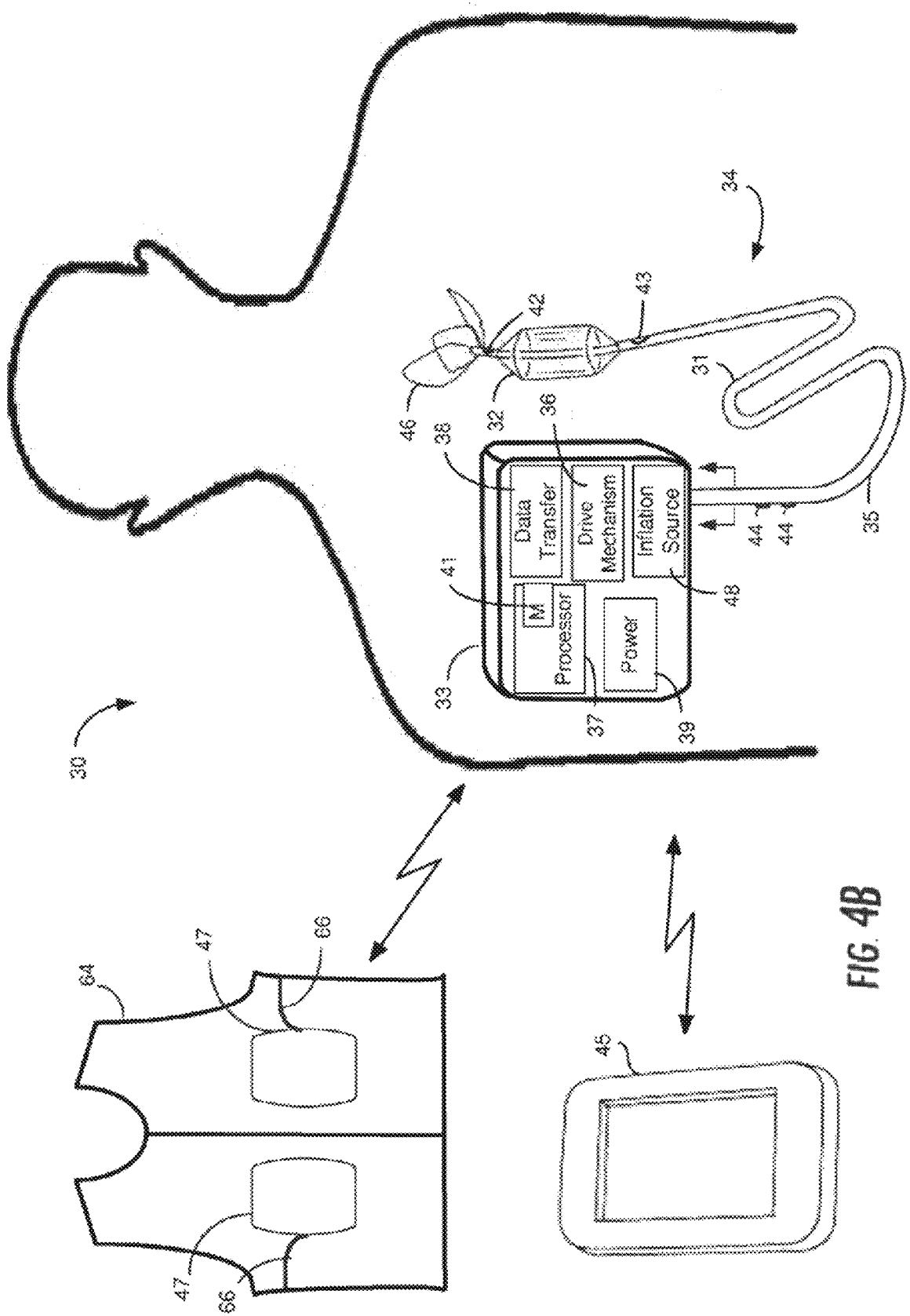
FIG. 4B is a schematic drawing of an implantable system constructed in accordance with the principles of the present invention.

Referring now to FIG. 4B, controller 33 is shown implanted at a suitable location within the patient. As is illustrated in FIG. 4B, external power source 47 may be configured to charge power supply 39 (e.g., battery) of the implantable controller. For example, external power source 47 may transcutaneously charge power supply 39 via respective inductive coils. External power source 47 may be integrated into clothing or a harness worn by the patient. Specifically, external power source 47 may be placed in a pocket or holder configured to receive external power source 47. When the garment or harness is worn by the patient, the pocket or holder may be designed to place external power source 47 in close proximity to battery 39 for efficient transcutaneous charging. More than one external power source 47 may be integrated into the garment to provide additional power. The one or more external power sources may be permanently integrated into the garment or harness or may be removably engaged with the garment or harness such that each may be individually removed and attached. For example, two external power sources 47 may be integrated into specially designed pockets of vest 64 as is illustrated in FIG. 4B. Vest 64 may include wire 66 incorporated into vest 64 to permit electrical communication between the two external power sources.

Power source 47 may generate an alert when an available power supply reaches or falls below a certain threshold power level. For example, power source 47 may have a visual indicator and/or an auditory indicator for providing a warning to the patient or caregiver. The visual indicator may be an LED light system or a display embedded into a surface of power source 47 that visually provides information regarding the available power supply. The auditory indicator may be a speaker embedded into power source 47 that sounds an alarm when the available power supply reaches a certain threshold. A signal indicating that the available power supply of power source 47 has reached a certain threshold also may or alternatively be communicated directly to an external device, e.g. computing device 45, and/or to controller 33 and then from controller 33 to an external device, e.g. computing device 45, which may be programmed to initiate a visual or audio alert. An additional power source 47 may supply power to power supply 39 when the primary power source runs out of power to ensure power can be continuously provided to power supply 39. Power source 47 may include a processor with memory for transcutaneously transmitting and receiving data from processor 37. The processor of power source 47 may be used to reprogram processor 37 and/or store information about operating parameters to be later downloaded by an external device, e.g. computing device 45.

Figure 4C:
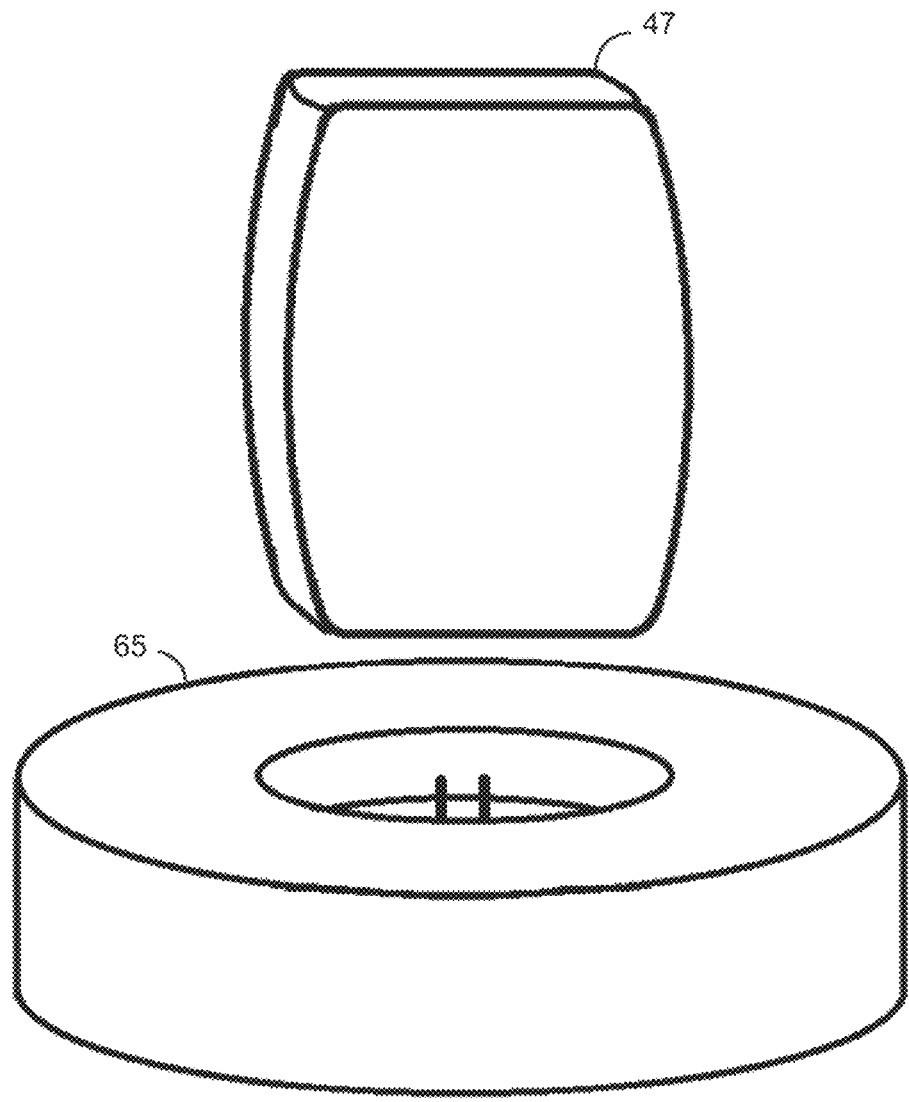
FIG. 4C is a drawing of a power source and a charging base.

Each external power source 47 may be placed in electrical communication with a wall power outlet or base charger 65 shown in FIG. 4C to charge the external power source. Base charger 65 may be in electrical communication with a wall power outlet and may be configured to charge one or more external power sources 47 at the same time. To permit power supply 39 continuous access to a power source, external power sources 47 may be periodically disengaged from the vest and charged such that at least one external power source 47 is in electrical communication with power supply 39 while the other external power source 47 is being charged in base charger 65. Also, by enabling the system to interface with commercially available heart rate monitors and smartphones and/or tablets, the system provides both reduced cost and reduced complexity.

Figure 5A:
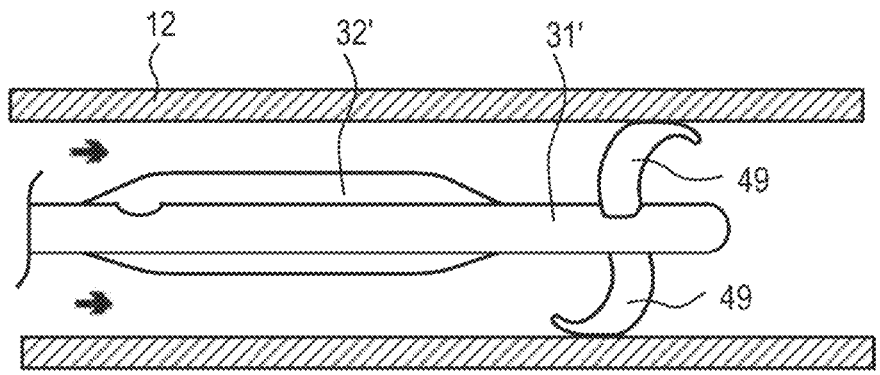
FIGS. 5A-5B are schematic drawings of the catheter of FIG. 4A and FIG. 4B wherein the flow limiting element comprises a cylindrical balloon with modified anchoring members shown in its expanded and contracted states, respectively.
Figure 5B:
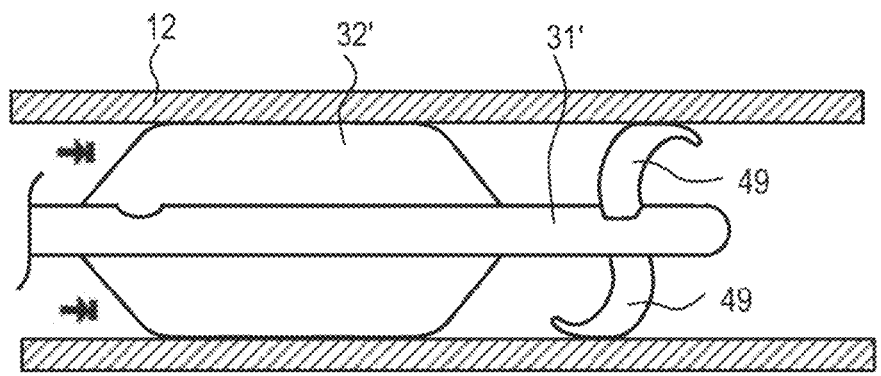

Referring now to FIGS. 5A and 5B, an exemplary embodiment of catheter 31' is described, wherein catheter 31' is constructed similarly to catheter 31 of FIG. 4A and FIG. 4B except with a modified anchor. As shown in FIG. 5A when flow limiting element 32' is in an expanded, fully occluding state, and shown in FIG. 5B, when flow limiting element 32' is in a contracted state, catheter 31' may include radially expanding anchoring arms 49. Anchoring arms 49 are configured to radially expand, e.g., when exposed from a delivery sheath, to contact the inner wall of superior vena cava 12 and anchor flow limiting element 32' therein.

Figure 6:
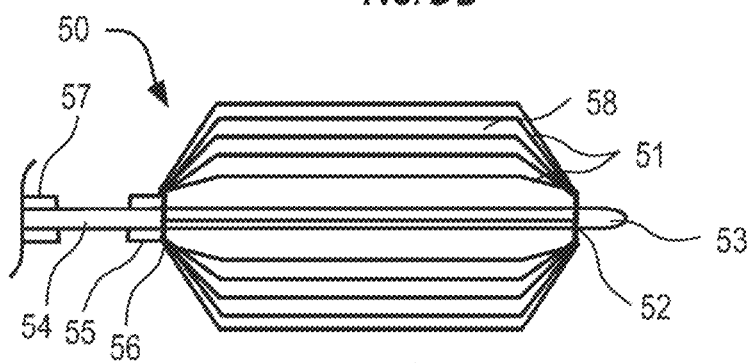
FIG. 6 is a schematic drawing of the catheter of FIG. 4A and FIG. 4B wherein the flow limiting element comprises a mechanically actuated membrane covered basket.

Referring now to FIG. 6, an alternative embodiment is described wherein the occlusion may comprise a wire basket. Flow limiting element 50 may be formed of a biocompatible material, such as nickel-titanium or stainless steel, and comprises plurality of axially or spirally extending wires 51 that are biased to expand radially outward when compressed. Flow limiting element 50 preferably includes a biocompatible membrane covering, so that it partially or fully occludes flow in the SVC in the expanded state. Wires 51 may be coupled at distal end 52 to distal end 53 of actuation wire 54, and affixed to ring 55 at their proximal ends 56. Ring 55 is disposed to slide on actuation wire 54 so that when actuation wire 54 is pulled in the proximal direction against sheath 57 (see FIGS. 5A and 5B), wires 51 expand radially outward. As shown in FIG. 5B, in response to a force applied to the proximal end of actuation wire 54 by drive mechanism 36, actuation wire 54 is retracted proximally against sheath 57 of the catheter; transitioning flow limiting element 50 to its expanded deployed state. Conversely, when drive mechanism 36 is deactivated, spring force applied by wires 51 pulls actuation wire 54 in the proximal direction, thereby enabling wires 51 to return to their uncompressed state, lying substantially flat against actuation wire 54. As noted above, flow limiting element 50 has a "fail safe" design, so that the flow limiting element resumes the collapsed, contracted state shown in FIG. 5A when catheter 31 is uncoupled from drive mechanism 36. In this embodiment, drive mechanism 36 may be a motor, which may be a linear motor, rotary motor, solenoid-piston, or wire motor.

Flow limiting element 50 may be constructed so that it is biased to the contracted position when catheter 31 is disconnected from controller 33, so that flow limiting element 50 can only be transitioned to the expanded, deployed state when the catheter is coupled to controller 33 and the processor has signaled drive mechanism 36 to expand the flow limiting element.

Figure 7:
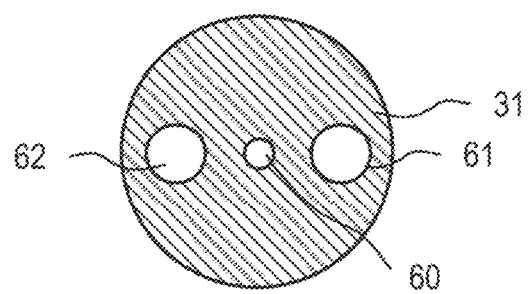
FIG. 7 is a cross-sectional view of the catheter of FIG. 4A and FIG. 4B.

Referring now to FIG. 7, catheter 31 preferably includes at least three lumens 60, 61, 62. Lumen 60 may be used as an inflation lumen and/or for carrying actuation wire 54 that extends between flow limiting element 32/50 and the drive mechanism 36 of controller 33. Lumen 61 permits optional sensors 42, 43 or electrodes to communicate with data transfer circuit 38, and optional lumen 62 for delivering a pharmacological agent (e.g., a drug) to the heart.

In operation, catheter 31 with flow limiting element 32/50 is inserted into the patient's subclavian vein and guided to the SVC of the patient, e.g., to a position proximal of the entrance to the right atrium (see FIG. 1A). Techniques known in the art can be used to insert and fix flow limiting element 32/50 at the desired venous location in the patient. Proper localization of the device may be confirmed using, for example, vascular ultrasound. Alternatively, flow limiting element 32/50 may be inserted through the jugular vein or even a peripheral vein and guided to the SVC under fluoroscopic or ultrasound guidance.

Once catheter 31 and flow limiting element 32/50 are positioned at the desired locations, controller 33 initiates a process in which the occlusion element is expanded and contracted such that blood flow in the SVC is intermittently occludes and resumed. The extent to which the flow limiting element impedes blood flow can be regulated by adjusting the degree to which the flow limiting element expands radially, and also for time interval for the occlusion, e.g., over how many heart beats. For example, in some embodiments the flow limiting element may impede blood flow in the SVC by anywhere from at least 50% up to 100%. Impedance of blood flow may be confirmed using methods known in the art, e.g., by measuring reductions in pressure, reductions in pressure fluctuations, or visually using ultrasound.

In accordance with one aspect of the disclosure, controller 33 includes software stored in memory 41 that controls the timing and duration of the successive expansions and contractions of flow limiting element 32/50. As described above, the programmed routines run by processor 37 may use as an input the patient's cardiac cycle. For example, in some embodiments, the software may be configured to actuate flow limiting element 32/50 to maintain partial or complete occlusion of the SVC over multiple cardiac cycles, for example, four or more successive heart beats in the subject. Controller 33 may accept as input via data transfer circuit 38 an output of electrodes 44 representative of the patient's electrocardiogram (ECG), or alternatively may receive such an input wirelessly from a third-party heart rate application running on the patient's smartphone, such that the software running on processor 37 can adjust the interval and/or degree of the occlusion provided by system 30 responsive to the patient's heart rate. Thus, for example, if the patient is physically active, the timing or degree of occlusion caused by the flow limiting element may be reduced to permit faster replenishment of oxygenated blood to the patient's upper extremities. Conversely, if the heart rate indicates that the patient is inactive, the degree of occlusion of the SVC may be increased to reduce the resting workload on the heart. Alternatively, or in addition, system 30 may accept an input via data transfer circuit 38 a value, measured by optional sensors 42 and 43, or a third party application and device, such as a blood pressure cuff, representative of the patient's blood pressure, such that controller 33 regulates flow through the SVC responsive to the patient's blood pressure.

Controller 33 may be programmed to cause the flow limiting element to expand when a sensed parameter is outside a predetermined range and/or above or below a predetermined threshold. For example, controller 33 may cause the flow limiting element to expand when right atrium ("RA") pressure is sensed by optional sensors 42 and/or 43 to be within a predetermined range, e.g., 15 to 30 mmHg, 18 to 30 mmHg, 20 to 30 mmHg, 20 to 25 mmHg, or above a predetermined threshold, e.g., 15 mmHg, 18 mmHg, 20 mmHg, 22 mmHg, 25 mmHg, 30 mmHg. As another example, controller 33 may cause the flow limiting element to expand when the mean pulmonary artery ("PA") pressure is sensed by optional sensors 42 and/or 43 to be within a predetermined range, e.g., 15 to 30 mmHg, 18 to 30 mmHg, 20 to 30 mmHg, 20 to 25 mmHg, or above a predetermined threshold e.g., 15 mmHg, 18 mmHg, 20 mmHg, 22 mmHg, 25 mmHg, 30 mmHg. The predetermined range and/or the predetermined threshold may be patient specific and controller 33 may be programmed and reprogrammed for individual patients.

Referring now to FIGS. 8-10, alternative forms of intravenous flow limiting elements suitable for use to occlude the SVC are described. As will be apparent to one skilled in the art, while FIGS. 4-6 depict a cylindrical flow limiting element, other shapes may be used. In addition, while not illustrated with anchoring members in FIGS. 8-10, anchoring members may be included. In each pair of drawings, 8A, 8B, 9A, 9B and 10A, 10B, the pair-wise drawings depict that each flow limiting element has a collapsed contracted state (FIGS. 8A, 9A and 10A), where the flow limiting element does not significantly impede blood flow, and an expanded deployed state (FIGS. 8B, 9B and 10B), in which the flow limiting element partially of fully occludes blood flow through the SVC.

In particular, referring to FIGS. 8A and 8B, catheter 70 includes balloon 71 attached to distal end 72. Balloon 71 is illustrated as having a rounded ball shape.

Referring now to FIGS. 9A and 9B, catheter 80 includes flow limiting element 81 comprising spring-loaded plug 82 formed of a biocompatible material (e.g., beryllium) and having a tapered conical shape. Spring-loaded plug 82 is captured in its collapsed contracted state within sheath 83 disposed at distal end 84 of catheter 80. More particularly, a vertex of conically-shaped plug 82 is positioned adjacent the proximal end 85 of sheath 83. During delivery of catheter 80, spring-loaded plug 82 is captured within sheath 83 in its low-profile state to allow blood flow in the SVC. To expand spring-loaded plug 82, force is applied via actuation wire 86 to withdraw plug 82 from sheath 83. As for the previous embodiments, plug 82 is biased to return within sheath 83 when the proximal force is removed from the proximal end of actuation wire 86, so that the flow limiting element 81 remains in its collapsed contracted state if disconnected from controller 33.

Referring to FIGS. 10A and 10B, catheter 90 depicts a further alternative embodiment of occlusive device 91, which takes the form of spring-loaded plug 92. Spring-loaded plug 92 is similar to plug 82 of FIGS. 9A and 9B, and has a tapered conical shape and is loaded within sheath 93 disposed at distal end of catheter 90. In response to a distally-directed force applied by drive mechanism 36 to the proximal end of catheter 90, spring-loaded plug 92 is pushed out of distal end of sheath 94 and expands to occlude the SVC. When the distally-directed force is removed, spring-loaded plug 92 retracts to its collapsed contracted state within sheath 94, thereby permitting blood to flow substantially unimpeded through the SVC.

Applicants have observed that animal testing indicates that a system constructed and operated in accordance with the methods of the present SVC occlusion system provides significant benefits over previously-known IVC systems for treating heart failure. Preliminary animal testing conducted on swine models one week post myocardial infarction is described below.

Figure 11:
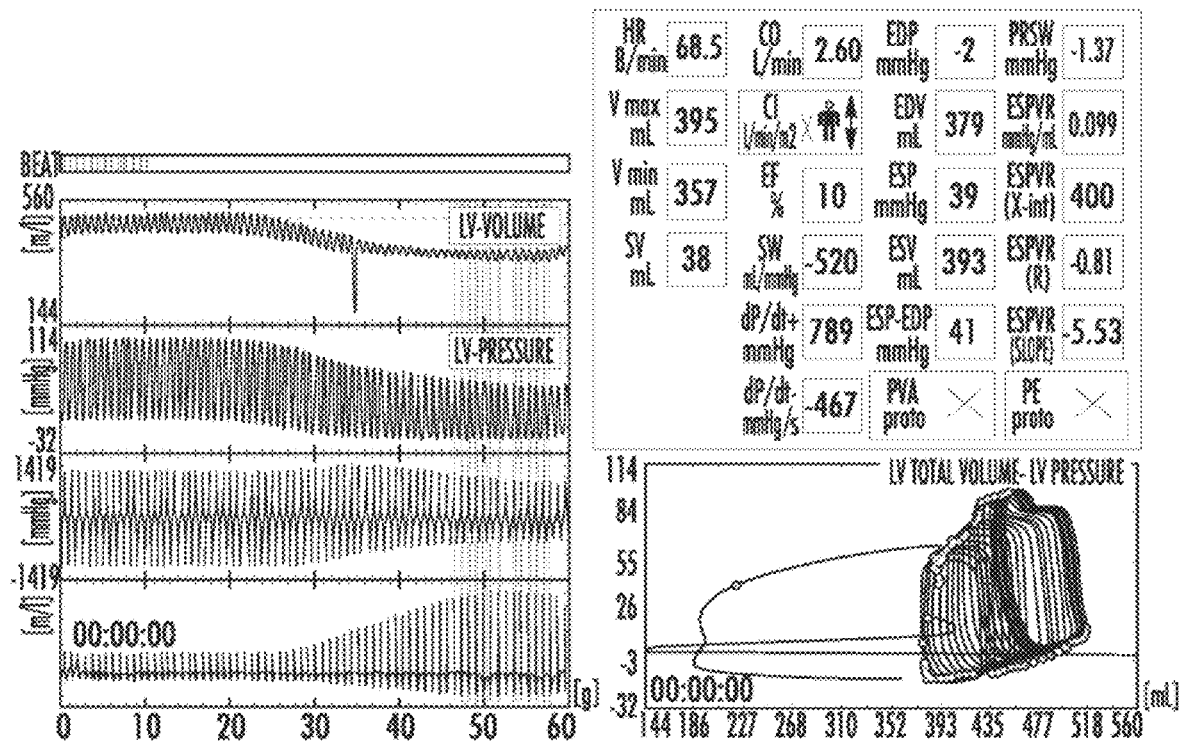
FIG. 11 shows graphs and a table showing left ventricle (LV) pressure and LV volume for a number of successive heart beats in a swine model following full occlusion of the inferior vena cava (IVC).

Referring to FIG. 11, changes in the LV pressure and LV volume are shown for a number of successive heart beats in a swine model following full occlusion of the inferior vena cava (IVC), as suggested in the foregoing published Cedeno patent application. In particular, the IVC was fully occluded for approximately 30 seconds during which the both left ventricular end diastolic pressure (corresponding to lower right-hand corner of the hysteresis loop) and left ventricular systolic pressure (corresponding to upper left-hand corner of the hysteresis loop) decreased during each successive heartbeat. LV pressure rapidly increased to pre-occlusion levels once the IVC occlusion was removed (i.e., similar to first half of the pressure and volume trace). Because IVC occlusion therapy proposed by Cedeno reduces systolic pressure, the therapy can lead to reduced ejection fraction during systole, with potentially dangerous consequences to the patient. In addition, occlusion of the IVC may result in congestion of the renal and hepatic veins, which could give rise to and exacerbate, rather than ameliorate, complications often associated with congestive heart failure.

Figure 12:
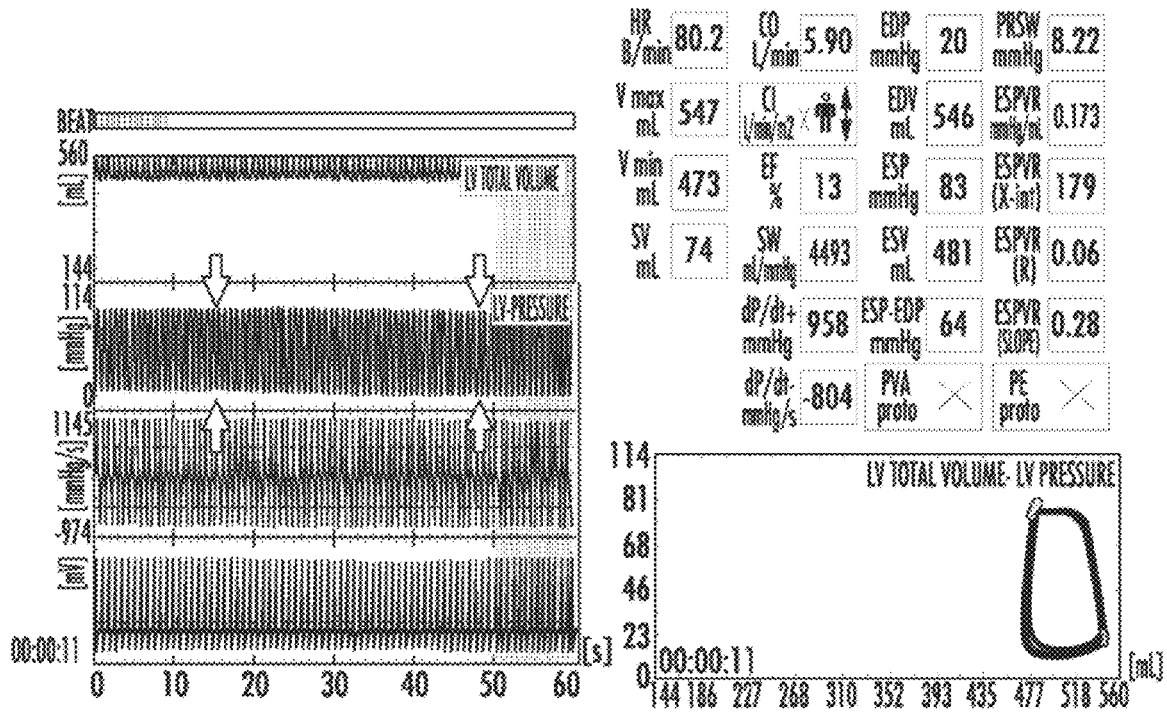
FIG. 12 shows graphs and a table showing LV pressure and LV volume for a number of successive heart beats in a swine model following partial occlusion of the superior vena cava (SVC).

Referring to FIG. 12, changes in the LV pressure and LV volume are shown for a number of successive heart beats in a swine model following partial occlusion of the superior vena cava (SVC), as described in accordance with the principles of the present invention. In particular, the SVC was partially occluded for approximately 30 seconds during which the left ventricular end diastolic pressure (corresponding to lower right-hand corner of the hysteresis loop) decreased while the left ventricular systolic pressure (corresponding to upper left-hand corner of the hysteresis loop) remained substantially unchanged during each successive heartbeat. LV pressure rapidly increased to pre-occlusion levels once the SVC occlusion was removed (i.e., similar to first half of the pressure and volume trace). Advantageously, the method of the present invention of partially occluding the SVC appears to have little or no impact on ejection fraction during systole, but reduces wall stress in the ventricles during diastole. Moreover, as discussed in more detail below, occlusion of the SVC will be tolerated well by the patient, will not contribute to congestion of the renal or hepatic veins, and will not exacerbate complications often associated with congestive heart failure including liver and kidney failure.

Figure 13:
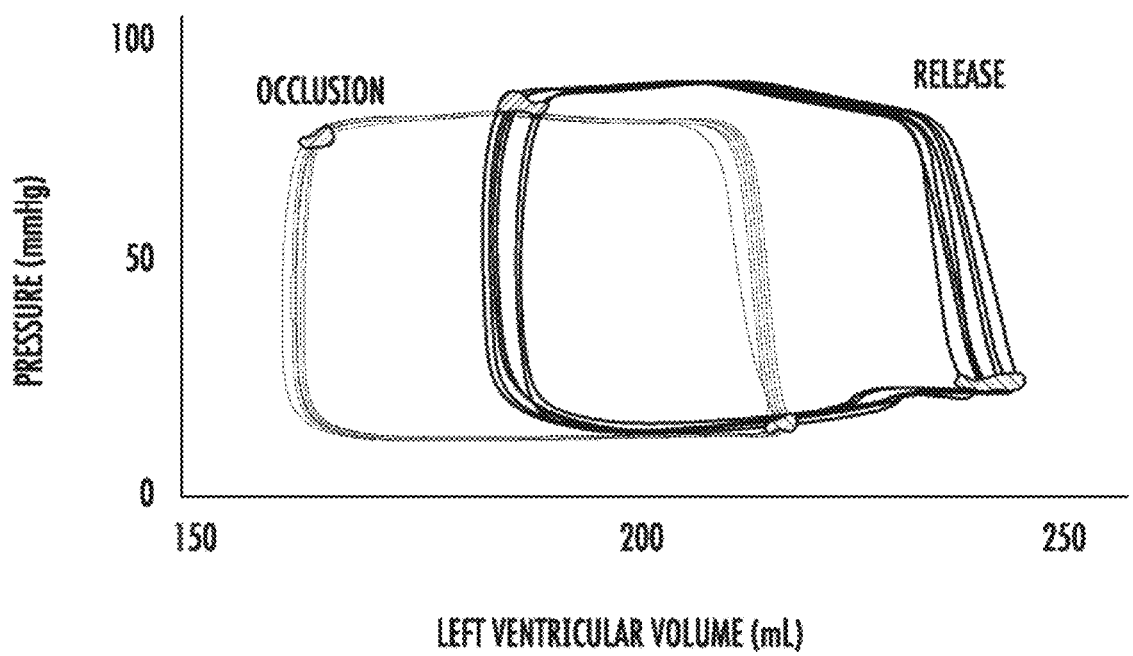
FIGS. 13-14 are graphs showing the changes in pressure as a function of left and right ventricular volume, respectively, during occlusion of the superior vena cava (SVC) and release in a swine subjected to heart failure in accordance with the principles of the present invention.
Figure 14:
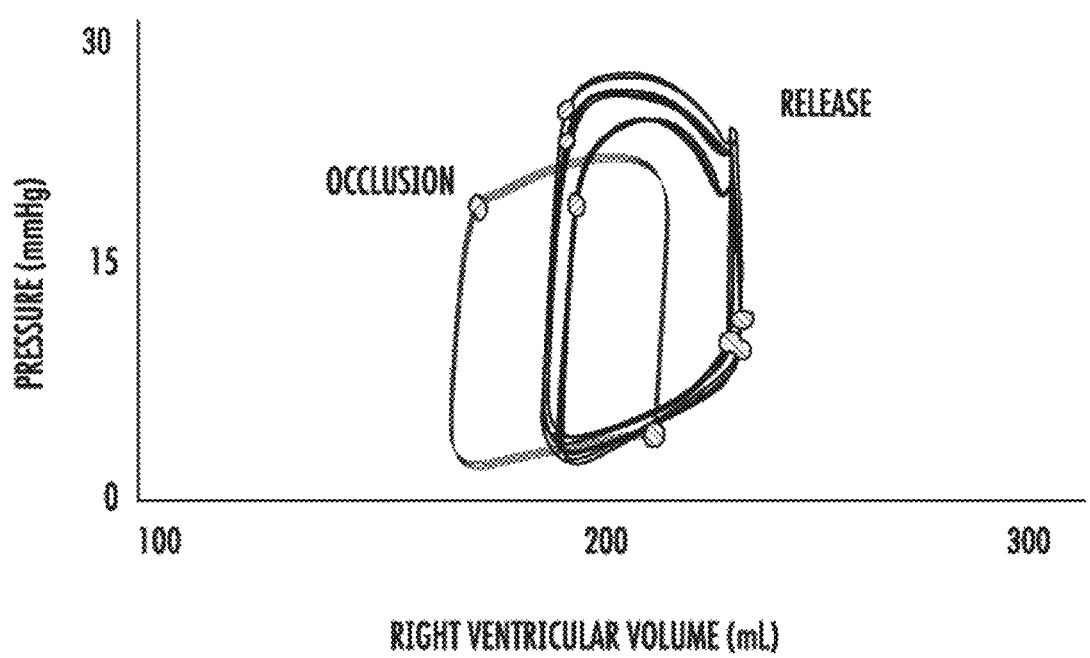

FIGS. 13-14 are graphs showing the changes in pressure as a function of left and right ventricular volume, respectively, during occlusion of the superior vena cava (SVC) and release in a swine treated for heart failure in accordance with the principles of the present invention. As shown in the graphs, SVC occlusion led to a significant reduction in left ventricular (LV) volume (240 to 220 mL) and a reduction in LV diastolic pressure (25 to 10 mmHg). SVC occlusion also was associated with reduction in LV systolic pressure (94 to 90 mmHg). SVC occlusion also decreased right ventricular (RV) volume (230 to 210 mL), diastolic pressure (12 to 4 mmHg), and RV systolic pressure (27 to 16 mmHg). Advantageously, SVC occlusion in accordance with the systems and methods described herein reduces biventricular volume and diastolic (filling) pressures without negatively impacting systemic blood pressure (LV systolic pressure). These findings suggest that SVC occlusion has a potentially important beneficial effect on biventricular interaction such that reducing diastolic filling pressures in both ventricles allows for increased ventricular compliance, thereby improving ventricular filling and resulting in increased stroke volume and cardiac output, which is the primary objective when treating a patient with heart failure.

FIG. 15 includes graphs showing that superior vena cava (SVC) occlusion in accordance with the principles of the present invention on a swine subject improves cardiac function. The graphs each show the results for partial inferior vena cava (IVC) occlusion (left side of each graph) versus full SVC occlusion (right side of each graph). The graphs show measured left ventricle (LV) stroke volume, cardiac output, LV contractility, LV diastolic pressure, LV systolic pressure, and end-systolic volume.

Figure 16:
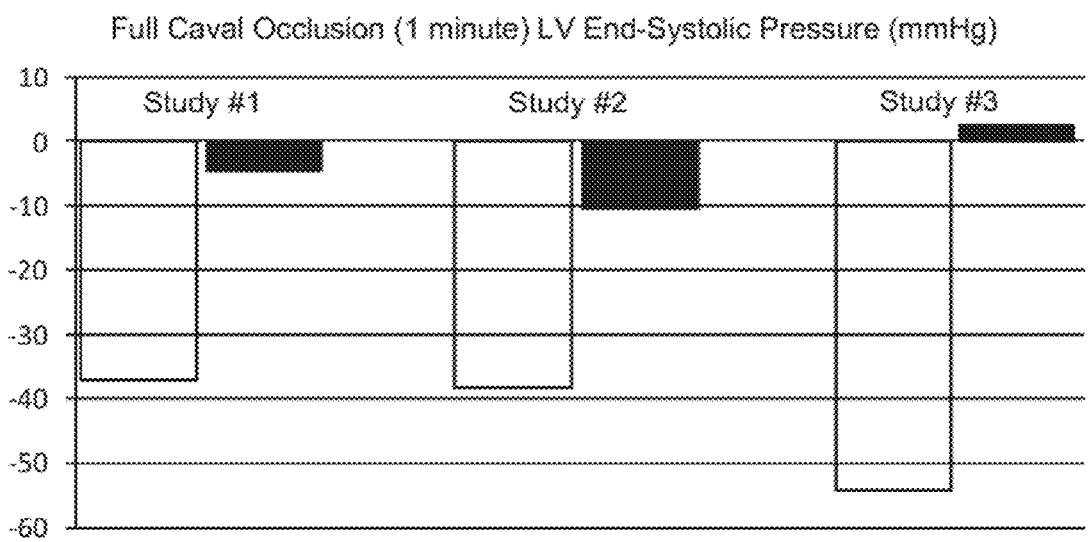

FIG. 16 is graph showing that SVC occlusion in accordance with the principles of the present invention on three swine subjects does not harm systolic blood pressure. The graph shows the full caval occlusion (1 minute) LV end systolic pressure (mmHg) for full IVC occlusion (left side of each study) versus full SVC occlusion (right column of each study). Less reduction in LV-end-systolic pressure with SVC occlusion compared to IVC occlusion.

Figure 17:
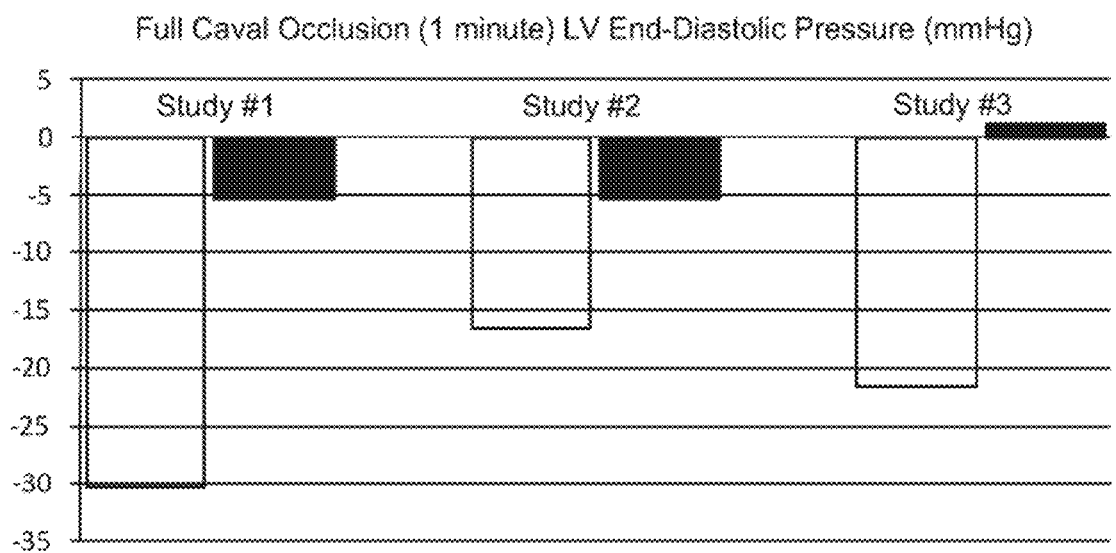

FIG. 17 is graph showing that SVC occlusion in accordance with the principles of the present invention on three swine subjects does not harm LV diastolic filling. The graph shows the full caval occlusion (1 minute) LV end diastolic pressure (mmHg) for full IVC occlusion (left side of each study) versus full SVC occlusion (right side of each study). Less reduction in LV-end-diastolic pressure with SVC occlusion compared to IVC occlusion.

Figure 18:
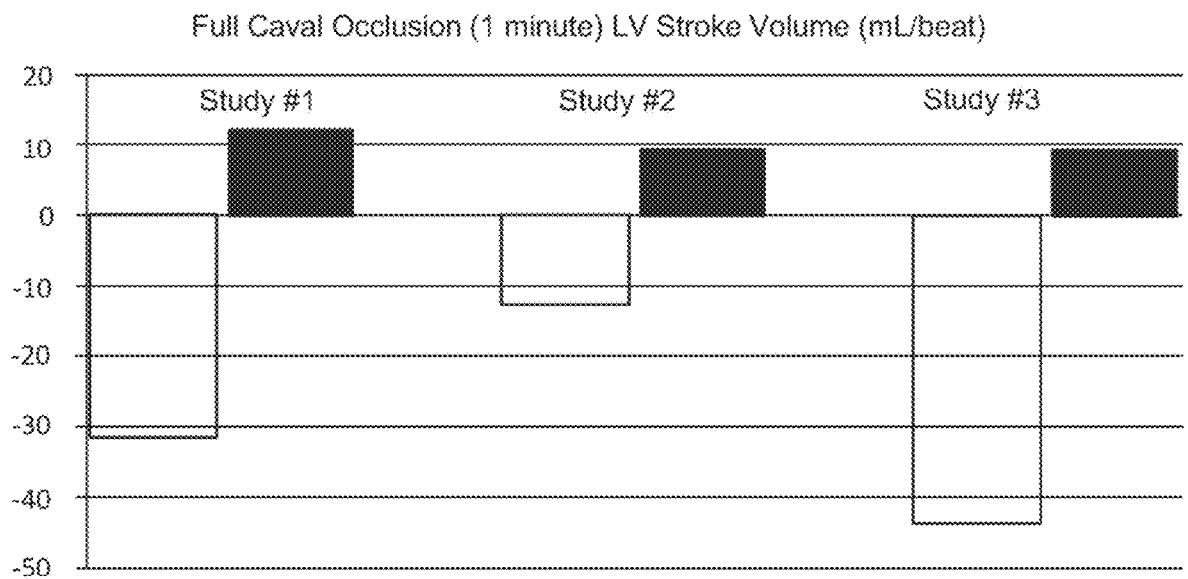

FIG. 18 is graph showing that SVC occlusion in accordance with the principles of the present invention on three swine subjects improves LV stroke volume. The graph shows the full caval occlusion (1 minute) LV stroke volume (mL/beat) for full IVC occlusion (left side of each study) versus full SVC occlusion (right side of each study). Increased LV stroke volume with SVC occlusion compared to reduced LV stroke volume IVC occlusion.

Figure 19:
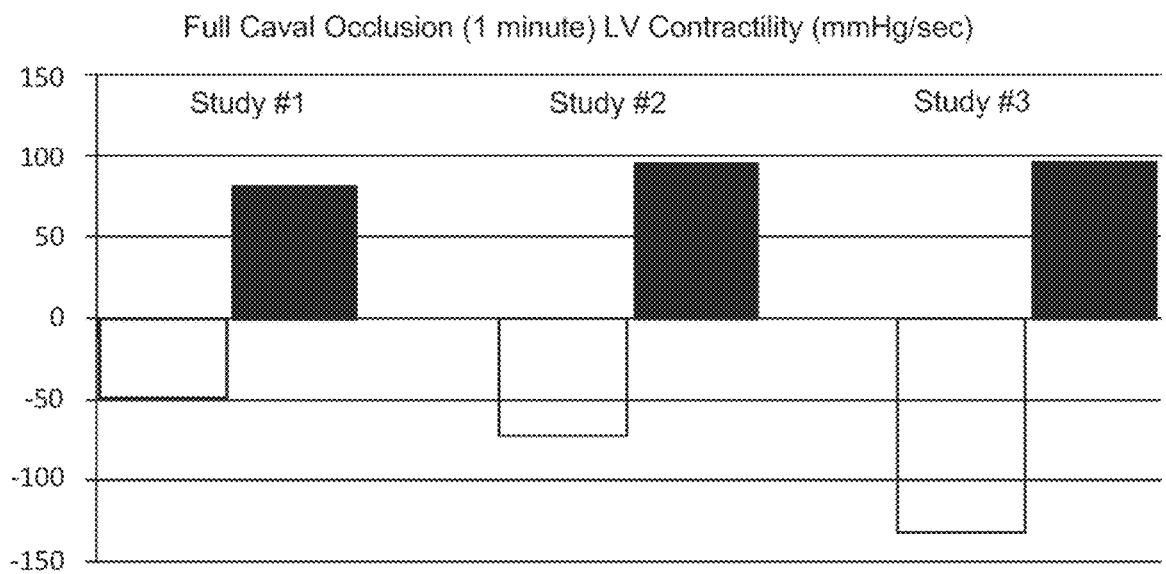

FIG. 19 is graph showing that SVC occlusion in accordance with the principles of the present invention on three swine subjects improves LV contractility. The graph shows the full caval occlusion (1 minute) LV contractility (mmHg/sec) for full IVC occlusion (left side of each study) versus full SVC occlusion (right side of each study). Increased LV contractility with SVC occlusion compared to reduced LV contractility with IVC occlusion.

Figure 20:
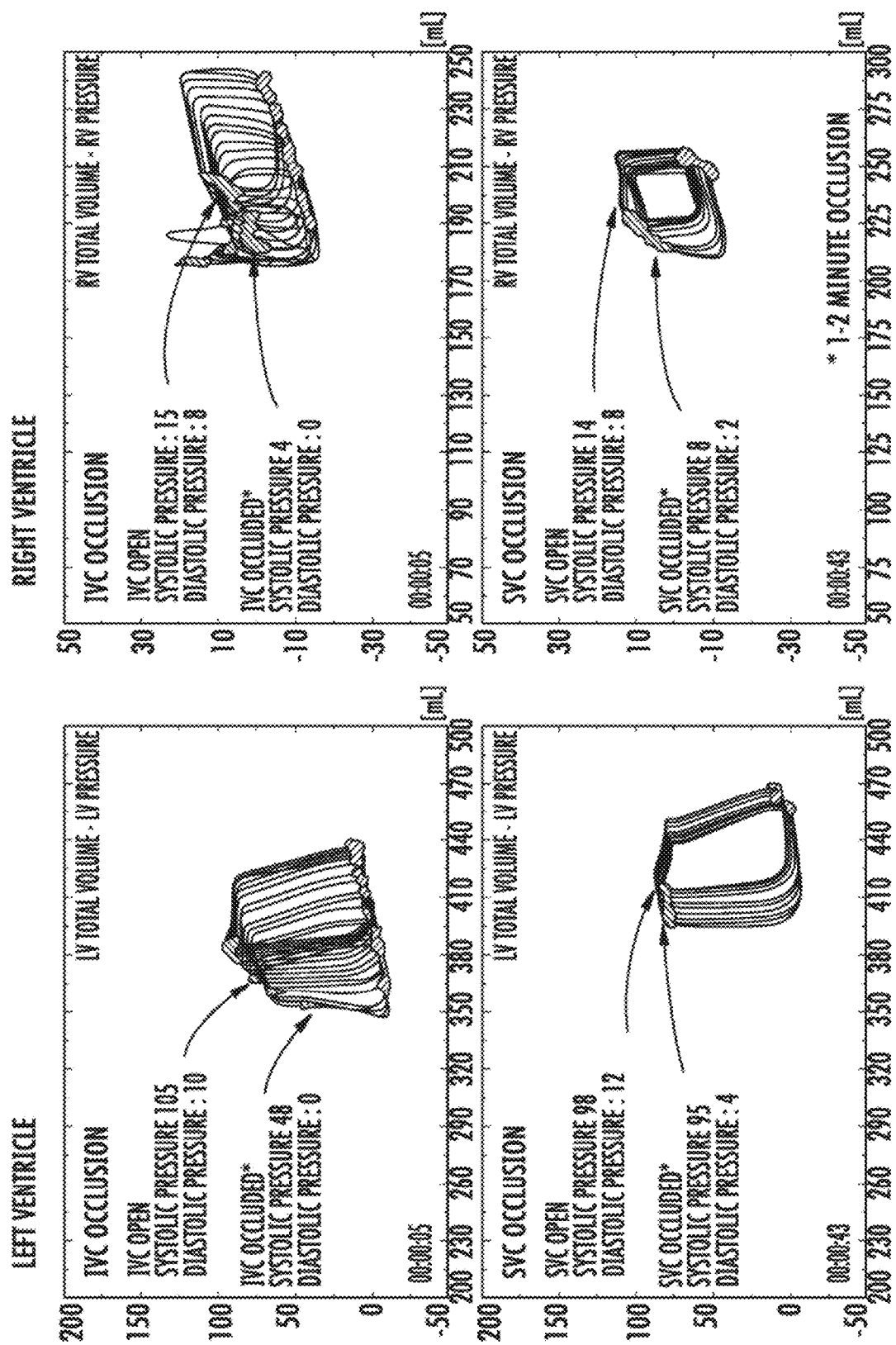

FIG. 20 is four graphs depicting LV total volume and LV pressure for IVC occlusion (upper left), RV total volume and RV pressure for IVC occlusion (upper right), LV total volume and LV pressure for SVC occlusion (lower left), and RV total volume and RV pressure for SVC occlusion (lower right). FIG. 20 illustrates that SVC occlusion provides a significant reduction in LV and RV diastolic pressures without a major reduction in LV systolic pressure as compared to IVC occlusion.

Figure 21:
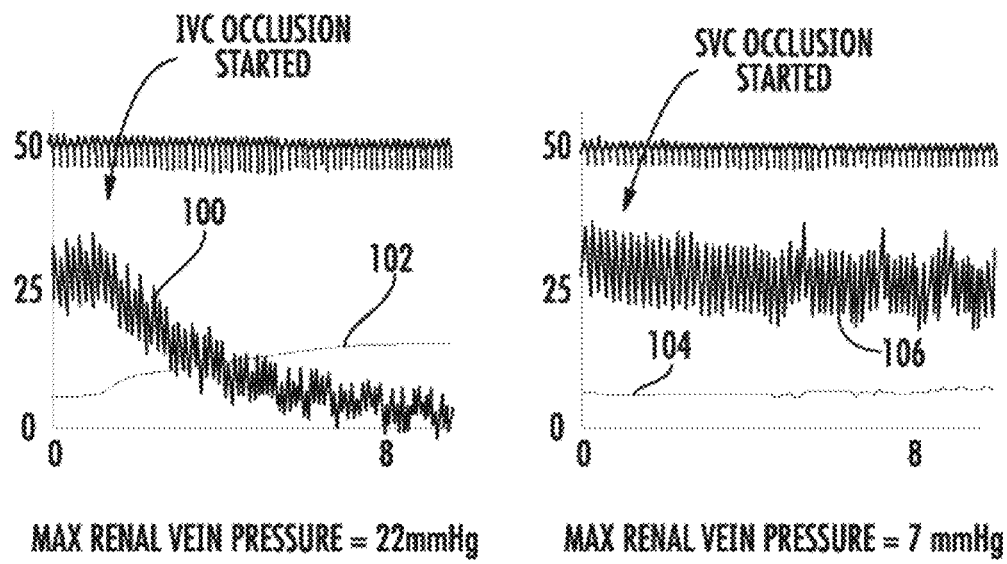

FIG. 21 includes two graphs depicting measured pulmonary artery pressure and renal vein pressure in a swine subject for IVC occlusion (left graph) and SVC occlusion (right graph). Line 100 shows the measured pulmonary artery pressure while line 102 shows the measured renal vein pressure for IVC occlusion. Line 104 shows the measured pulmonary artery pressure while line 106 shows the measured renal vein pressure for SVC occlusion. The max renal vein pressure is measured to be 22 mmHg for IVC occlusion whereas the max renal vein pressure is measured to be 7 mmHg for SVC occlusion. FIG. 21 demonstrates that SVC occlusion reduces pulmonary artery pressures without increasing renal vein pressure as compared to IVC occlusion.

Figure 22:
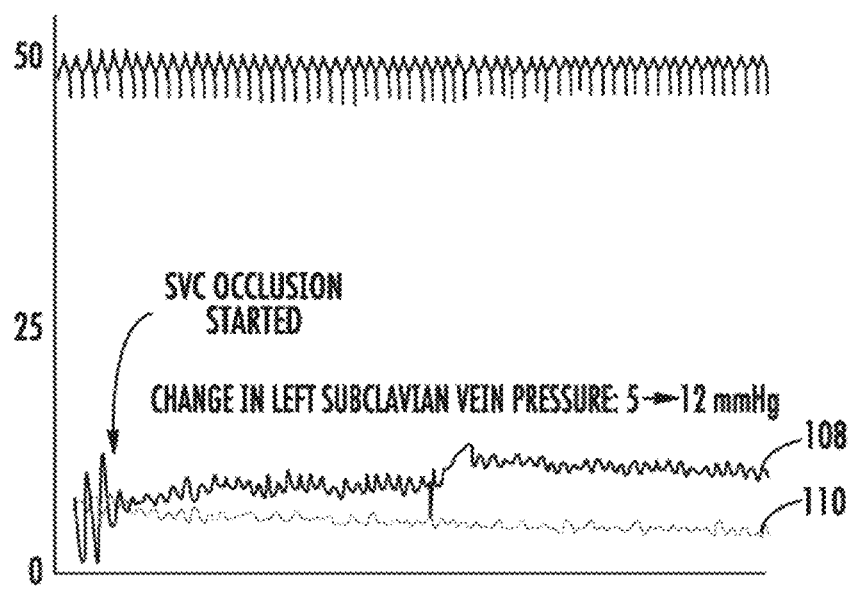
Figure 23A:
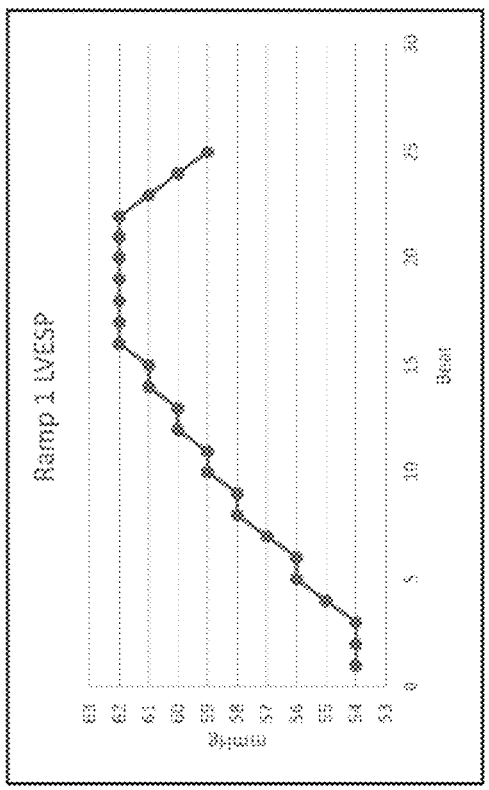
FIGS. 23A to 23D illustrate, respectively, clinical pressure changes in left ventricular end diastolic pressure, left ventricular end systolic pressure, left ventricular volume and ventricular stroke work during the deflation time of a one minute episode of continuous SVC occlusion in accordance with the principles of the present invention.
Figure 23B:
Figure 23C:
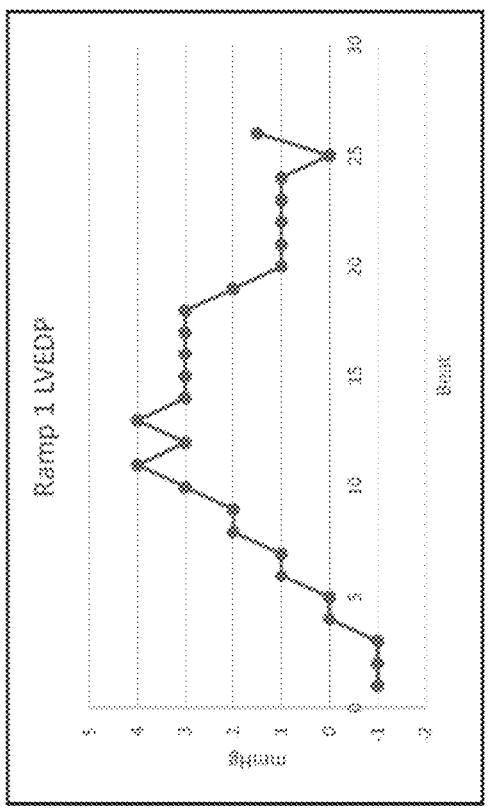
Figure 23D:
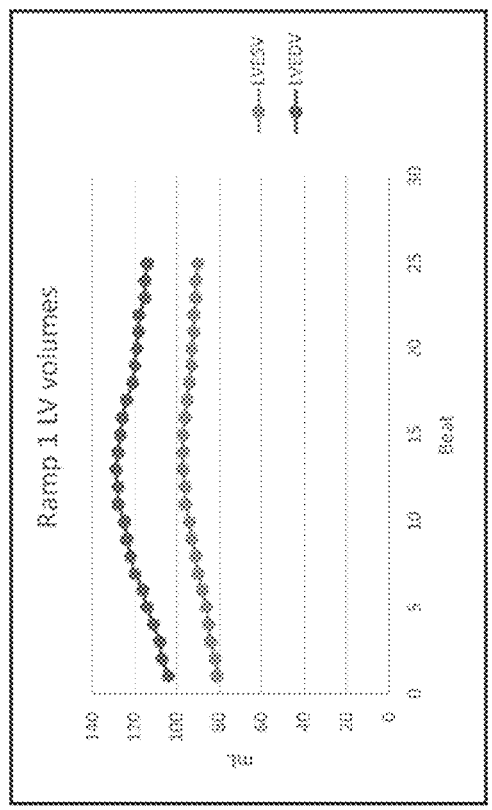
Figure 24A:
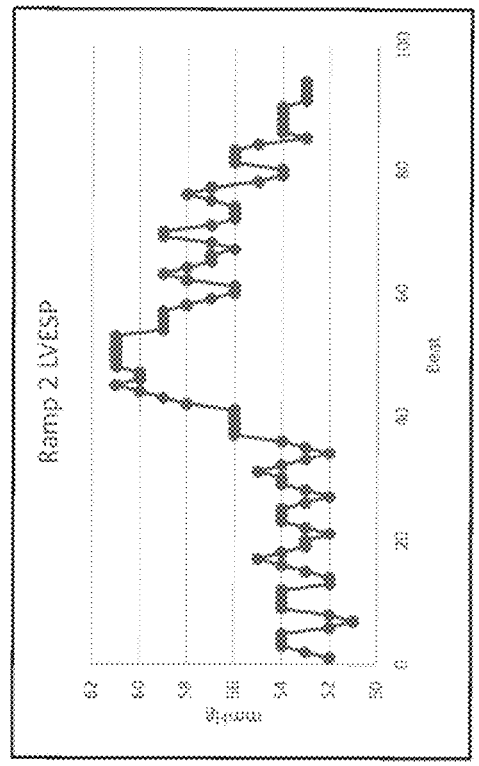
FIGS. 24A to 24D illustrate, respectively, clinical pressure changes in left ventricular end diastolic pressure, left ventricular end systolic pressure, left ventricular volume and ventricular stroke work during the deflation time of a five minute episode of continuous SVC occlusion in accordance with the principles of the present invention.
Figure 24B:
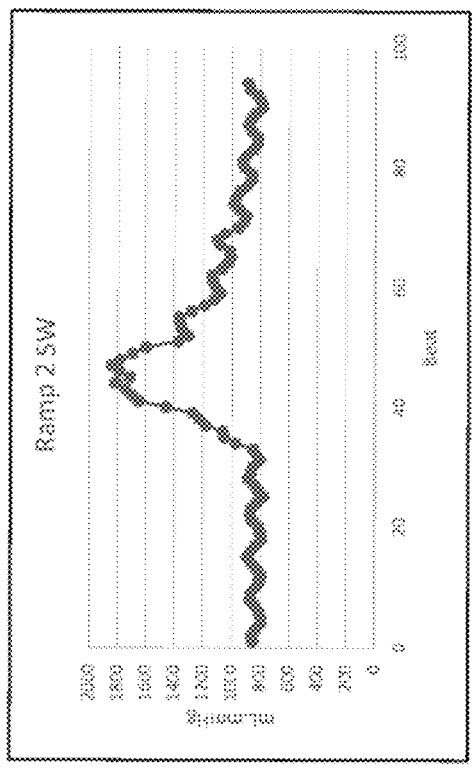
Figure 24C:
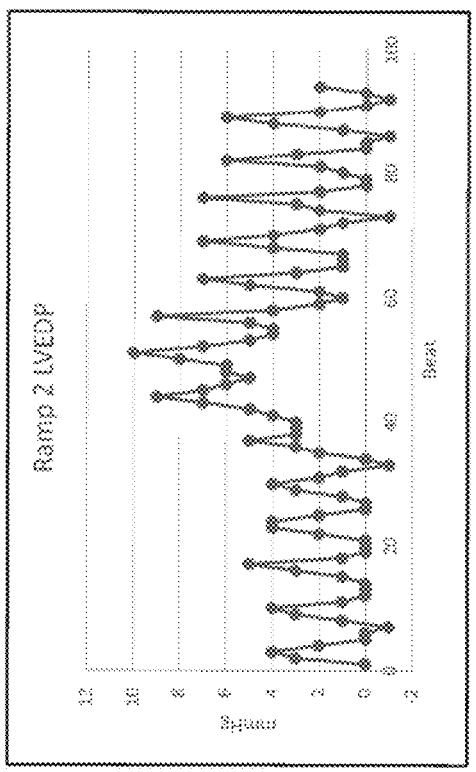
Figure 24D:
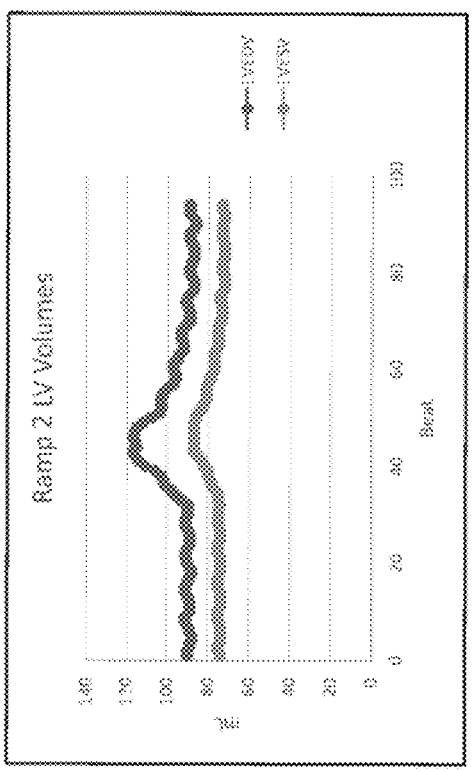
Figure 25B:
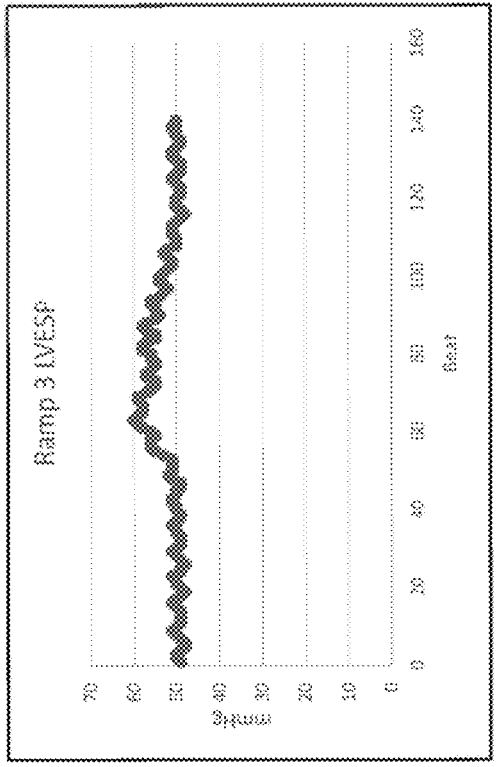
FIGS. 25A to 25D illustrate, respectively, clinical pressure changes in left ventricular end diastolic pressure, left ventricular end systolic pressure, left ventricular volume and ventricular stroke work during the deflation time of a ten minute episode of continuous SVC occlusion in accordance with the principles of the present invention.
Figure 25D:
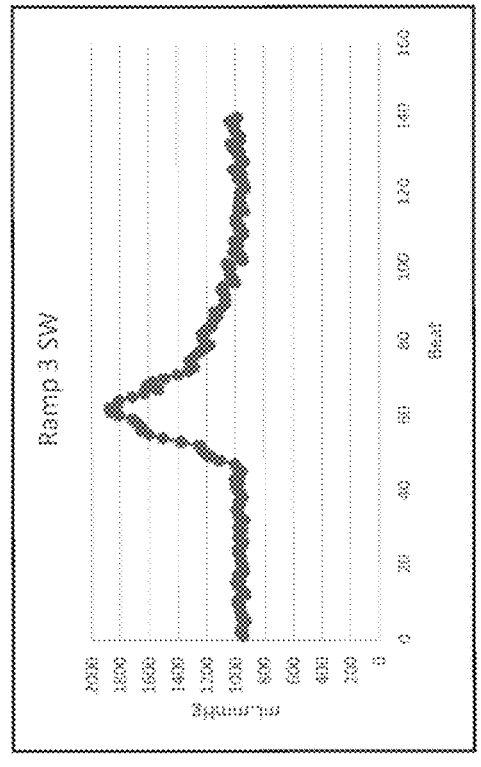
Figure 25A:
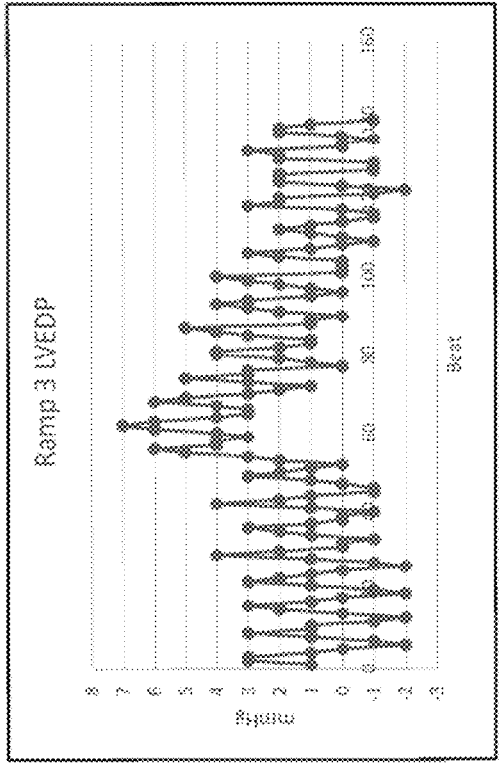
Figure 25C:
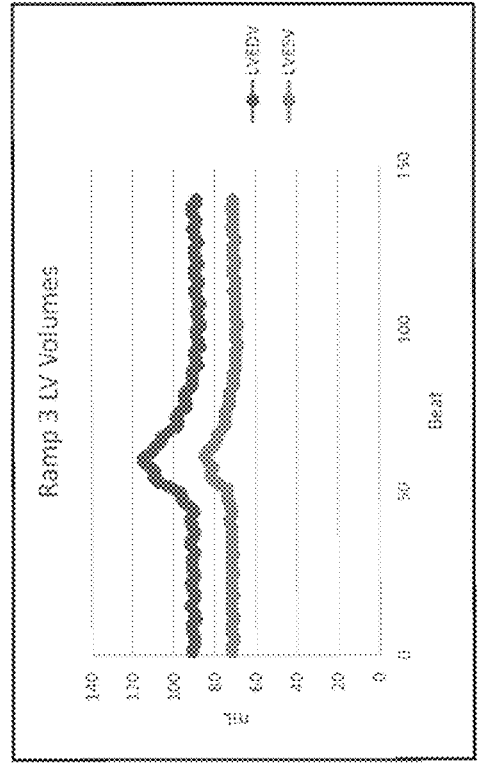

FIG. 22 is a graph depicting measured left subclavian vein pressure and renal vein pressure in a swine subjected to SVC occlusion in accordance with the principles of the present invention. Line 108 shows the measured left subclavian vein pressure while line 110 shows the measured renal vein pressure for SVC occlusion. The measured change in left subclavian vein pressure is 5 to 12 mmHg during SVC occlusion. FIG. 22 demonstrates that proximal left subclavian vein pressure increases nominally during SVC occlusion.

Results of additional animal testing conducted on swine models over various occlusion periods are shown in FIGS. 23A-26C. Referring now to FIGS. 23A to 23D, clinical pressure changes in left ventricular end diastolic pressure, left ventricular end systolic pressure, left ventricular volume and ventricular stroke work, respectively, during the deflation time of a one-minute episode of continuous SVC occlusion in a pig model are depicted. Specifically, the controller was programmed to cause the flow limiting element to at least partially occlude the SVC for one minute, and then contract, e.g., deflate, for one second. As shown in FIGS. 23A to 23D, one-minute SVC occlusion may not be sufficient to result in a steady-state reduction in ventricular volumes after the deflation time.

Referring now to FIGS. 24A to 24D, clinical pressure changes in left ventricular end diastolic pressure, left ventricular end systolic pressure, left ventricular volume and ventricular stroke work, respectively, during the deflation time of a five minute episode of continuous SVC occlusion in a pig model are depicted. Specifically, the controller was programmed to cause the flow limiting element to at least partially occlude the SVC for five minutes, and then contract, e.g., deflate, for one second. As shown in FIGS. 24A to 24D, ventricular volumes reached a clear steady-state reduction after the deflation time as a result of five-minute SVC occlusion.

Referring now to FIGS. 25A to 25D, clinical pressure changes in left ventricular end diastolic pressure, left ventricular end systolic pressure, left ventricular volume and ventricular stroke work, respectively, during the deflation time of a ten minute episode of continuous SVC occlusion in a pig model are depicted. Specifically, the controller was programmed to cause the flow limiting element to at least partially occlude the SVC for ten minutes, and then contract, e.g., deflate, for one second. By a comparison of FIGS. 25A to 25D with FIGS. 24A to 24D, the advantage of ten-minute SVC occlusion over five-minute SVC occlusion is not significant in this model. Accordingly, in consideration of patient safety, five-minute SVC occlusion was used during initial clinical studies such as the Tufts IRB-approved protocol described below with reference to FIGS. 26A to 26C, though ten-minute occlusion in a human subject is described in more detail below with respect to FIGS. 28A-B.

Figure 26A:
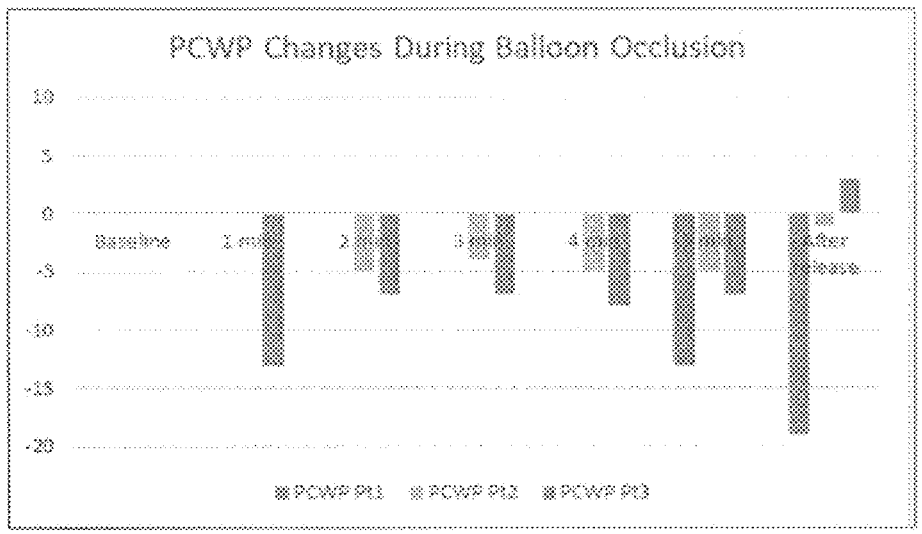
FIGS. 26A to 26C illustrate, respectively, clinical pressure changes in pulmonary capillary wedge pressure, pulmonary artery pressure and right atrial pressure observed during a five minute episode of continuous SVC occlusion in accordance with the principles of the present invention.
Figure 26B:
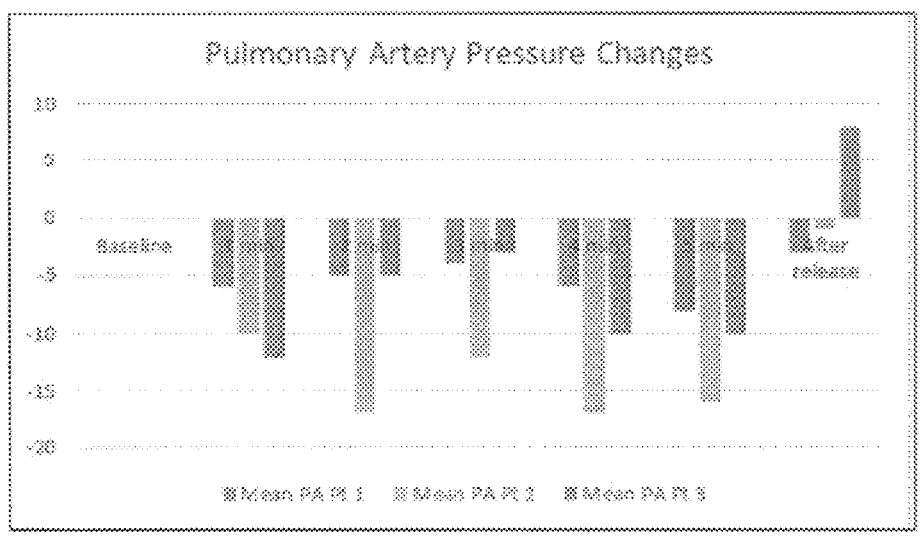
Figure 26C:
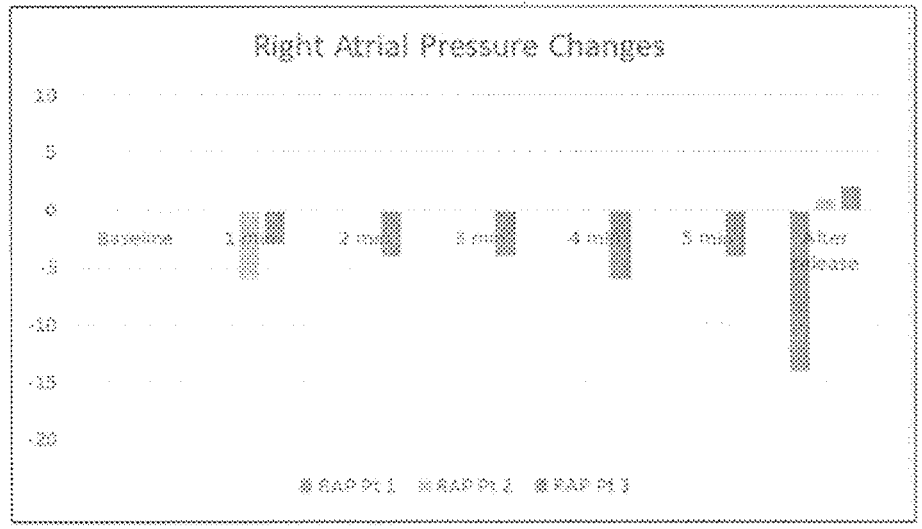

Encouraged by animal testing, Applicants conducted preliminary human testing and observed that a system constructed and operated in accordance with the methods of the present SVC occlusion system provides significant benefits. FIGS. 26A to 26C depict clinical pressure changes observed during a five-minute episode of continuous SVC occlusion for three human patients enrolled in a Tufts IRB-approved protocol. Specifically, the three patients underwent five minutes of continuous SVC occlusion with acute neuro and cardiac monitoring and thirty-day neuro assessment (Table 1).

TABLE 1

| Baseline Parameters | Baseline Parameters | | |
|---|---|---|---|
| | Patient # 1 | Patient # 2 | Patient # 3 |
| Mean Right Atrial Pressure | 30 | 21 | 18 |
| Mean Pulmonary Artery Pressure | 52 | 44 | 28 |
| Pulmonary Capillary Wedge Pressure | 50 | 20 | 23 |
| PCPW - RAP Pressure Difference | 20 | −1 | 5 |
| LV Ejection Fraction | 10-15% | 35% | 25% |
| Systolic Pressure | 130 | 128 | 135 |

TABLE 1-continued

| | Baseline Parameters | | |
|---|---|---|---|
| Baseline Parameters | Patient # 1 | Patient # 2 | Patient # 3 |
| Diastolic Pressure | 97 | 72 | 84 |
| Mean Arterial Pressure | 108 | 90 | 100 |
| Cardiac Output | 2.6 | 4.4 | 3.9 |
| Heart Rate | 73 | 83 | 60 |
| NYHA Class | 4 | 4 | 2 |
| Overload Status | severe | severe | moderate |

As may be observed from FIGS. 26A to 26C and in Table 1, pulmonary capillary wedge pressure (PCWP), pulmonary artery pressure, and right atrial pressure changed significantly during the five minute episode of SVC occlusion, and had residual effect after release of the balloon. As a result of the study, all patients benefitted hemodynamically as there was a drop in all filling pressures, e.g., capillary wedge pressure (CWP) and mean pulmonary artery (PA) pressure. It was observed that the more congested patients experienced an increase in mean arterial pressure (MAP). The net effect of these hemodynamic changes is a reduction in cardio-pulmonary pressures and an increase in systemic pressures perfusing vital organs including the kidneys.

Encouraged by the foregoing preliminary swine and human results, Applicants performed additional testing on the three patients that were the subject of the testing discussed above with respect to FIGS. 26A-26C in addition to two new patients. The five human patients, each with heart failure, were subjected to the SVC occlusion system described above. Specifically, the five patients underwent five minutes of continuous SVC occlusion. The baseline parameters of the five patients are shown in Table 2 below. The third patient's New York Heart Association (NYHA) functional classification of 2 was the lowest. The results of the third patient suggest that application of the SVC occlusion system may preferably be used in patients with a NYHA functional classification of heart failure at level 3 and above.

TABLE 2

| | Baseline Parameters | | | | |
|---|---|---|---|---|---|
| | Pt #1 | Pt #2 | Pt #3 | Pt #4 | Pt #5 |
| Baseline Parameters | | | | | |
| Mean Right Atrial Pressure | 30 | 21 | 18 | 12 | 22 |
| Mean Pulmonary Artery Pressure | 52 | 44 | 28 | 52 | 35 |
| Pulmonary Capillary Wedge Pressure | 50 | 20 | 23 | 29 | 29 |
| PCWP - RAP Pressure Differential | 20 | −1 | 5 | 17 | 7 |
| LV Ejection Fraction | 10-15% | 35% | 25% | 20-25% | 20% |
| Systolic Pressure | 130 | 128 | 135 | 124 | 164 |
| Diastolic Pressure | 97 | 72 | 84 | 79 | 111 |
| Mean Arterial Pressure | 108 | 90 | 100 | 94 | 128 |
| Cardiac Output | 2.6 | 4.4 | 3.9 | 4.2 | 6.4 |
| Heart Rate | 73 | 83 | 60 | 92 | 89 |
| NYHA Class | 4 | 4 | 2 * | 3 | 3 |
| Overload status | severe | severe | moderate | not known | not known |

Figure 27A:
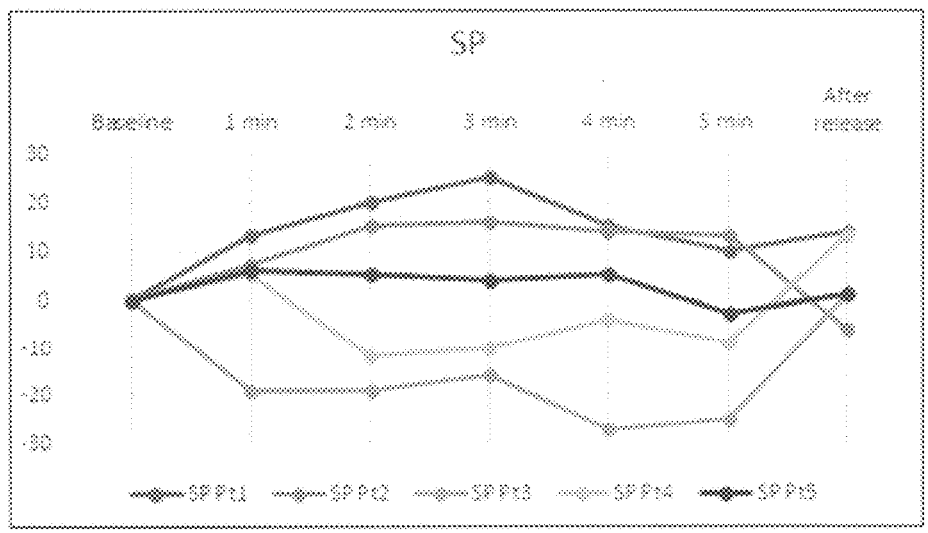
FIGS. 27A to 27E illustrate, respectively, clinical pressure changes in systolic pressure, diastolic pressure, mean arterial pressure, mean pulmonary artery pressure, and mean pulmonary capillary wedge pressure during five minutes of continuous SVC occlusion in accordance with the principles of the present invention.
Figure 27B:
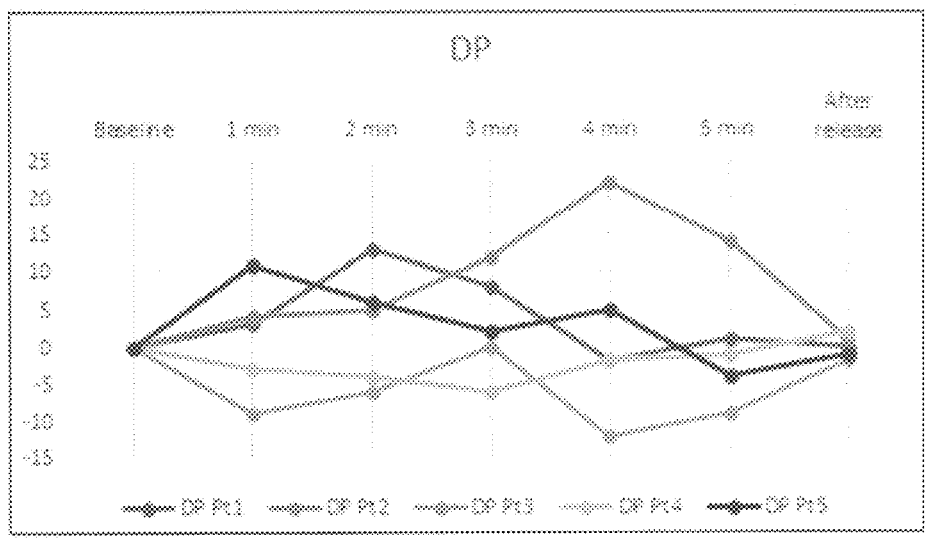
Figure 27C:
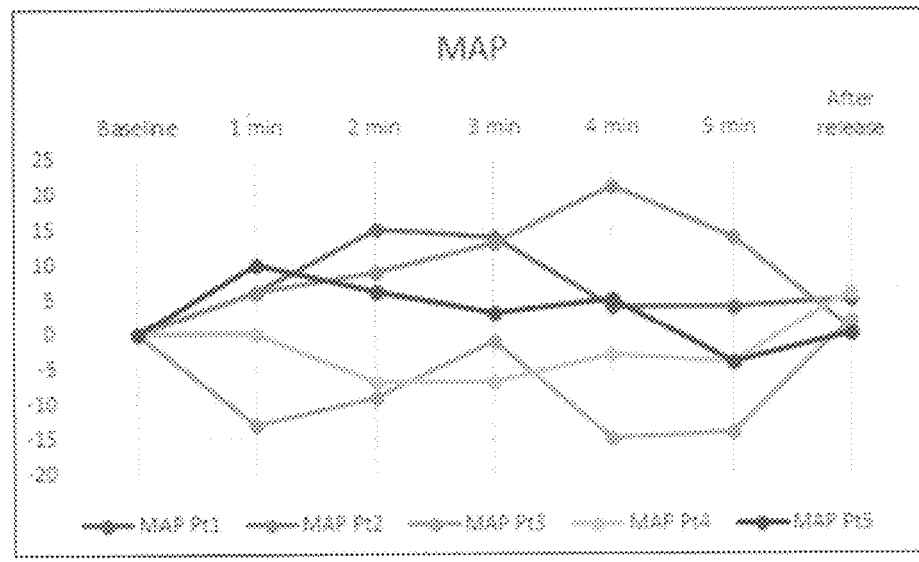
Figure 27D:
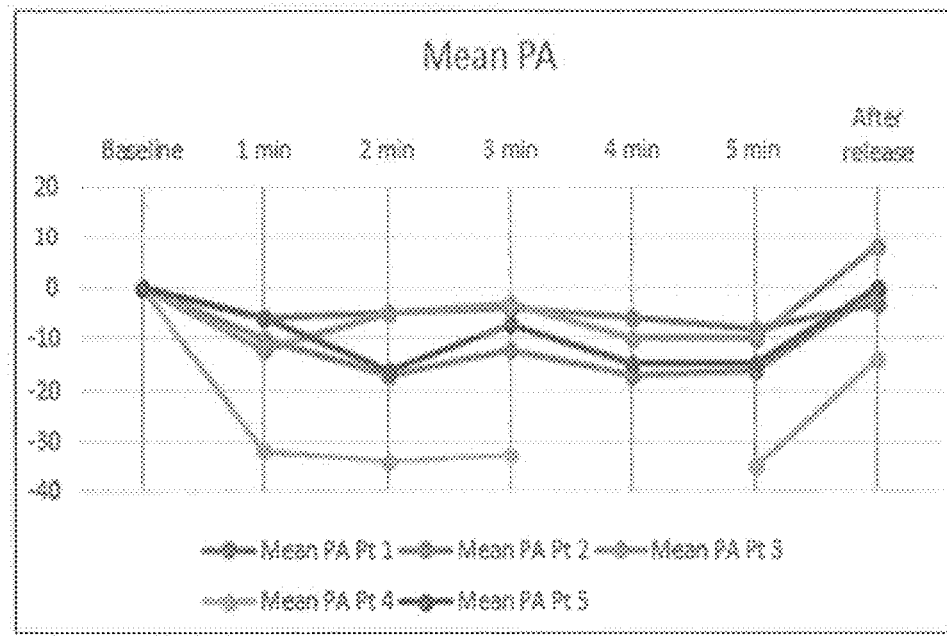
Figure 27E:
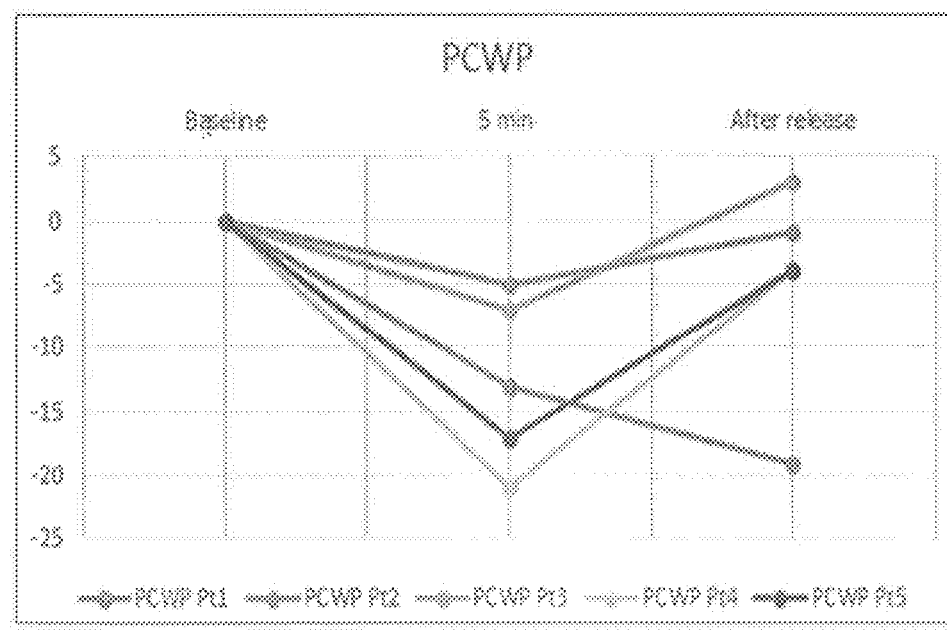

FIGS. 27A-27E illustrates the change in systolic pressure (SP), diastolic pressure (DP), mean arterial pressure (MAP), mean pulmonary artery (MPA) pressure, and pulmonary capillary wedge pressure (PCWP) from a baseline measurement for each of the five patients during and after occlusion. In FIGS. 27A-27D, the change in systolic pressure (SP), diastolic pressure (DP), mean arterial pressure (MAP), and mean pulmonary artery (MPA) pressure is shown every minute during the five minutes of occlusion. In FIG. 27E, the change in pulmonary capillary wedge pressure (PCWP) is shown at five minutes of occlusion and after occlusion.

The change in systolic pressure is illustrated in FIG. 27A. As is shown in FIG. 27A, the first, second and fifth patients generally experienced an increase in SP during occlusion, while the third and fourth patients generally experienced a decrease in systolic pressure. The change in diastolic pressure is illustrated in FIG. 27B. As is shown in FIG. 27B, the diastolic pressures during SVC occlusion generally increased for patients one, two and five and generally decreased for patients three and four.

The change in mean arterial pressure is illustrated in FIG. 27C. As is shown in FIG. 27C, the mean arterial pressure generally increased during SVC occlusion for patients one, two and five, and generally decreased for patients three and four. The change in mean pulmonary artery pressure is illustrated in FIG. 27D. As is shown in FIG. 27D, the mean pulmonary artery pressure decreased during SVC occlusion for each patient, though it should be noted that the there is no data point for the fourth patient at the fourth minute. The change in pulmonary capillary wedge pressure (PCWP) is illustrated in FIG. 27E at five minutes and after release. As is shown in FIG. 27E, the pulmonary capillary wedge pressure decreased for all patients at five minutes of SVC occlusion, indicating a drop-in filling pressures for each patient during occlusion.

As was observed in the study discussed with respect to FIGS. 26A-26C, the study illustrated in FIGS. 27A-27E indicated that all five patients benefitted hemodynamically as there was a drop in filling pressures, e.g., capillary wedge pressure (CWP) and mean pulmonary artery (PA) pressure and further, like the study discussed above with respect to FIGS. 26A-26C, the more congested patients generally experienced an increase in mean arterial pressure (MAP). Also, in many cases, at least some of the patients had residual effects after release of the occluder.

Figure 28A:
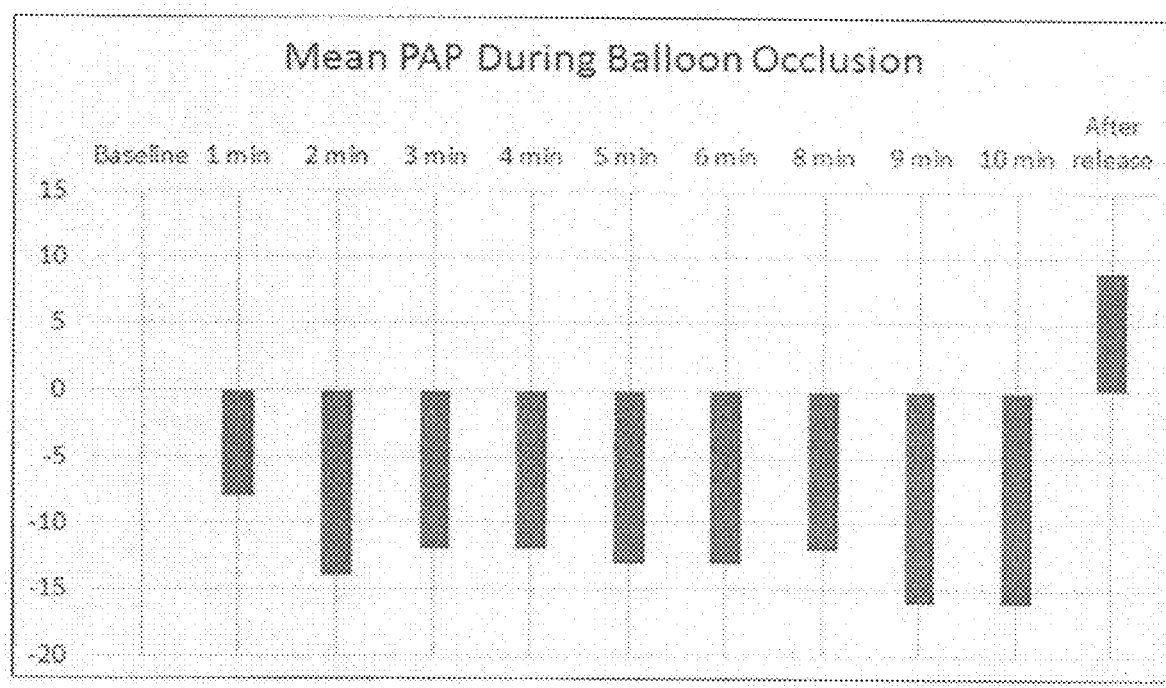
FIGS. 28A to 28B illustrate, respectively, clinical pressure changes in mean pulmonary artery pressure and mean arterial pressure, during ten minutes of continuous SVC occlusion in accordance with the principles of the present invention.
Figure 28B:
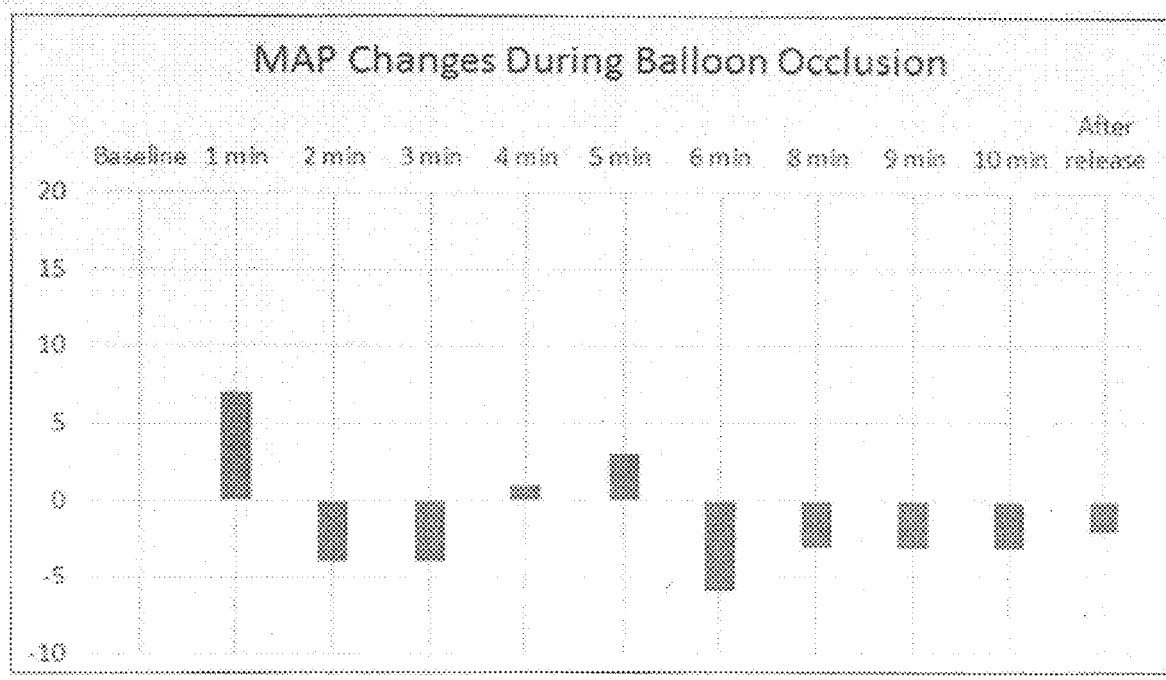

Referring now to FIGS. 28A-28B, similar to the study discussed above with respect to FIGS. 25A-25D, Applicants also studied the effect of prolonged SVC occlusion on a human subject. Specifically, the controller was programmed to cause the SVC flow limiting element to at least partially occlude the SVC for ten minutes. Prior to the ten-minute occlusion, the SVC was occluded for a period of five minutes and then permitted to rest for a period of five minutes. The change in mean pulmonary artery pressure, and the change in mean arterial artery pressure, from a baseline measurement before occlusion (i.e., after five minutes of rest), was measured at each minute from 1-10 minutes of occlusion, and after release. As is shown in FIGS. 28A-B, the effects observed during five minutes of occlusion persisted throughout the ten-minute occlusion period without any attrition of the 'cardio-pulmonary unloading' effect.

FIG. 28A illustrates the change in mean pulmonary artery pressure. As is shown in FIG. 28A, the mean pulmonary artery pressure decreased throughout the entirety of the occlusion and even reached its lowest level during the final two minutes of occlusion. FIG. 28B illustrates the change in mean arterial pressure change during occlusion. As is shown in FIG. 28B, the mean arterial pressure generally decreased during occlusion though it fluctuated, rising above the baseline measurement at the first minute and then again at the fourth and fifth minutes.

Figure 29:
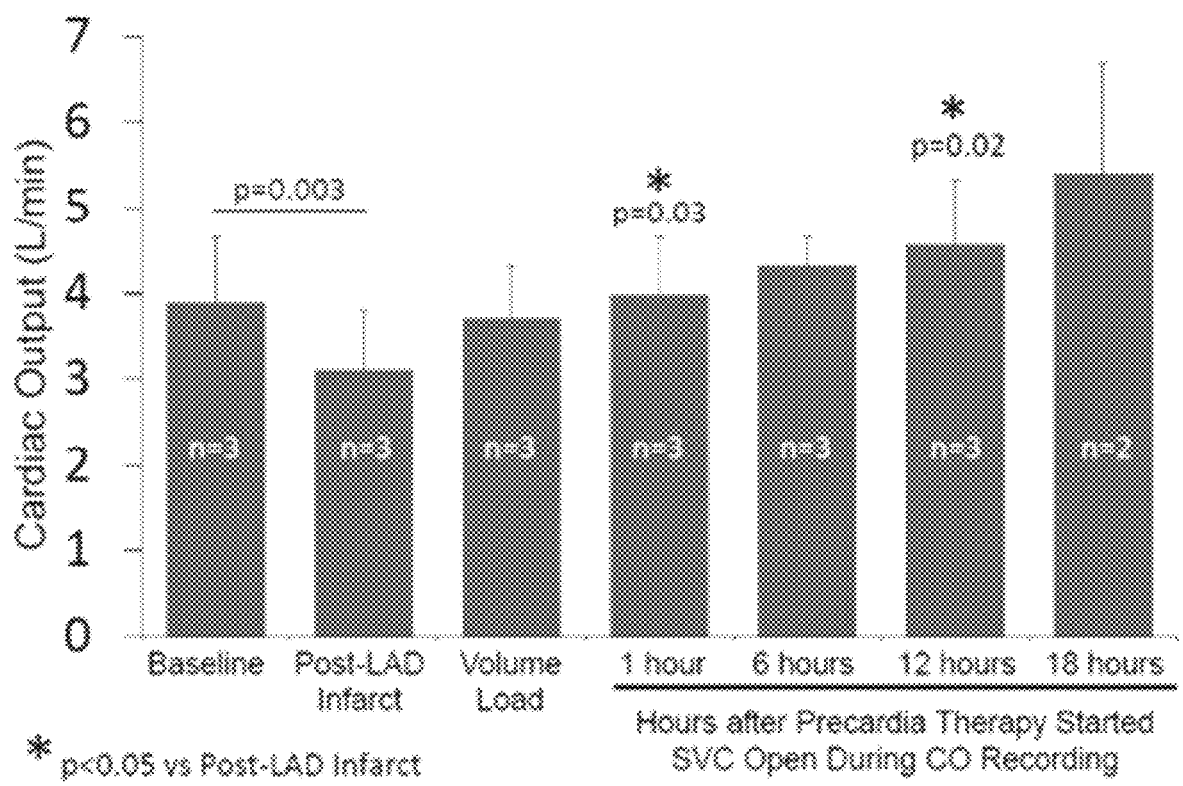
FIG. 29 illustrates the cardiac output before occlusion and during occlusion of the SVC in accordance with the principles of the present invention.

Referring now to FIG. 29, Applicants also performed more extensive testing involving use of the system and methods of the present invention over successive periods of occlusion resulting in arresting or reversing further myocardial remodeling and degeneration. Specifically, adult male swine were subjected to a heart attack by occluding the left anterior descending artery (LAD) for 120 minutes, followed by a re-opening of the blocked artery. Repetitive cycles of SVC occlusion were then performed, occluding the SVC for 5 minutes and deflating the occlusion device for 30 minutes. The repetitive cycles were repeated and performed for 18 hours. After each cycle of SVC occlusion, cardiac output was measured. FIG. 29 illustrates the results of the repetitive cycles of SVC occlusion.

As is shown in FIG. 29, cardiac output was at its lowest point post-LAD infarct but before SVC occlusion treatment. After one hour of treatment, cardiac output had returned to baseline levels. Cardiac output continued to gradually increase from one hour of treatment to eighteen hours of treatment, reaching a maximum cardiac output at eighteen hours. These findings suggest for the first time that after acute heart injury, mechanically reducing cardiac pressure and volume (i.e., unloading) by intermittently occluding the SVC and thereafter ceasing occlusion (i.e., recovery) may condition the heart muscle, allowing for periods of exercise and rest. In this manner, the repetitive cycles are akin to interval-training high-intensity workouts (e.g., sprinting) followed by rest. The repetitive cycles strengthen the heart and improve cardiac output and function. While the ratio of occlusion-to-rest was 10:1 (5 minutes on, 30 seconds off), it is understood that other ratios would produce beneficial results. For example, a ratio range of 5-20 minutes of occlusion to 10-100 seconds of rest may be beneficial. It is further understood that occluding the SVC for up to 95% of an hour may be beneficial. Accordingly, the SVC occlusion system described herein may alternatively or additionally be used post-infarction to treat injuries to the heart from the infarction to enhance recovery through myocardial unloading.

As referenced above, the SVC occlusion system described herein may alternatively or additionally be used to treat pulmonary hypertension as occlusion of the SVC may result in reduced pressure in the pulmonary arteries. While heart failure is a common cause of pulmonary hypertension, pulmonary hypertension may be caused by primary lung disease. It is understood that the SVC occlusion system may be used to treat pulmonary hypertension, whether or not the cause of pulmonary hypertension is heart failure.

Figure 30:
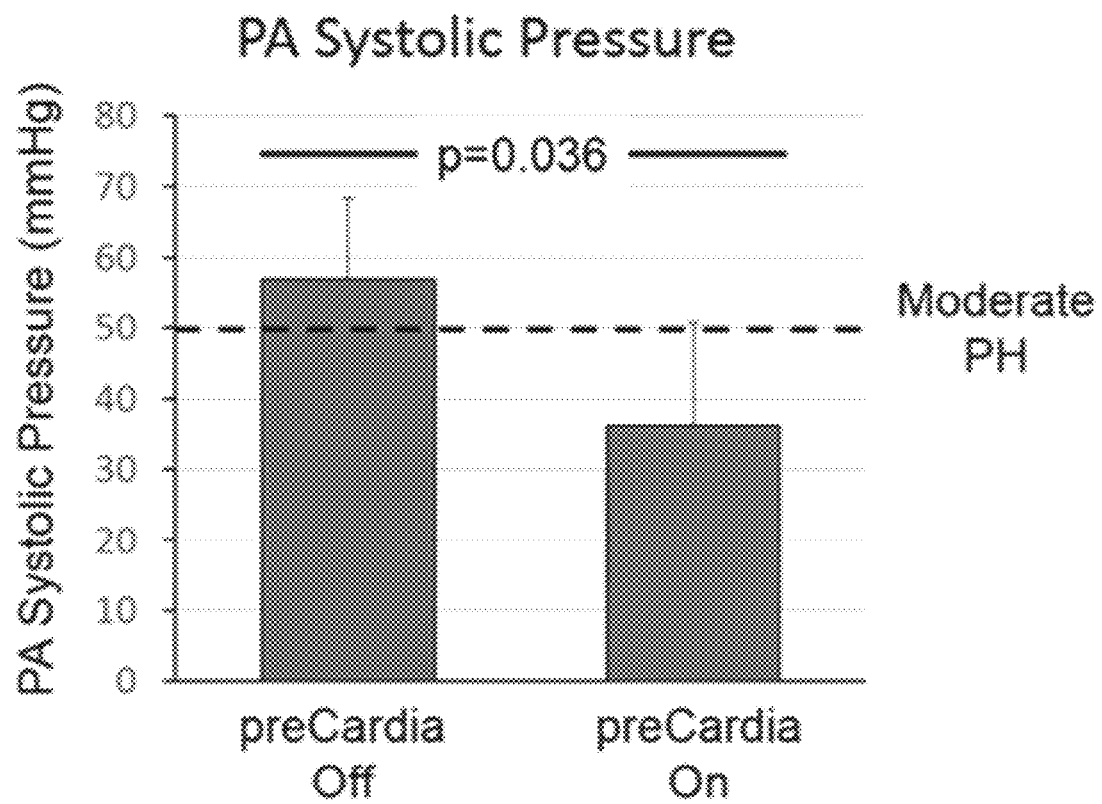
FIG. 30 illustrates the pulmonary artery systolic pressure during with occlusion and without occlusion of the SVC in accordance with the principles of the present invention.

Referring now to FIG. 30, Applicants have observed that implantation of the SVC occlusion system in five patients with pulmonary hypertension due to heart failure results in significant reduction in the pulmonary artery systolic pressure (PASP). The patients were subject to five minutes of SVC occlusion, mechanically reducing cardiac pressure and volume (i.e., unloading). As is shown in FIG. 30, SVC occlusion significantly reduced the PASP below the level of moderate pulmonary hypertension, defined as elevated PASP above 50 mmHg. Accordingly, the SVC occlusion system described herein may implanted to treat pulmonary hypertension. As discussed above with respect to FIG. 26B as well as FIG. 27D, Applicants also observed that implantation of the SVC occlusion system resulted in a decrease in the mean pulmonary artery pressure for each patient.

The benefits observed in the foregoing animal and human testing suggests that successive SVC occlusion could be used to treat any heart injury including, but not limited to, acute heart injury due to a heart attack, myocarditis, valvular insufficiency, volume overload or congestive heart failure, and many other acute or chronic heart injury. In one example, the SVC occlusion system described herein may be used acutely, e.g., in an acute-care setting, to arrest or reverse the systems of heart failure, thereby shifting the Frank-Starling curve illustrated in FIG. 2A, toward line 7 representing a healthy patient. In this manner, the patient will see immediate improvement in increased cardiac performance, with further continuous improvement in myocardial function throughout the course of treatment. To prolong the effects of the system, the SVC occlusion system may be implanted within the patient for long term use. As the SVC occlusion system described herein may be implanted or worn by the patient continuously and in an ambulatory setting, rather than being confined to a bed, the patient may receive the benefits of the system over a much longer period as compared to acute care.

Figure 31:
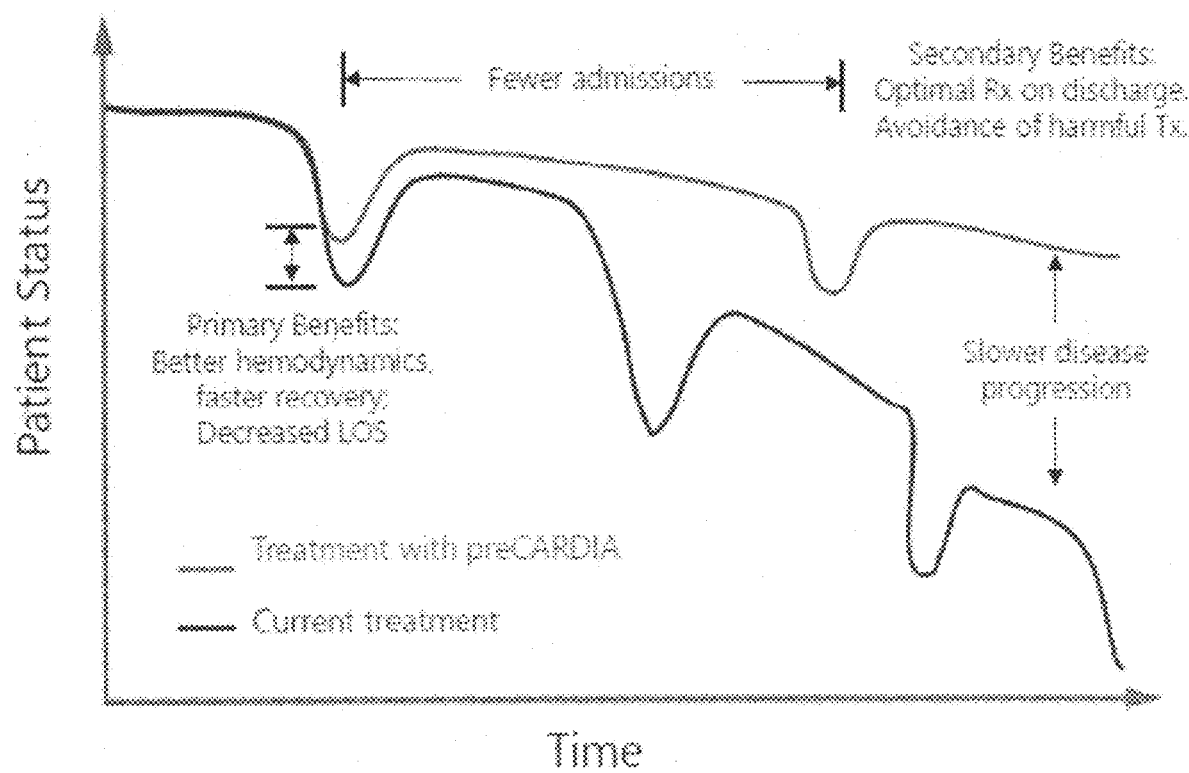
FIG. 31 is a prophetic example of how SVC occlusion in accordance with the principles of the present invention is expected to change the course of the disease.

FIG. 31 is a prophetic example of how SVC occlusion in accordance with the principles of the present invention is expected to change over the course of the disease. For example, primary benefits include better patient hemodynamics, faster recovery, and decreased length of stay (LOS) of patients in the hospital. Over time, SVC occlusion may significantly slow disease progression.

Referring now to FIG. 32 an alternative flow limiting element is illustrated. One undesired effect of occlusion of the SVC is increased venous blood pressure upstream of the occlusion device. It is well known that high cephalic venous pressure may lead to various unwanted effects. To reduce this risk of excessive pressure buildup upstream of the flow limiting element, a relief valve may be integrated into a flow limiting element, as illustrated in FIG. 33, to permit fluid flow from the SVC to the right atrium. The relief valve may be unidirectional, permitting blood flow only in the direction of the right atrium. The relief valve is preferably configured to open at a pressure in the SVC between 30-60 mmHg. However, it is understood that the relief valve may be designed and configured to open at other pressures in the SVC.

The flow limiting element illustrated in FIG. 32 may be used with a system similar to the system illustrated in FIGS. 4A-4B. As is shown in FIG. 32, the flow limiting element may be cylindrical flow limiting element 112. Cylindrical flow limiting element 112 may include cylindrical balloon 113 which may be inflated and deflated by delivering fluid to cylindrical balloon 113 from a catheter. Flow limiting element 112 may be sized and configured to fit within the SVC and may conform to the contours of the inner wall of the SVC. Flow limiting element 112 may be delivered to the SVC on a catheter. Cylindrical balloon 113 may be introduced to the SVC in a deflated configuration. Upon arriving at the SVC, cylindrical balloon 113 may be inflated to obstruct or limit blood flow in the SVC.

Cylindrical balloon 113 may define internal lumen 114 when cylindrical balloon 113 is inflated. When relief valve 115 is open and cylindrical balloon 113 is inflated, blood may pass through cylindrical balloon 113. Internal lumen 114 may extend from one end of cylindrical balloon 113 to the other. While internal lumen 114 may have a consistent cylindrical shape throughout, it is understood that the size and shape of both cylindrical balloon 113 and internal lumen 114 may vary. Additionally, internal lumen 114 need not be aligned with the center of the balloon and may even adopt a non-cylindrical shape.

Referring now to FIG. 33, a cutaway view of cylindrical flow limiting element 112 is shown. As is shown in FIG. 33, relief valve 115 may be coupled to the internal wall of cylindrical balloon 113 within central lumen 114. Relief valve 115 may include a single flow obstructing element or a plurality of flow obstructing elements (e.g., a plurality of flexible leaflets) that work in concert to obstruct blood flow through central lumen 114. Relief valve 115 may be coupled to the center of cylindrical flow limiting element 112 or alternatively may be positioned closer to or at an upstream or downstream end of cylindrical flow limiting element 112. For example, relief valve 115 may be positioned at an upstream end of cylindrical flow limiting element 112 furthest from the right atrium of the patient. This configuration may avoid pooling of blood or a standing column of blood within central lumen 114 which may occur where relief valve 115 is positioned in a central or downstream region of central lumen 114.

Relief valve 115, illustrated in FIG. 33 in a closed position, may be designed to open at a certain pressure. For example, relief valve 115 may be designed to open at a pressure between 30-40 mmHg. However, it is understood that other pressures may also be desirable. Below the pressure at which relief valve 15 is designed to open, relief valve 115 may obstruct fluid flow through central lumen 114. Above the pressure at which relief valve 115 is designed to open, relief valve 115 may permit the passage of blood through internal lumen 114, thereby reducing cephalic venous pressure.

Relief valve 115 may be constructed of any suitable biocompatible material, including, but not limited to, elastomers, rigid or flexible polymers, metals, and any combination thereof. The functionality of the relief valve 115 may depend solely on the materials and design (i.e., elasticity, rigidity, thickness) of the valve, and/or may be dictated by mechanical, electrical, and/or magnetic features. The threshold for which the valve permits fluid to flow may be predetermined by valve design and/or may be mechanically adjustable.

Figure 34A:
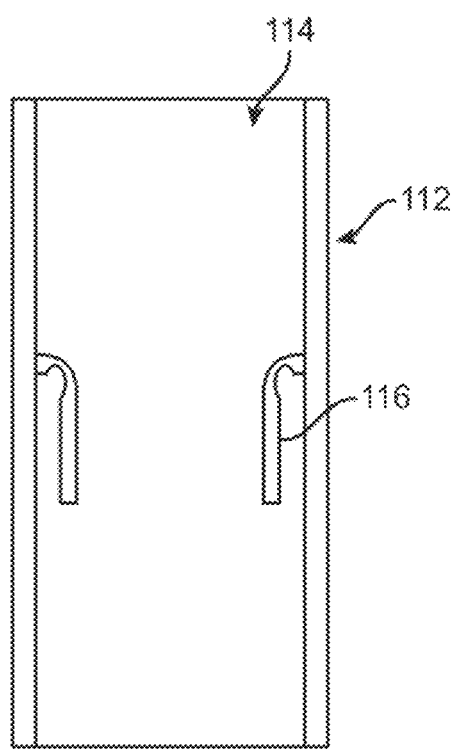
FIGS. 34A-B are cross-sectional views of the cylindrical flow limiting element having binary and gradual relief valves.
Figure 34B:
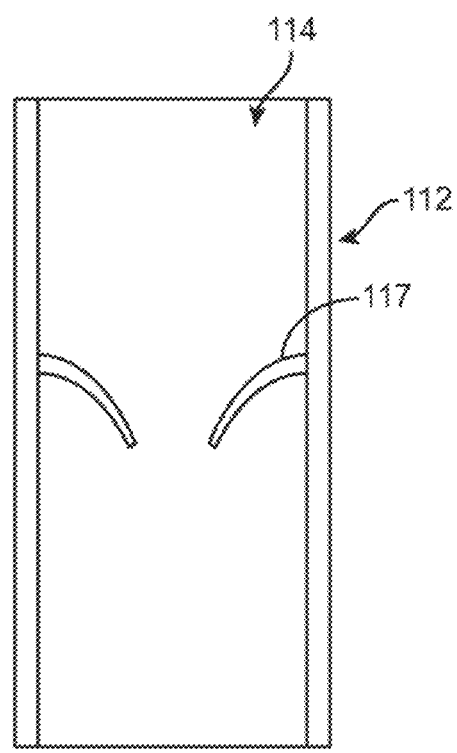

Referring now to FIGS. 34A and 34B, two different relief valve designs are shown within internal lumen 114 of cylindrical flow limiting element 112. Binary relief valve 116, shown in FIG. 34A, maintains a substantially closed position until rapidly transitioning to a substantially open position when a given force is applied. The force at which relief valve 116 transitions from a closed to an open position is preferably between 30-60 mmHg though it is understood that this pressure could be any pressure. To achieve the binary (i.e., on/off) functionality, binary relief valve may include a cutout section designed to give-way in response to a given force. Upon opening and permitting fluid to pass, thereby releasing pressure, elasticity in the material or other mechanical features may cause binary relief valve 116 to spring back into a closed position. It is understood that this binary functionality may be achieved using a variety of other designs and/or by incorporating other materials. For example, relief valve 132 in FIG. 38A-B may also achieve the binary functionality.

Gradual relief valve 117, as shown in FIG. 34B, is designed to open gradually with increasing pressure. This functionality may be achieved, for example, with valve leaflets that have a constant thickness or a progressively thinner cross-section as the leaflets move from the internal wall of cylindrical balloon 113 towards the center of internal lumen 114. However it is understood that any valve design that gradually permits increased fluid flow in response to increased pressure may be used as a gradual relief valve.

Figure 35:
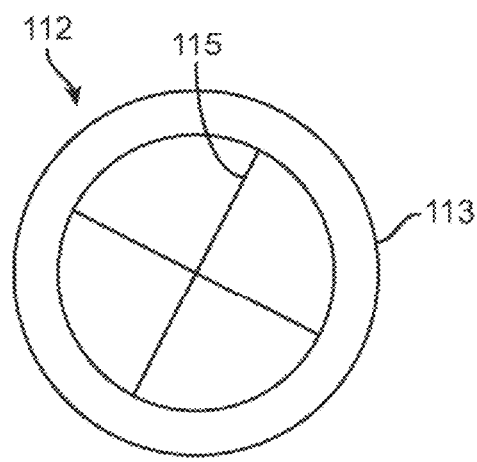
FIG. 35 is a top view of the cylindrical flow limiting element having a relief valve in a closed position.

Referring now to FIG. 35, a top view of cylindrical flow limiting element 112 is shown. Relief valve 115, shown here in a closed position, prevents flow through the internal lumen of cylindrical balloon 113 as long as pressure remains below a certain threshold. Although a relief valve design having four flexible leaflets or flaps is depicted, any relief valve design that may be coupled within internal lumen 114 of cylindrical balloon 113 may be used including valves with fewer/more leaflets.

Figure 36A:
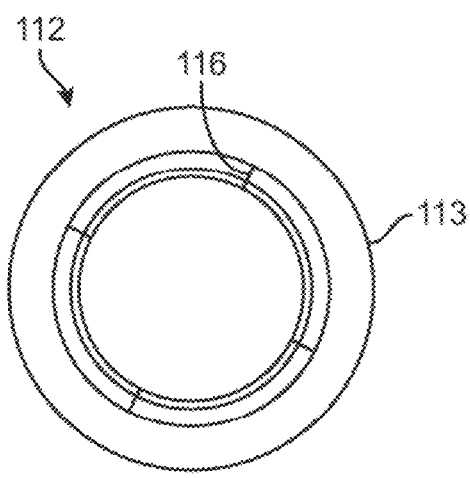
FIGS. 36A-B are top views of the cylindrical flow limiting element having a binary relief valve and a gradual relief valve in an open position.
Figure 36B:
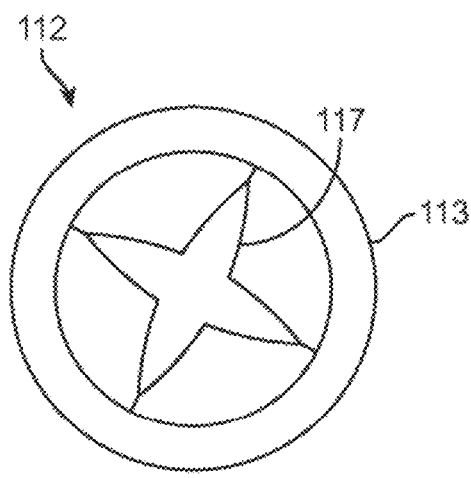

Referring now to FIGS. 36A and 36B, a top view of cylindrical flow limiting element 112 is shown. FIG. 36A illustrates binary relief valve 116, also shown in FIG. 34A, in its open position. FIG. 36B illustrates gradual relief valve 117, also shown in FIG. 34B, in a partially open position. As discussed above, binary relief valve 116 is designed to open to a substantially open position upon reaching its set pressure. On the other hand, gradual relief valve 117 is designed to open gradually as pressure increases above a certain threshold.

Figure 37A:
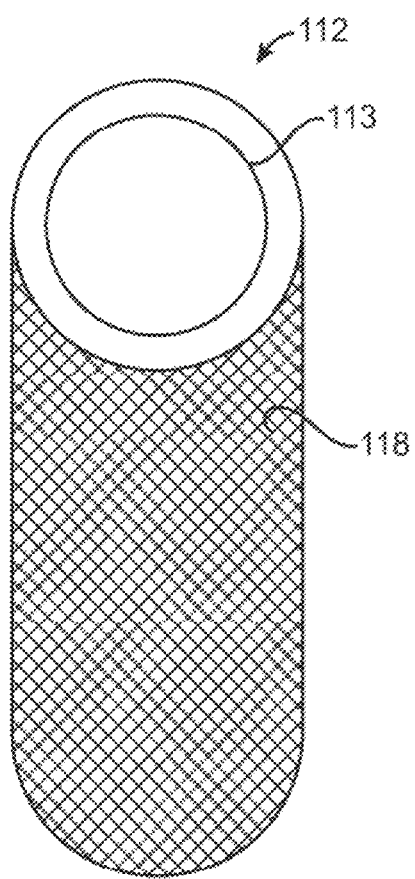
FIGS. 37A-B are perspective and cutaway views of the cylindrical flow limiting element engaged with a stent.
Figure 37B:
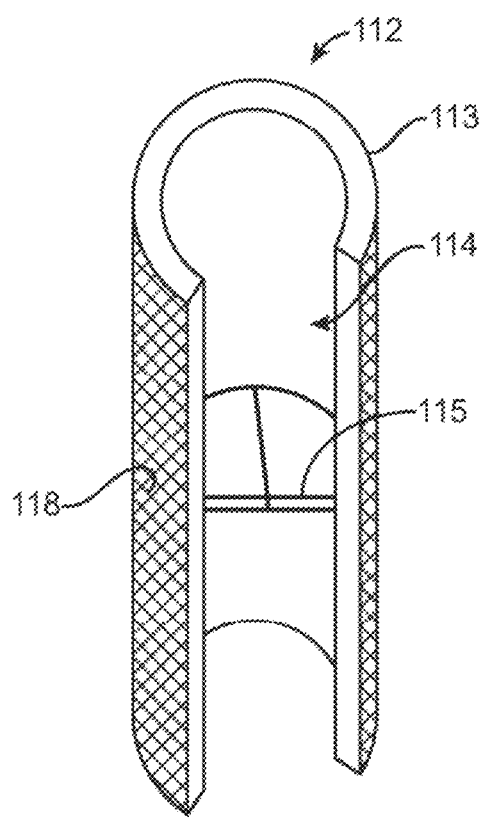

Referring now to FIGS. 37A and 37B, it may be desirable to place a stent 118 around cylindrical balloon 113. Stent 118 may, for example, serve as both a receiver and emitter of electrical signals. Such uses include, but are not limited to, serving as an ECG lead, emitting signals related to autonomic activity, and receiving neuromodulation signals. Stent 118 may be self-expanding and may be made of an electrically conductive material. Stent 118 may be integrated into to cylindrical flow limiting element 112 and/or may be removably coupled to cylindrical flow limiting element 112.

Figure 38A:
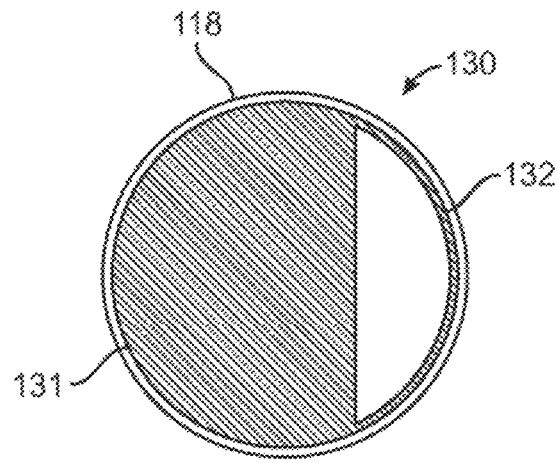
FIGS. 38A-B are top views of the cylindrical flow limiting element having a balloon occluder in an inflated and deflated position.
Figure 38B:
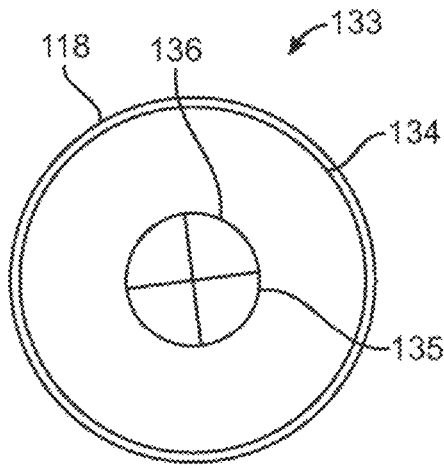

Referring now to FIGS. 38A and 38B, cylindrical flow limiting element 130 is illustrated. As is shown in these figures, cylindrical flow limiting element 130 includes balloon occluder 131 and relief valve 132 which are both integrated into stent 118. Relief valve 132 and balloon occluder 131 are located adjacent to each other within stent 118. FIG. 38A depicts the cylindrical flow limiting element 130 in its inflated position, occluding flow within the SVC. FIG. 38B depicts the occlusion device in its deflated position, permitting flow through the SVC. As is illustrated in FIG. 38B, balloon occluder 131 may be coupled to relief valve 132 and when deflated may contract toward relief valve 132. Relief valve 132 may be hinged to stent 118 and may open to permit blood flow when a certain pressure is achieved within the SVC. Relief valve 132 may be constructed using any of the techniques, designs, and materials disclosed above with respect to relief valves.

Figure 39A:
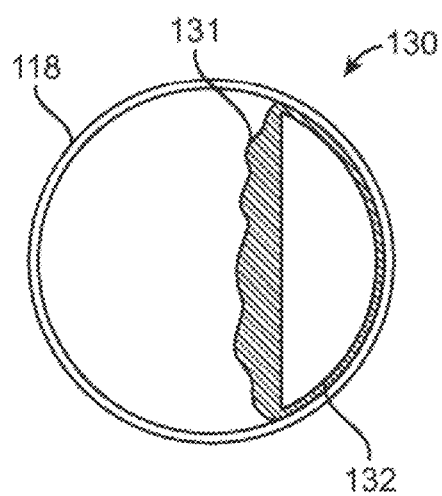
FIGS. 39A-B are top views of the cylindrical flow limiting element having a cylindrical balloon occluder in an inflated and deflated position.
Figure 39B:
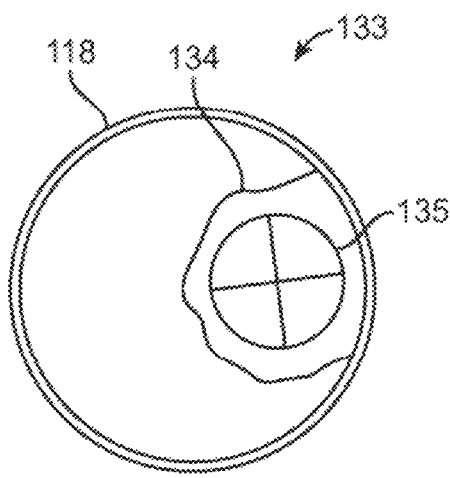

Referring now to FIGS. 39A and 39B, cylindrical flow limiting element 133 is illustrated. As is shown in these figures, cylindrical flow limiting element 133 includes cylindrical balloon occluder 134 and relief valve 135 which are both integrated into stent 118. Cylindrical balloon occluder 134 may be inflated to conform to the shape of stent 118. As is shown in FIG. 39B, cylindrical balloon occluder 134 may have an outer surface that is coupled to stent 118 along a portion of the outer surface. Relief valve 135 may be coupled to cylindrical balloon occluder 134. Cylindrical balloon occluder 134 may define internal lumen 136 when inflated through which blood may pass if relief valve 135 is open.

FIG. 39A depicts cylindrical flow limiting element 133 with cylindrical balloon occluder 134 in an inflated configuration. When inflated, cylindrical balloon occluder 134 limits flow within the SVC. With cylindrical balloon occluder 134 inflated, relief valve 135 may open as required to relieve any overpressure in the SVC. FIG. 39B depicts cylindrical flow limiting element 133 in a deflated configuration. When deflated, cylindrical flow limiting element 133 permits flow through the SVC. In the deflated configuration, cylindrical balloon occluder 134 reduces in size and moves toward the portion of the stent wall that cylindrical balloon occluder 134 is coupled to. Similarly, relief valve 135 moves toward stent 118 when cylindrical flow limiting element 133 is in a deflated configuration. Cylindrical balloon occluder 134 having a reduced size when deflated, permits blood to flow through stent 118, around deflated balloon occluder 134.

Referring now to FIGS. 40A and 40B, cylindrical flow limiting element 137 is illustrated. Cylindrical flow limiting element 137 includes stent 118 and relief valve 138. Unlike the occlusion devices illustrated in FIGS. 32-39, cylindrical flow limiting element 137 does not include a balloon. Instead, relief valve 138 may be coupled directly to stent 118 as is shown in FIG. 40B. Stent 118 may be an expandable stent and may be anchored to the inner wall of the SVC. Relief valve 138 may take the form and have characteristics similar to any of the relief valves discussed above with respect to FIGS. 32-39. Cylindrical flow limiting element 137 may entirely eliminate flow in the SVC until a certain threshold pressure his achieved in the SVC, at which point relief valve 138 may open to permit flow from the SVC to the right atrium.

Figure 41:
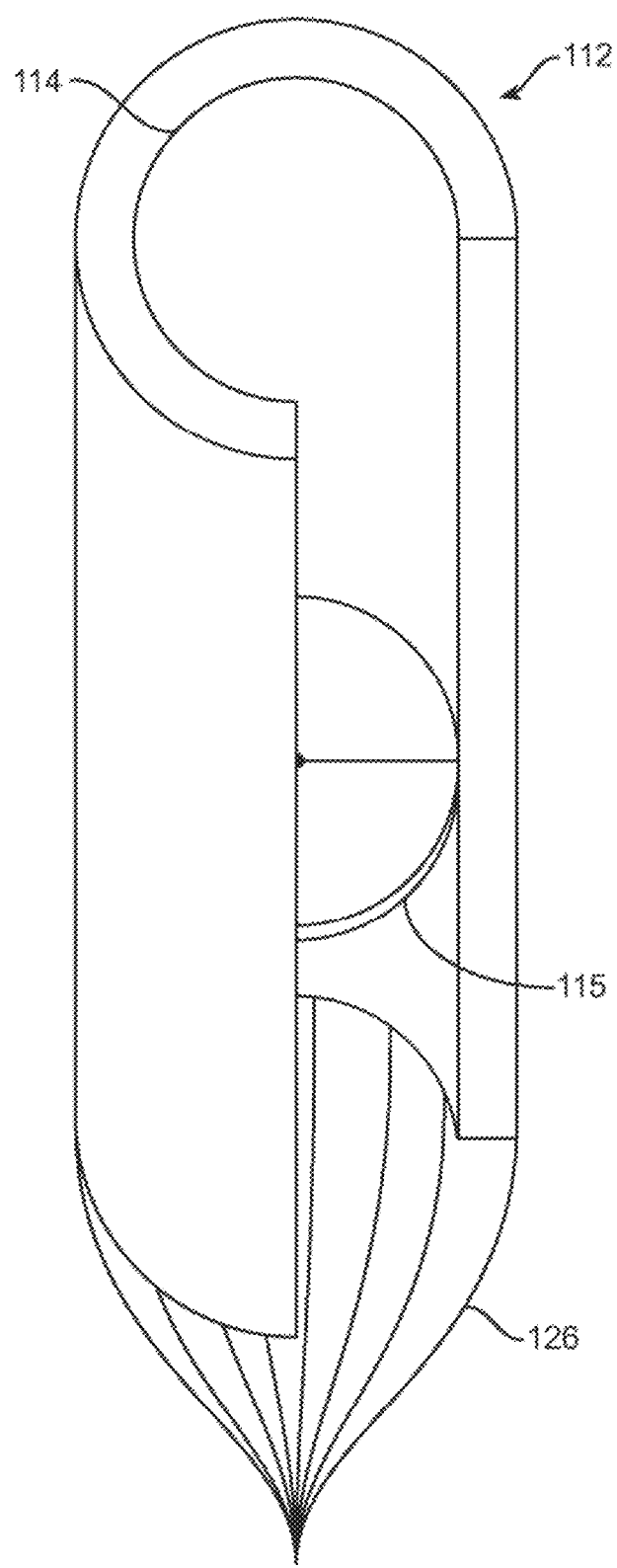
FIG. 41 is a cutaway view of a cylindrical flow limiting element coupled to a filter.

Referring now to FIG. 41, cylindrical flow limiting element 112 of FIG. 32 is illustrated coupled to filter 126. Filter 126 may be placed downstream of cylindrical flow limiting element 112. When relief valve 115 is closed, blood may pool in central lumen 114 of cylindrical balloon 113 resulting in a stagnant blood column, leading to thrombosis. When relief valve 115 is opened, thrombus may be released into the right atrium, which may cause severe problems and even death. Filter 126, may be supported either directly by a catheter or by a structural feature of cylindrical flow limiting element 112 such as cylindrical balloon 113, relief valve 115, or stent 118 if applicable, and may serve to catch thrombus. For example, filter 126 may be coupled to cylindrical balloon 113 at the downstream end of cylindrical flow limiting element 112, as is shown in FIG. 41. It is understood that filter 126 may be integrated into any of the flow limiting elements described herein.

To determine whether the SVC is fully occluded or to what degree the SVC is occluded, traditional methods involving injecting contrast agent into the patient and observing movement of the contrast agent under fluoroscopy may be employed. Alternatively, pressure sensors may be positioned relative to the occlusion balloon as discussed herein, and pressure waveforms may be analyzed to determine whether the SVC is occluded. For example, CardioMEMS™ HF System pressure sensors are available from Abbott, St. Paul, Minnesota. The pressure sensors may communicate wirelessly with, e.g., the implanted controller. Pressure waveforms may also be analyzed to determine a patient's filling pressures, diastolic conditions and/or other cardiac conditions or indications. For example, waveforms may be analyzed to detect a prominent 'C-V' wave indicative of tricuspid regurgitation due to volume overload. In another example, waveforms may detect an 'A' wave suggestive of complete heart block, Ventricular Tachycardia (VT), or pulmonary hypertension. The systems described herein may be used as a diagnostic monitoring tool by analyzing waveforms and may respond accordingly using the SVC occlusion techniques described herein.

Figure 42A:
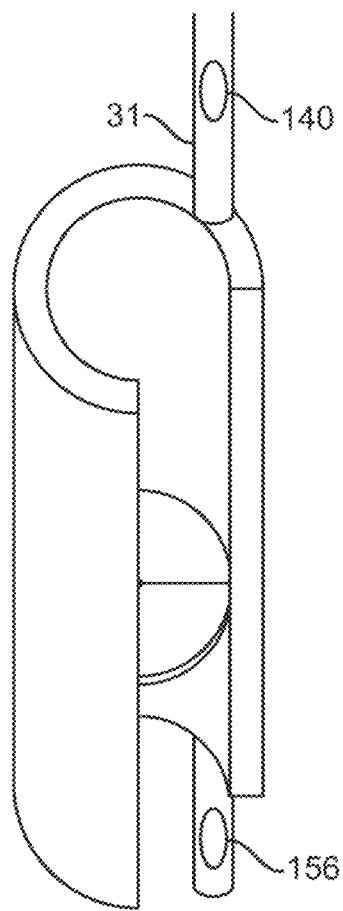
FIG. 42A is a cutaway perspective view of a cylindrical flow limiting element coupled to a catheter with a sensor and FIG. 42B is an exemplary phasic curve.
Figure 42B:
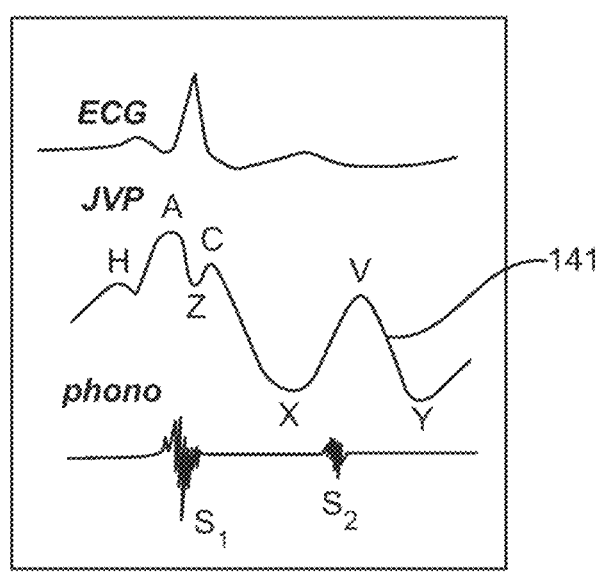

FIG. 42A illustrates pressure sensor 140 which may generate pressure waveforms. Pressure sensor 140 may be incorporated into catheter 31 and may be disposed at a location proximal to the occlusion balloon to provide pressure measurements indicative of the Jugular Vein Pressure (JVP). Pressure sensor 156 optionally may be incorporated into catheter 31 distal to the occlusion balloon. A user of the system illustrated in FIG. 42A may monitor the waveform readings from pressure sensor 140 and determine when the wave form changes from phasic to non-phasic. When the occlusion balloon is deflated, the pressure waveform will vary in phase with the heartbeat, as is illustrated in curve 141 of FIG. 42B. When the occlusion balloon is inflated, the pressure waveform then flatlines. In this manner it may be determined whether the SVC is occluded, without the need to inject contrast and without the patient being in a cathlab or under x-ray. Also, the pressure waveform may be used to determine when to actuate the flow limiting element and when to cease actuation of the flow limiting element.

Another alternative to using x-ray/fluoroscopy for determining occlusion of the SVC employs two pressure sensors on opposite sides of the occluding device. For example, FIG. 4A discussed above illustrates a system having catheter 31 including flow limiting element 32, sensor 42 and sensor 43. As is shown in FIG. 4A, sensor 42 is positioned distal to flow limiting element 32 and sensor 43 is positioned proximal to flow limiting element 32. Sensors 42 and 43 may be pressure sensors and, as explained above, may be used to determine the extent of occlusion caused by flow limiting element 32, for example, by monitoring the pressure differential across flow limiting element 32. The pressure differential value may be indicative of the amount or degree of occlusion. Also the pressure differential may be used to determine when to actuate the flow limiting element and when to cease actuation of the flow limiting element.

Figure 43:
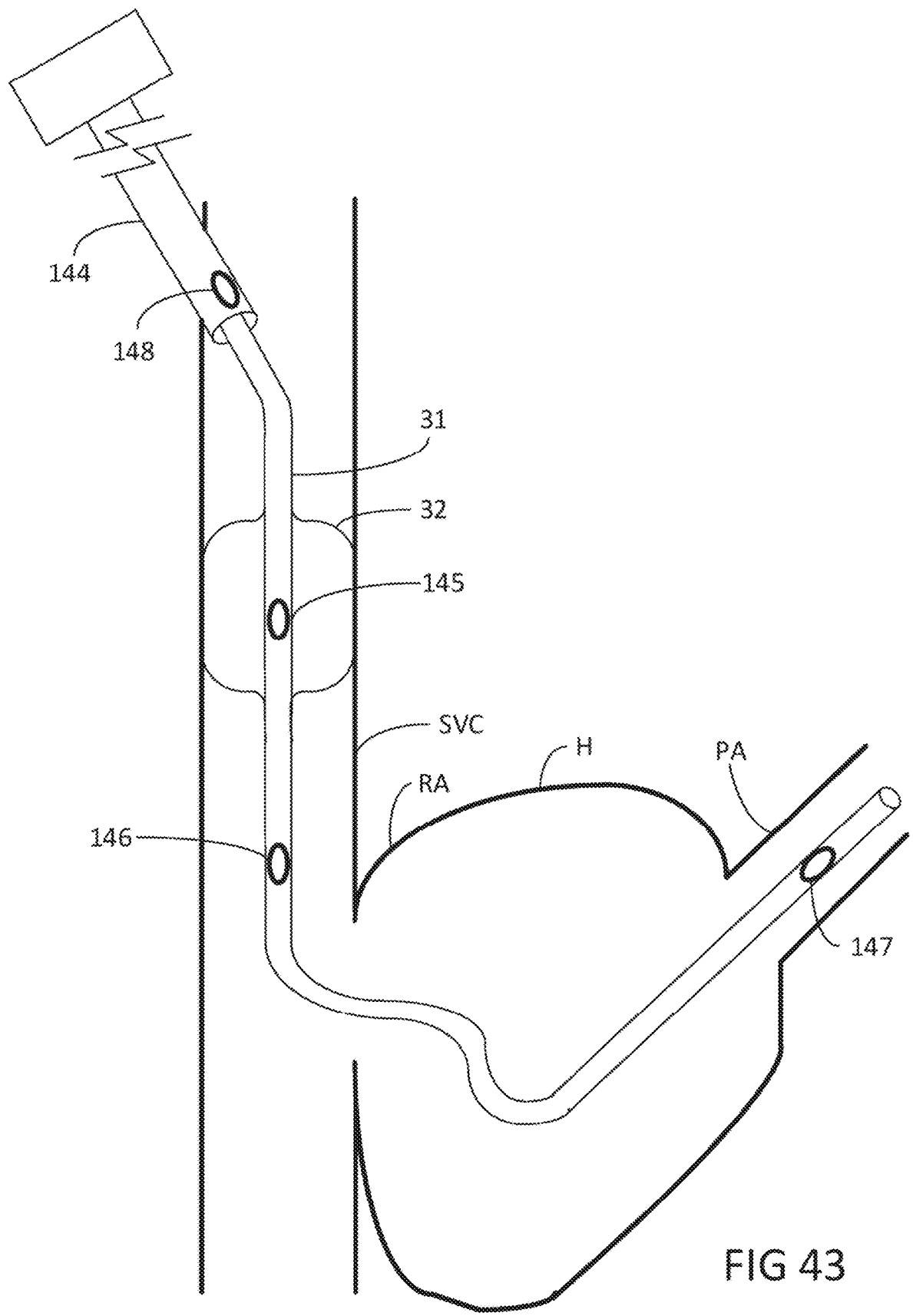
FIG. 43 is a view of an introducer sheath entering an SVC, a flow limiting element within the SVC, and a catheter positioned within the heart.

While FIG. 4A illustrates one arrangement of sensors, it is understood other arrangements of sensors may be used to obtain relevant information. As shown in FIG. 43, an alternative sensor arrangement includes catheter 31, which may be introduced into the vasculature of the patient via a delivery device, such as introducer sheath 144. Catheter 31 preferably extends into the SVC, enters the heart through the right atrium, extends into the right ventricle, and enters the pulmonary artery through the pulmonary valve. Sensors 145, 146 and 147 may be positioned along catheter 31 so that sensor 145 is positioned within flow limiting element 32 to measure the pressure within flow limiting element 32 (i.e., balloon pressure), sensor 146 is positioned along catheter 31 distal to flow limiting element 32 and within the SVC to measure SVC or right atrium pressure, and sensor 147 is positioned along catheter 31, distal to sensor 146, such that sensor 147 is positioned within the pulmonary artery and measures pulmonary artery pressure. To measure the pressure above or proximal to flow limiting element 32, sensor 148 may be placed directly on or otherwise incorporated into the distal end of sheath 144, where introducer sheath 144 enters the SVC. The pressure measured by sensor 148 is indicative of the JVP. Catheter 31 may include a plurality of lumens, which are used as inflation lumens, actuation lumens and/or for electrical communication between the controller and flow limiting element 32 and/or sensors 145, 146 and 147. Introducer sheath 144 also may include lumens for electrical communication between sensor 148 and the controller.

Figure 44:
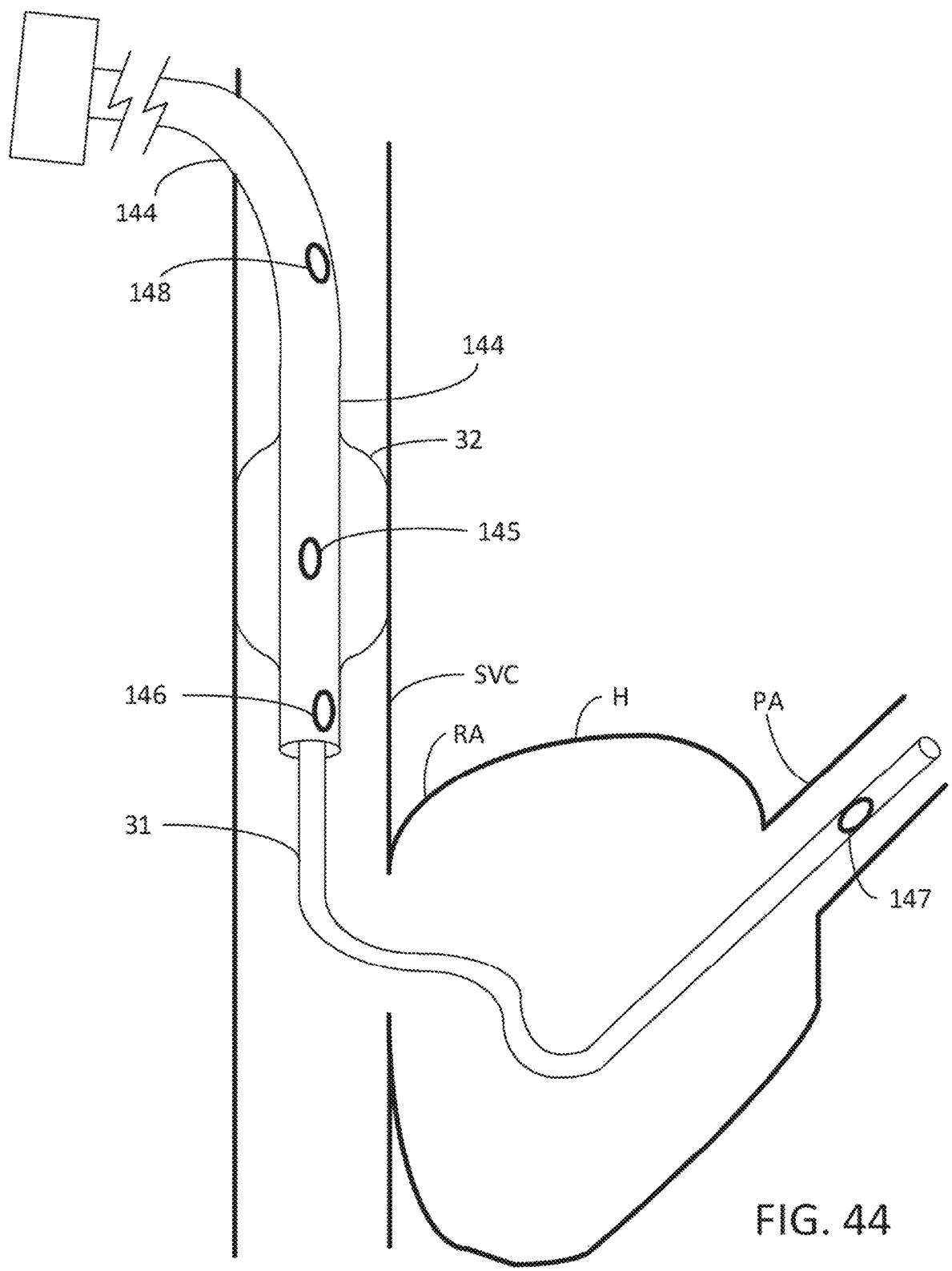
FIG. 44 is a view of an introducer sheath positioned within an SVC, a flow limiting element incorporated in the introducer sheath, and a catheter positioned within the heart.

Referring now to FIG. 44, yet another alternative embodiment is described that includes introducer sheath 144. The embodiment illustrated in FIG. 44 is similar to that of FIG. 43 except that flow limiting element 32 and sensor 145 and 146 are also incorporated into introducer sheath 144. Similar to the device illustrated in FIG. 43, sensor 148 may be positioned above or proximal to flow limiting element 32 and may measure pressure above or proximal to flow limiting element 32, which is indicative of JVP. Sensor 145 is positioned within flow limiting element 32 to measure the pressure within flow limiting element 32 (i.e., balloon pressure). Sensor 146 is positioned near a distal end of introducer sheath 144, which is distal to flow limiting element 32 and positioned within the SVC to measure SVC or right atrium pressure. Also, similar to the device illustrated in FIG. 43, catheter 31 may be introduced via introducer sheath 144 and extend through the right atrium and into the pulmonary artery. Sensor 147 preferably is disposed at a distal end of catheter 31 so that it is positioned within the pulmonary artery and measures pulmonary artery pressure. Introducer sheath 144 may include a plurality of lumens used as inflation lumens, actuation lumens and/or for electrical communication between the controller and flow limiting element 32 and/or sensors 145, 146 and 148. Catheter 31 may also include lumens for electrical communication between sensor 147 and the controller.

In the embodiment of FIG. 44, flow limiting element 32 may be selectively inflated and deflated independent of the presence of catheter 31. As flow limiting element 32 and sensors 145, 146 and 148 are disposed on introducer sheath 144, therapeutic treatment involving the inflation and deflation of flow limiting element 32 to selectively occlude the SVC may be achieved without the introduction of catheter 31. Further, pressure differentials across flow limiting element 32 may be determined using sensors 148 and 146 whether or not catheter 31 is deployed.

Figure 45:
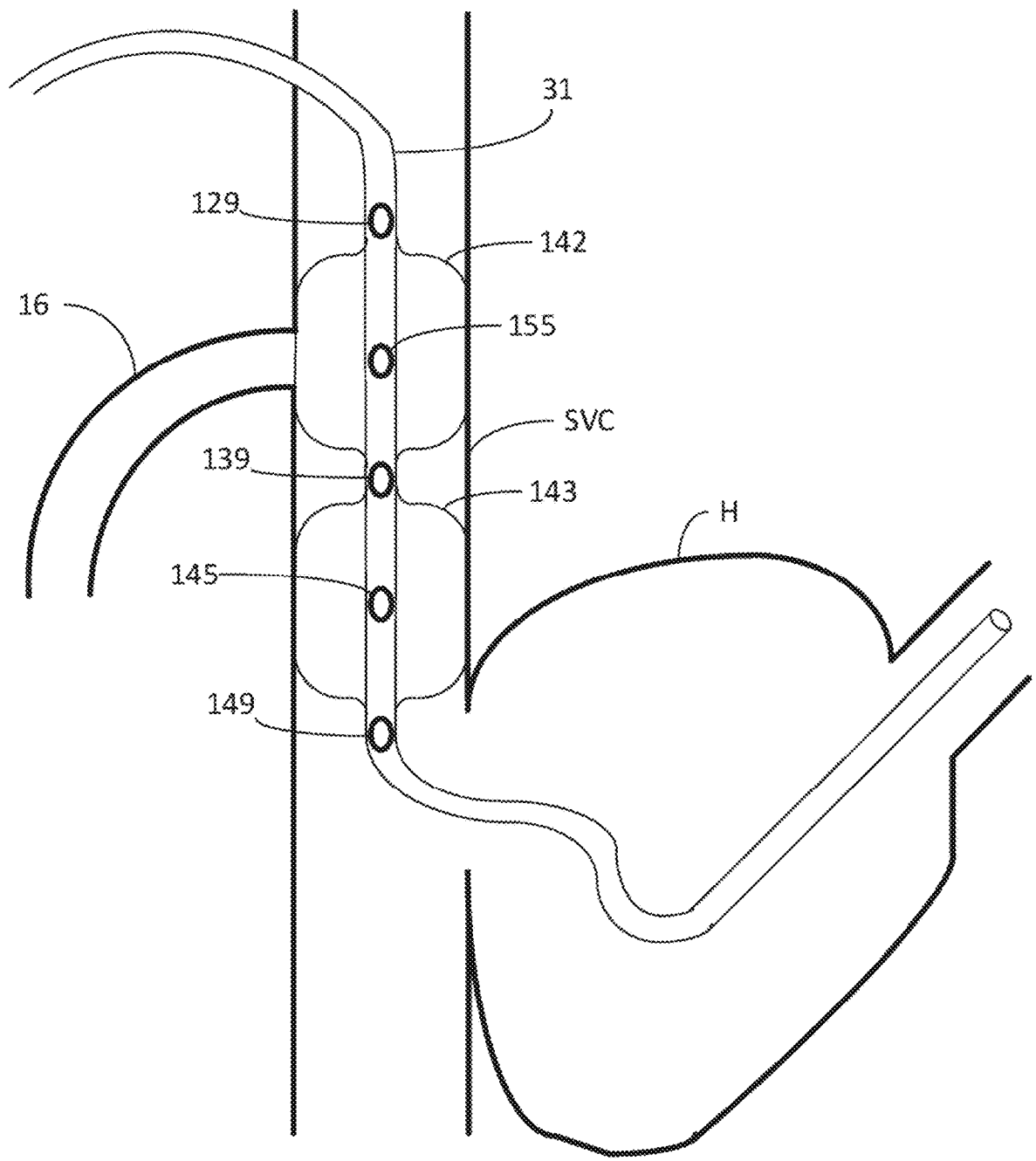
FIG. 45 is a view of an occlusion system having an azygos vein occlusion balloon and a second occlusion balloon positioned within the SVC.

Referring now to FIG. 45, yet another embodiment of the SVC occlusion system constructed in accordance with the principles of the present invention is described. Catheter 31 preferably includes two occlusion balloons, azygos vein occlusion balloon 142 and SVC occlusion balloon 143. Sensors, 129, 139 and 149 may also be disposed on catheter 31 such that sensor 129 is disposed proximal to azygos vein occlusion balloon 142 to measure pressure distal to azygos vein occlusion balloon 142, sensor 139 is disposed between azygos vein occlusion balloon 142 and SVC occlusion balloon 143 to measure the pressure between azygos vein occlusion balloon 142 and SVC occlusion balloon 143, and sensor 149 is disposed distal to SVC occlusion balloon 143 to measure the pressure distal to SVC occlusion balloon. Also, sensor 145 is positioned within SVC occlusion balloon 143 to measure the pressure within SVC occlusion balloon 143 (i.e., SVC occlusion balloon pressure) and sensor 155 is positioned within azygos vein occlusion balloon 142 to measure the pressure within azygos vein occlusion balloon 142 (i.e., azygos vein occlusion balloon pressure). Further, pressure differentials across azygos vein occlusion balloon 142 and SVC occlusion balloon 143 may be determined using sensors 129 and 139, and 139 and 149, respectively. The pressure differential value may be indicative of the amount or degree of occlusion.

Azygos vein 16 drains the posterior part of the thorax into the SVC. When the SVC is blocked, the azygos vein may provide an alternative path to the right atrium, thereby naturally shunting occluded SVC blood flow back to the right atrium. Specifically, if the SVC is occluded below the origin of the azygous vein, pressure built up above the occluded portion of the SVC may cause a percentage of venous blood to move retrograde through the azygous vein into the thorax. Azygos vein occlusion balloon 142 may be positioned in the SVC adjacent the azygos vein such that inflation of azygos vein occlusion balloon 142 restricts or prevents blood flow from entering the azygos vein from the SVC. SVC occlusion balloon 143 may be positioned below the azygos vein, distal to azygos vein occlusion balloon 142, such that inflation of SVC occlusion balloon 143 occludes the SVC but permits blood flow into the azygos vein. Catheter 31 may include a plurality of lumens used as inflation lumens and/or actuation lumens between the controller and azygos vein occlusion balloon 142 and SVC occlusion balloon 143.

Azygos vein occlusion balloon 142 and SVC occlusion balloon 143 may be selectively and independently be inflated and deflated. For example, Azygos vein occlusion balloon 142 may be deflated while SVC occlusion balloon 143 may be inflated, Azygos vein occlusion balloon 142 may be inflated while SVC occlusion balloon 143 is deflated, or both balloons may be inflated or deflated at the same time. Azygos vein occlusion balloon 142 and SVC occlusion balloon 143 may also be fully or partially inflated depending upon how much flow back to the right atrium is desirable.

When SVC occlusion balloon 143 is inflated and the azygos vein occlusion balloon 142 is deflated, the SVC is open above SVC occlusion balloon 143 and blood is permitted to travel through the azygos vein to the right atrium. Should it be desirable to further reduce flow back to the right atrium (further reducing preload), azygos vein occlusion balloon 142 may be inflated, thereby occluding the azygos vein and preventing it from acting as a natural shunt.

The systems and methods of the present invention may be used alone, as described in the examples above, or in combination with other devices configured to assist cardiac function. For example, SVC occlusion in accordance with the principles of the present invention may be used in combination with a pump such as an intra-aortic balloon pump ("IABP") or a percutaneous or surgical left ventricular assist device ("LVAD"), right ventricular assist device ("RVAD") or any other cardiovascular (i.e., heart, venous, arterial) pump, whether used for full cardiac support or for temporary assistance, thereby allowing for synchronous or asynchronous (venous and arterial) unloading of cardiac preload and afterload, respectively. For example, SVC occlusion in accordance with the principles of the present invention may be used in combination with the Impella® heart pump available from Abiomed®, Danvers, Massachusetts, as described in further detail below with reference to FIG. 49. FIGS. 49 and 51-54 illustrate the SVC occlusion system combined with exemplary RVAD, LVAD, and IABP systems.

A system of the present invention also could be coupled to other devices such as biventricular pacemakers and neuromodulatory devices. For example, biventricular pacemakers are designed to resynchronize cardiac function; if SVC occlusion favorably alters RV and LV interaction, then it may render biventricular pacing more efficient. Similarly, SVC occlusion therapy may be used in conjunction with neuromodulatory devices such that the systems have significant combined action in stimulating vagal efferents, thereby enhancing the efficacy of the neuromodulatory device. A further potential application may be in unmasking right ventricular failure after a patient is outfitted with an LVAD. By modulating the amount of venous return to the right ventricle, it may be possible to reduce overload and thereby "condition" the right ventricular myocardium to tolerate enhanced venous return being driven by the LVAD.

Figure 46:
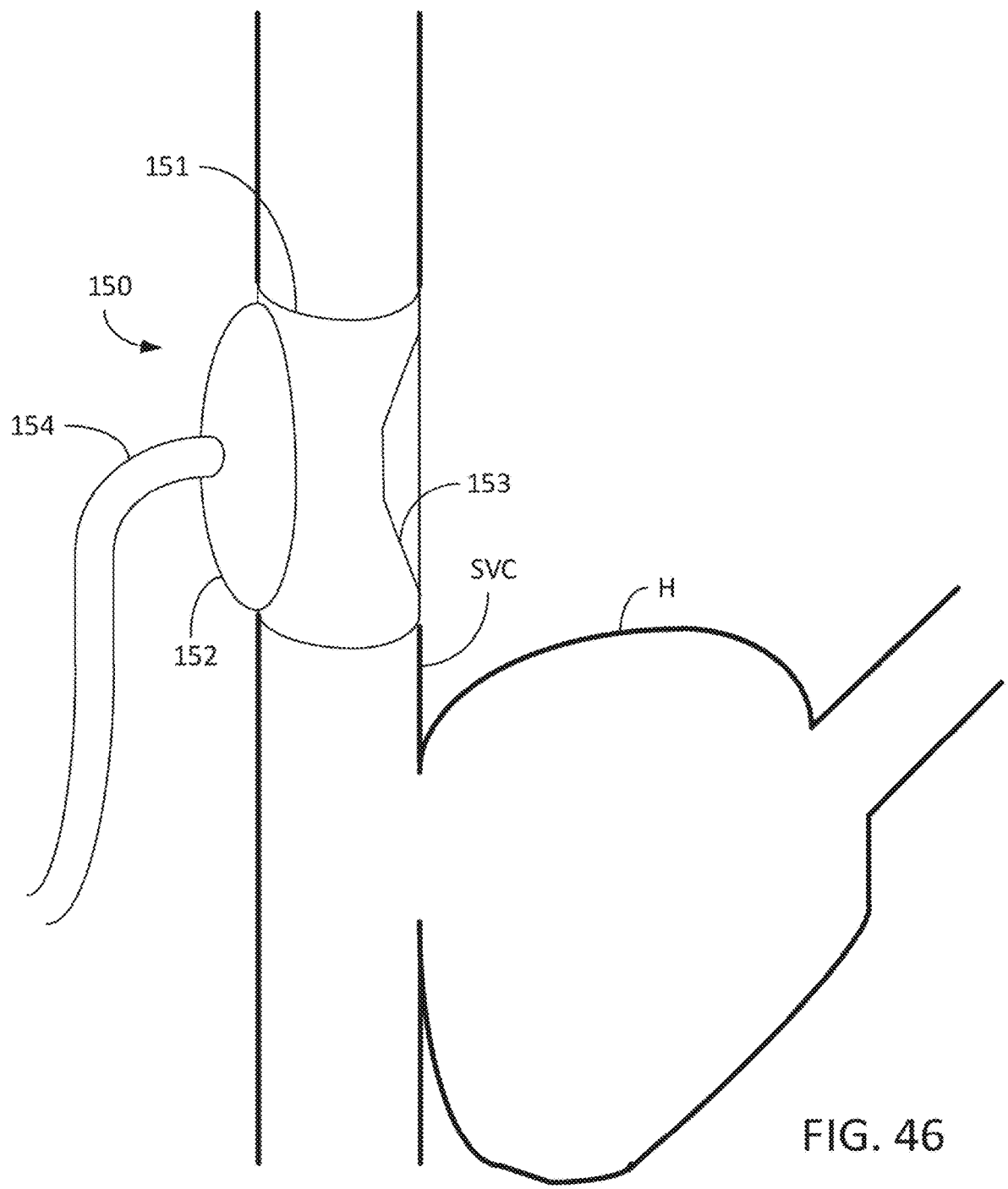
FIG. 46 is a view of an occlusion cuff wrapped around the SVC.
Figure 47A:
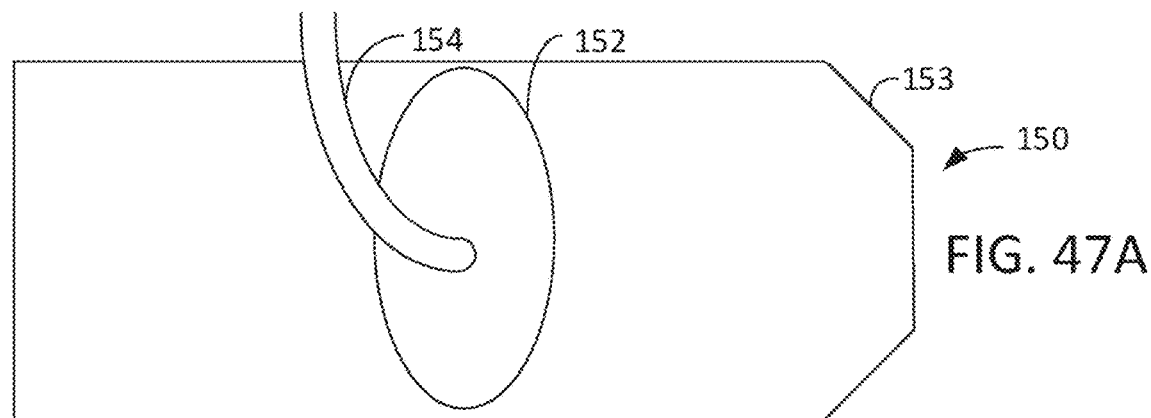
FIGS. 47A-B are views of an exterior side and an interior side of an occlusion cuff.
Figure 47B:
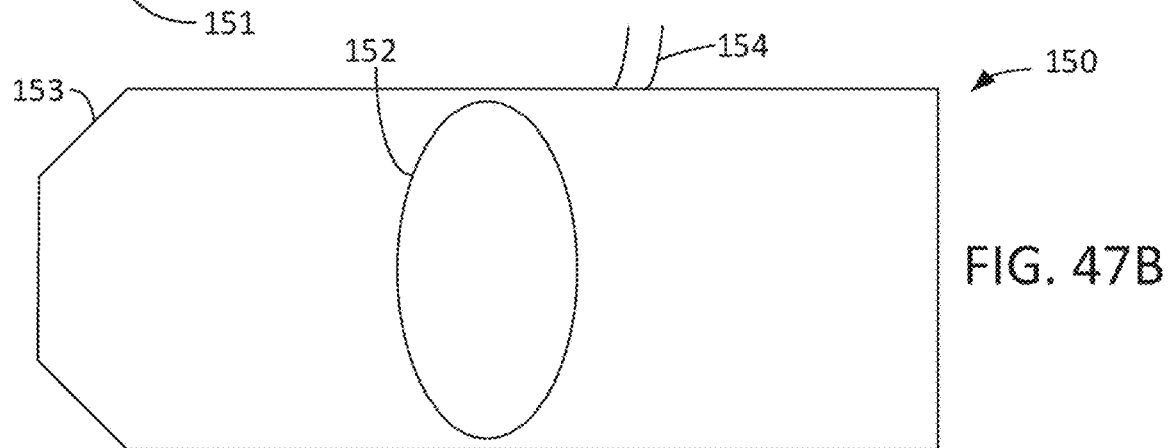
Figure 47C:
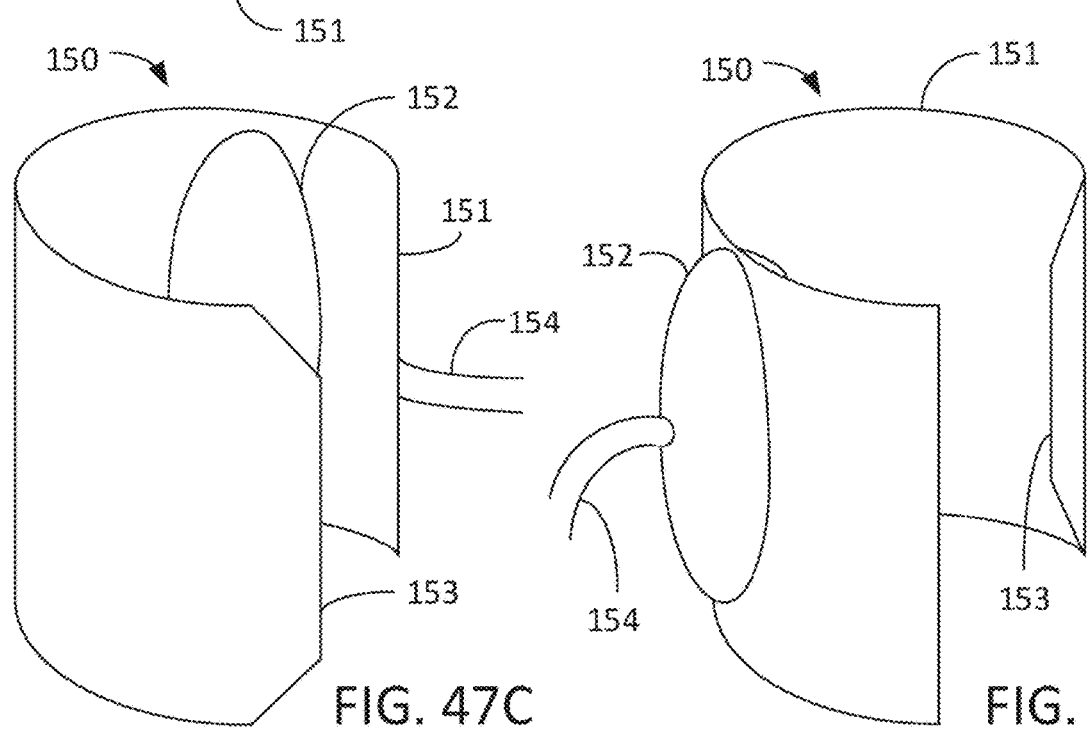
FIGS. 47C-D are perspective views of an occlusion cuff.
Figure 47D:
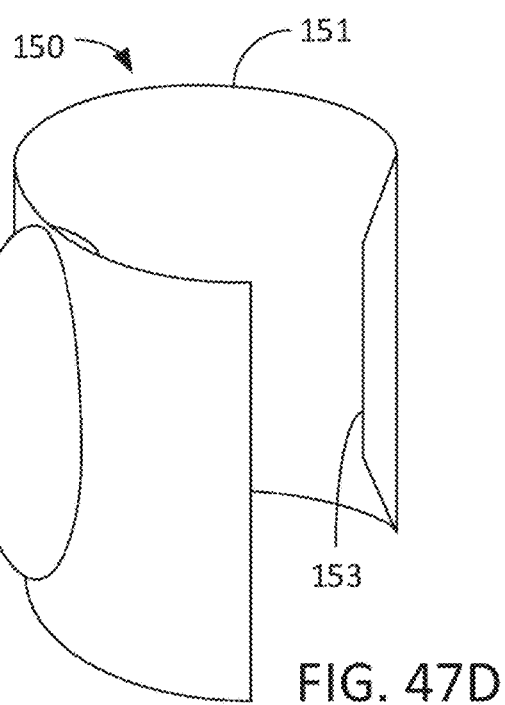

While flow limiting element 32 is described above as being positioned within the SVC and inflated and deflated within the SVC, therapeutic occlusion of the SVC as described herein alternatively may be achieved using a cuff wrapped around the exterior of the SVC to selectively constrict the SVC. Referring now to FIG. 46, cuff 150 is illustrated wrapped around the SVC. As further depicted in FIGS. 47A-D, cuff 150 may include strap 151, occlusion element 152 and locking element 153. Occlusion element 152 may be incorporated into strap 151 such that occlusion element 152 extends outward from both an exterior surface of strap 151 illustrated in FIG. 47A and an interior surface of strap 151, illustrated in FIG. 47B. The interior side or surface of strap 151 is the side facing the SVC and the exterior side or surface of strap 151 is the side facing away from the SVC.

Strap 151 may be generally rectangular in shape. Locking element 153 may be any well-known system for removably affixing one side of strap 151 to another side of strap 151. For example, strap 151 may have a magnetic locking element for tightly securing cuff 150 to the SVC. Air line 154 may connect to occlusion element 152 on one end and a controller on the other end. Occlusion element preferably has elastic properties such that it inflates when air line 154 delivers air or other fluid to occlusion element 152. Occlusion element 152 may expand outwardly from the interior side of strap 151 when inflated.

Referring again to FIG. 46, strap 151 of cuff 150 may be wrapped around the SVC and locked tightly onto the SVC using locking element 153. Upon locking cuff 150 into place on the SVC, occlusion element 152 may be selectively inflated and thus expanded toward the SVC by delivering fluid through air line 154. As strap 151 is substantially non-elastic, the inflation of occlusion element 152 will result in expansion of occlusion element 152 and compression of the SVC, thereby restricting flow through the SVC. Accordingly, occlusion of the SVC may be achieved when occlusion element 152 expands and encroaches into the SVC, causing the SVC to collapse inward. Thus, by selectively deflecting and inflating occlusion element 152, therapeutic occlusion of the SVC described herein may be achieved.

Controller 33 is programmed to cause flow limiting element 32 to at least partially occlude the SVC for a first predetermined time interval, and then contract, e.g., deflate, for a second predetermined time interval, e.g., at least one second, less than one minute, or one to thirty seconds. Preferably, the first predetermined time interval is more than a minute, between two and eight minutes, or between four and six minutes. For example, the first predetermined time interval may be five minutes, plus or minus a minute. In addition, the first predetermined time interval is preferably significantly longer than the second predetermined time interval. For example, the first predetermined time interval may be at least 5 times longer, at least 10 times longer, at least 20 times longer, or at least 30 times longer than the second predetermined time interval. In some data described herein, for example, the occlusion time interval is 5 minutes while the contracted time interval is 10 seconds. In some embodiments, controller 33 is programmed to cause flow limiting element 32 to fully occlude the SVC during the first predetermined time intervals. Controller 33 may be programmed to cause flow limiting element 32 to transition from the occlusion state for the first predetermined time interval to the contracted state for the second predetermined time interval for many cycles throughout the course of a treatment. As further described herein, controller 33 may be programmed to cause flow limiting element 32 to adjust the timing of the first predetermined time interval (e.g., to a third predetermined time interval) and/or to adjust timing of the second predetermined time interval (e.g., to a fourth predetermined time interval) automatically (e.g., responsive to parameters sensed by a sensor(s)) and/or responsive to user input. As will be understood by one skilled in the art, further adjustments to the time intervals may be made throughout the course of the treatment.

Figure 48:
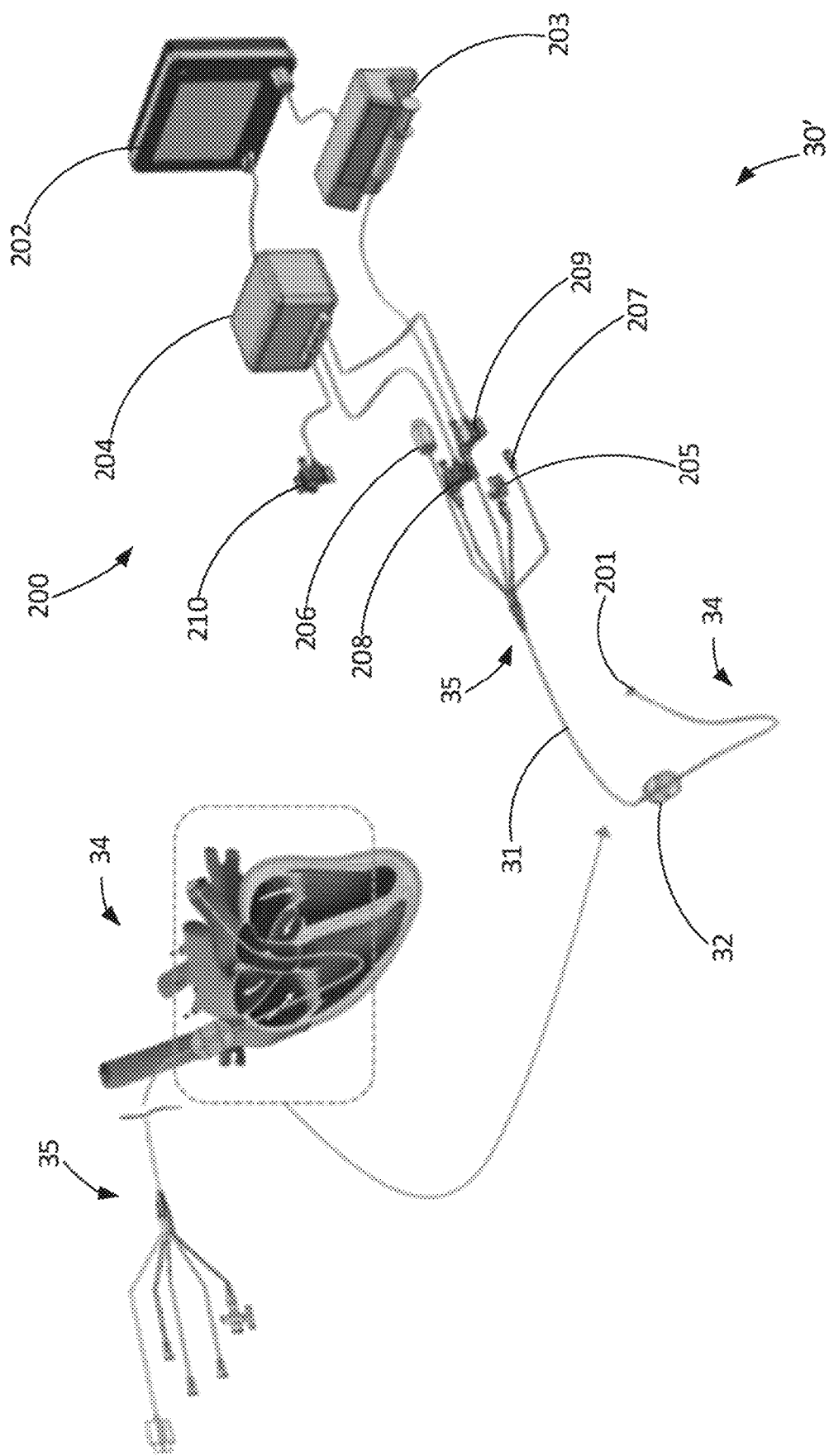
FIG. 48 is an alternative exemplary system constructed in accordance with the principles of the present invention.

Referring now to FIG. 48, an alternative exemplary system 30' of the present invention is described. System 30' is similar to system 30, and includes catheter 31 having flow limiting element 32 disposed on distal portion 34. System 30' differs from system 30 in that catheter 31 is removably coupled at proximal end 35 to external controller system 200. For example, catheter 31 may be decoupled from controller 33 and coupled to external controller system 200 during a hospital visit so the clinician may monitor and adjust operation of flow limiting element 32 directly. Catheter 31 may include optional distal flotation balloon 201 disposed on distal portion 34, distal to flow limiting element 32. As shown in FIG. 48, distal flotation balloon 201 may be positioned within the pulmonary artery of the patient.

External controller system 200 includes display 202, e.g., graphical user interface, electrically coupled to inflation source 203 and external controller 204. Display 202 communicates with inflation source 203 and external controller 204 to display information, e.g. vital physiologic or system parameters, regarding functioning of system 30' for review or adjustment by the clinician, or an alert generated by external controller 204. The clinician may review the data displayed on display 202 to address a malfunction or to adjust the system parameters via the graphical user interface.

Inflation source 203 includes a drive mechanism, e.g., motor, pump, for actuating flow limiting element 32. Inflation source 203 further includes a source of inflation medium, e.g., gas or fluid, such that the drive mechanism may transfer the inflation medium between inflation source 203 and flow limiting element 32 via flow limiting element connector 209 responsive to commands from external controller 204. In addition, catheter 31, when partially external, provides a fail-safe design, in that flow limiting element 32 only can be inflated to provide occlusion when the proximal end of catheter 31 is coupled to external controller 204. Such a quick-disconnect coupling at proximal end 35 permits the catheter to be rapidly disconnected from external controller 204 for cleaning and/or emergency.

External controller 204 includes a processor programmed to control signals to the drive mechanism of inflation source 203, and memory for storing instructions thereon. External controller 204 also includes a power supply, e.g., battery that provides the power needed to operate the processor, inflation source 203, and display 202. Alternatively, external controller 204 may receive power via an electric cord plugged into a source of electric energy, e.g., an electric outlet.

Catheter 31 may be coupled at proximal end 35 to distal flotation balloon connector 205 for fluid communication with a source of inflation medium, e.g., gas or fluid, such that an inflation medium may be transferred between the source of inflation medium and distal flotation balloon 201 responsive to commands from external controller 204, to thereby anchor distal flotation balloon 201 within the pulmonary artery of the patient. Catheter 31 also may be coupled at proximal end 35 to thermistor connector 206 for communication with a cardiac output (CO) monitor for measuring and monitoring temperature, and to pulmonary artery pressure connector 207 for communication with the CO monitor for measuring and monitoring pulmonary artery pressure.

External controller 204 may be coupled to catheter 31 at proximal end 35 via right atrial pressure connector 208 for measuring and monitoring right atrial pressure. External controller 204 also may be coupled to catheter 31 at proximal end 35 via flow limiting element connector 209 for measuring and monitoring the amount of inflation medium transferred between inflation source 203 and flow limiting element 32, e.g., the pressure within flow limiting element 32. External controller 204 also may be coupled to jugular vein pressure connector 210 for measuring and monitoring jugular vein pressure coming from a sheath sideport.

The processor of external controller 204 may include a data transfer circuit as described above that monitors an input from an external sensor, e.g., positioned on catheter 31, and provides that signal to the processor. The processor is programmed to receive the input from the data transfer circuit and adjust the interval during which flow limiting element 32 is maintained in the expanded state, or to adjust the degree of occlusion caused by flow limiting element 32. Thus, for example, catheter 31 may have one or more optional sensors positioned within distal portion 34 of the catheter to measure parameters, e.g., heart rate, blood flow rate, blood volume, pressure including cardiac filling pressure and central venous pressure. The output of the sensors is relayed to the data transfer circuit of external controller 204, which may pre-process the input signal, e.g., decimate and digitize the output of the sensors, before it is supplied to the processor. The signal provided to the processor allows for assessment of the effectiveness of flow limiting element 32, e.g., by showing reduced venous pressure during occlusion and during patency, and may be used by the clinician to determine how much occlusion is required to regulate venous blood return based on the severity of congestion in the patient. As will be understood by one or ordinary skill in the art, system 30' may employ any combination of flow limiting elements and sensors as described above.

Figure 49:
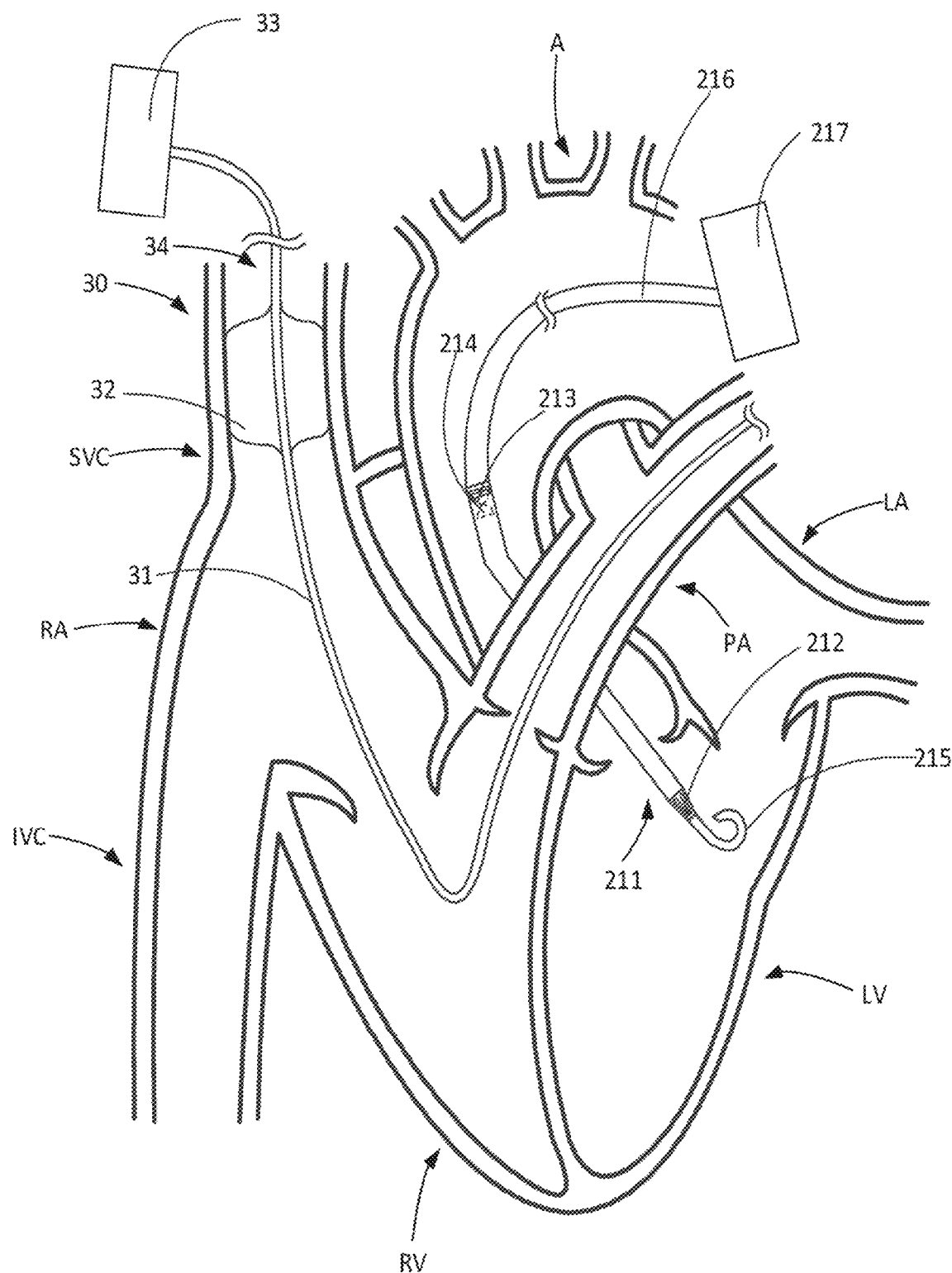
FIG. 49 illustrates an SVC occlusion system in combination with a trans-valvular LVAD.

Referring now to FIG. 49 an SVC occlusion system in combination with a trans-valvular LVAD is described. For example, SVC occlusion system 30 having flow limiting element 32 at distal portion 34 of catheter 31 may be positioned within the SVC, as described above, to at least partially occlude the SVC intermittently, and LVAD system 211 may be positioned in the left side of the heart, offering full hemodynamic support. In one example, LVAD system 211 is an Impella CP® heart pump available from Abiomed® of Danvers, Massachusetts. LVAD system 211 illustratively includes inflow end 212, outflow end 213, impeller pump 214, and anchor 215, disposed on a distal portion of catheter 216. For example, anchor 215 may be a pigtail anchor. During operation, inflow end 212 is positioned in the left ventricle and outflow end 213 is positioned in the ascending aorta. As impeller pump 214 is actuated, blood within the left ventricle is pumped through inflow end 212 and expelled into the aorta via outflow end 213, thereby mimicking the natural pathway of blood flow, unloading the left ventricle, and increasing coronary and systemic perfusion. For example, impeller pump 214 may deliver up to 5.0 L/min of forward blood flow from the left ventricle to the aorta. As will be understood by one having ordinary skill in the art, any suitable pump may be used.

In addition, LVAD system 211 includes controller 217 configured to be operatively coupled to catheter 216 to actuate pump 214 to pump blood from the left ventricle to the aorta, thereby unloading the left ventricle and increasing coronary and systemic perfusion. Controller 217 and controller 33 may be the same and/or incorporated into the same housing unit, such that a single controller is operatively coupled to flow limiting element 32 and pump 214. Controller 33 may actuate flow limiting element 32 to at least partially occlude the SVC simultaneously as controller 217 actuates pump 214 to pump blood from the left ventricle to the aorta.

Figure 50:
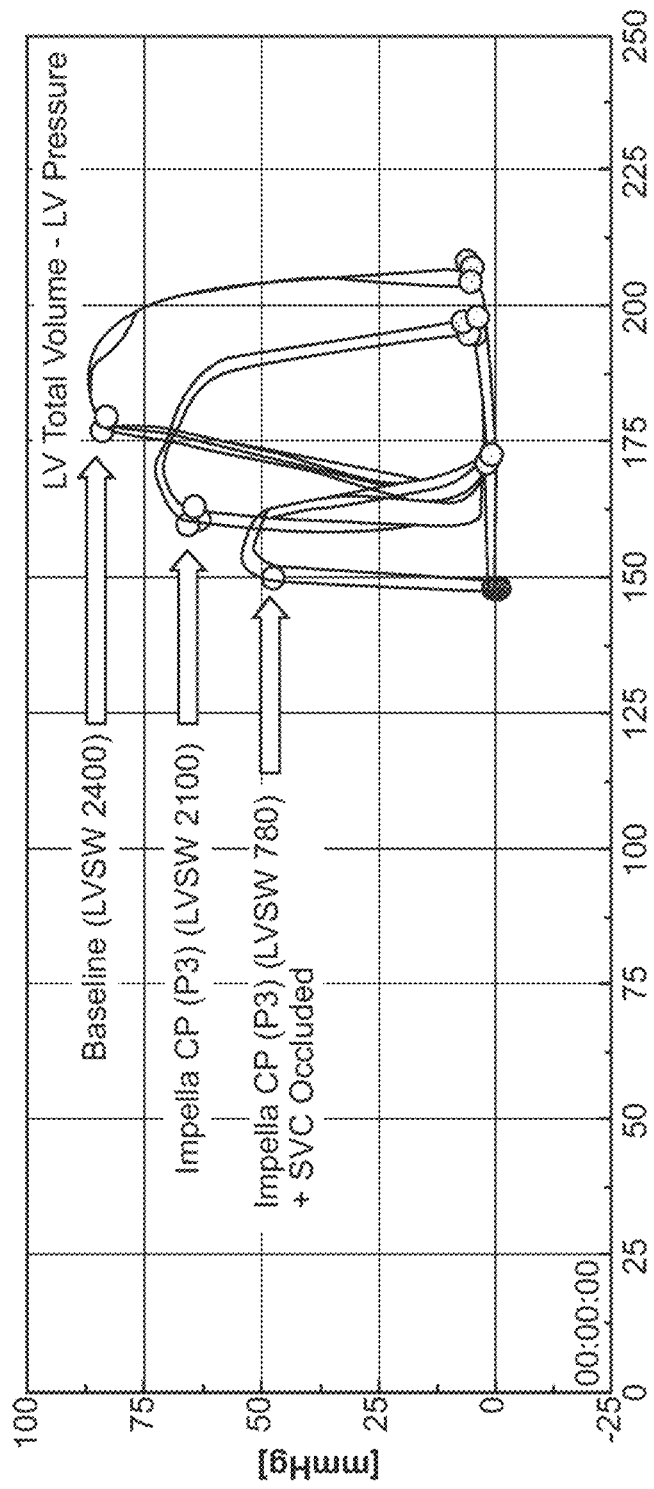
FIG. 50 is a graph illustrating enhancement of the unloading capacity of SVC occlusion when used in combination with a trans-valvular LVAD.

FIG. 50 presents results obtained in an animal model, which demonstrates left ventricular ("LV") total volume-LV pressure for (1) a baseline model; (2) an LVAD model; and (3) an LVAD+SVC occlusion system model. As is evident from comparing model (3) to models (1) and (2), a reduction in cardiac preload ("CP") and left ventricular wall tension ("LVWT") results from use of a SVC occlusion system as described herein in combination with a trans-valvular LVAD (Impella CP® heart pump available from Abiomed® of Danvers, Massachusetts), showing improved functionality and efficiency in pre-load reduction caused by the LVAD. In addition, the trans-valvular LVAD may be operated at a lower rate of pumping while achieving sufficient systemic cardiovascular support, thus reducing the potential for adverse events related to the LVAD.

Figure 51:
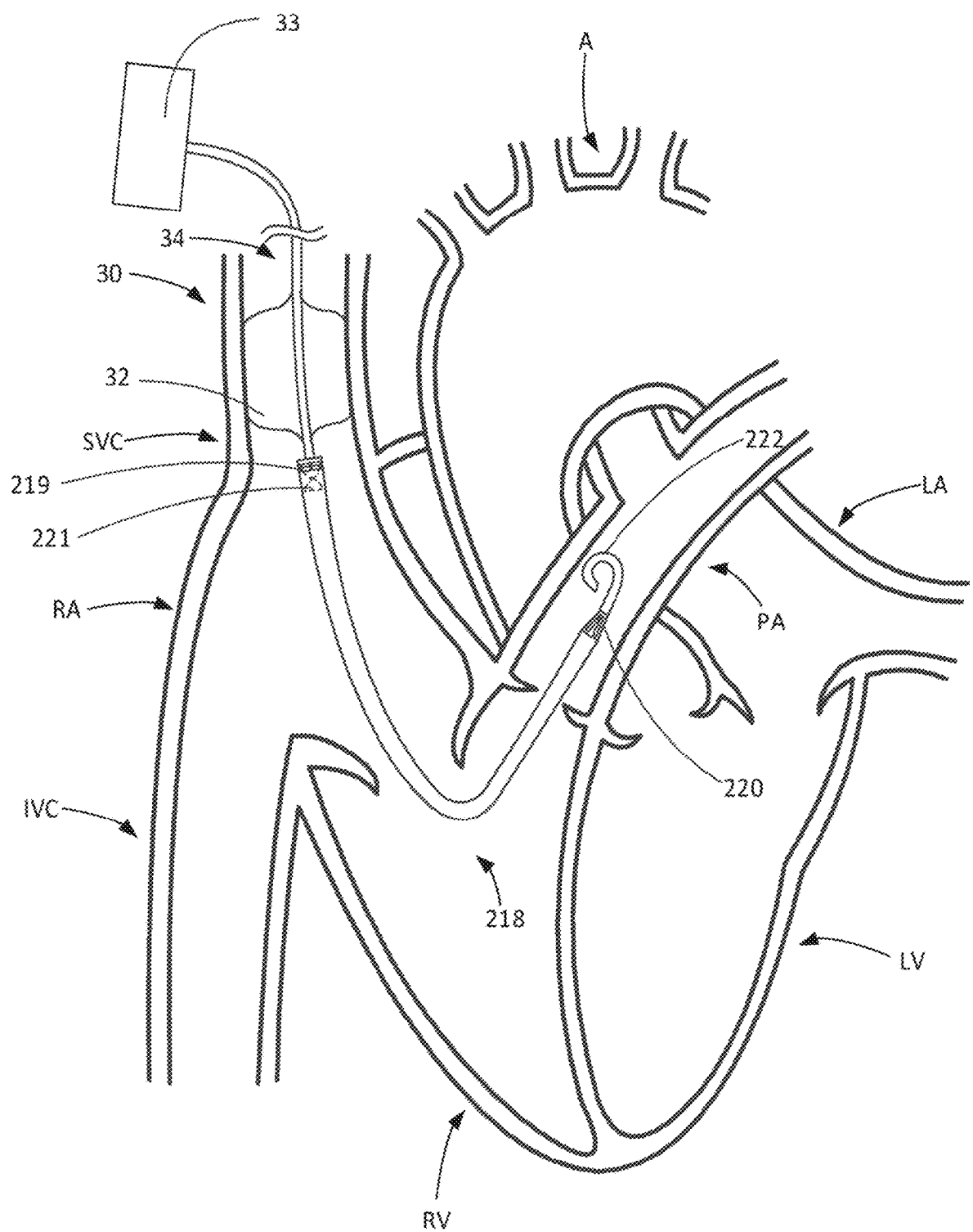
FIG. 51 illustrates an SVC occlusion system in combination with a trans-valvular RVAD.

Referring now to FIG. 51 an SVC occlusion system in combination with a trans-valvular RVAD is described. For example, SVC occlusion system 30 having flow limiting element 32 at distal portion 34 of catheter 31 may be positioned within the SVC, as described above, to at least partially occlude the SVC intermittently, and RVAD system 218 may be positioned distal to flow limiting element 32 on catheter 31, offering full hemodynamic support. In one example, RVAD system 218 is an Impella RPR heart pump available from Abiomed® of Danvers, Massachusetts. RVAD system 218 illustratively includes inflow end 219, outflow end 220, impeller pump 221, and anchor 222, disposed on a distal portion of catheter 223. For example, anchor 222 may be a pigtail anchor. During operation, outflow end 220 is positioned in the pulmonary artery and inflow end 219 is positioned in the SVC, distal to flow limiting element 32. As impeller pump 221 is actuated, blood within the SVC is pumped through inflow end 219 and expelled into the pulmonary artery via outflow end 220, thereby mimicking the natural pathway of blood flow and unloading the right ventricle. For example, impeller pump 221 may deliver up to 5.0 L/min of forward blood flow from the SVC to the pulmonary artery. As will be understood by one having ordinary skill in the art, any suitable pump may be used.

In addition, controller 33 may be configured to be operatively coupled to RVAD system 218 to actuate pump 221 to pump blood from the SVC to the pulmonary artery, thereby unloading the right ventricle. Thus, controller 33 may simultaneously actuate flow limiting element 32 to at least partially occlude the SVC and pump 221 to pump blood from the SVC to the pulmonary artery.

Figure 52:
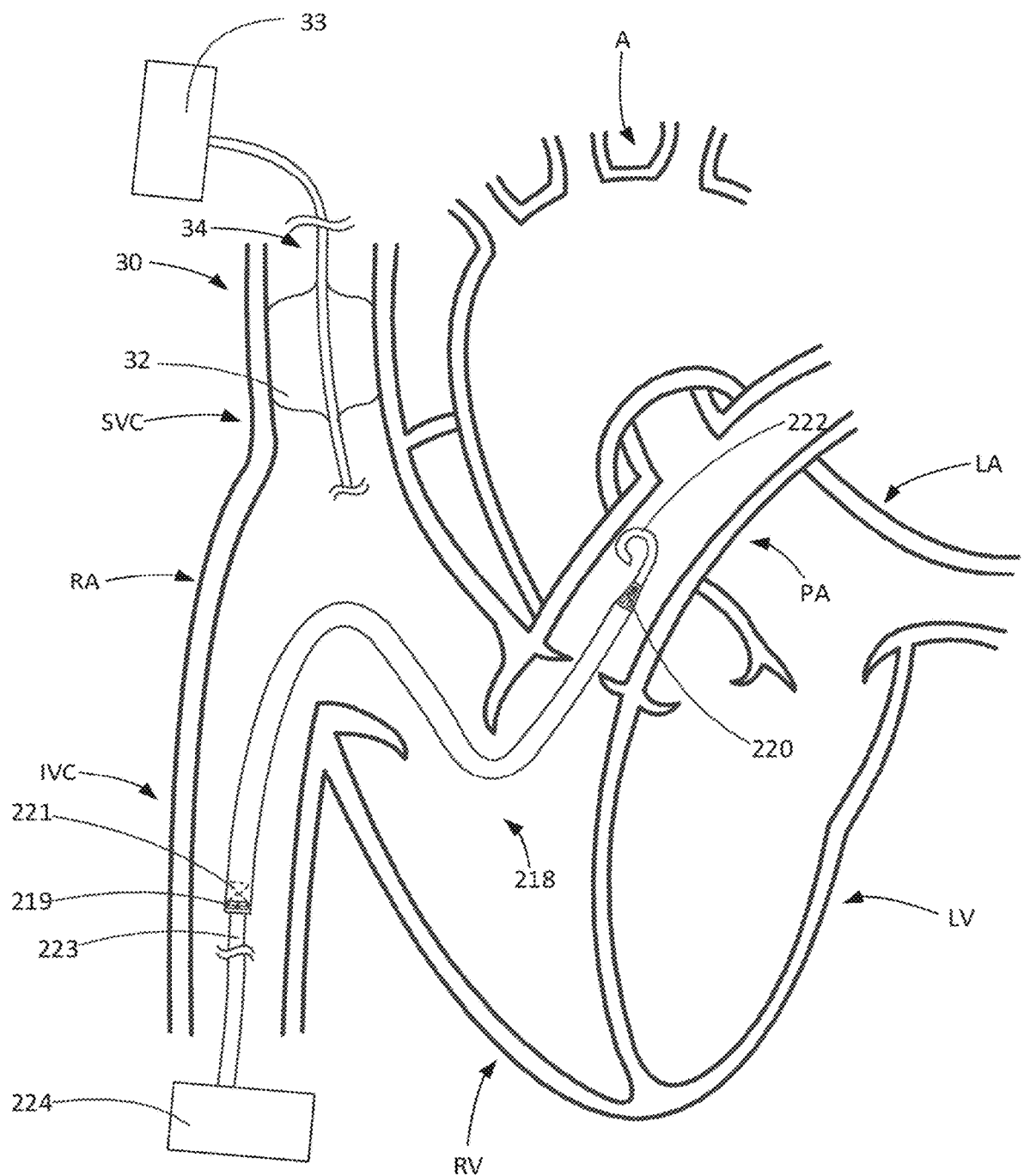
FIG. 52 illustrates an SVC occlusion system in combination with an alternative trans-valvular RVAD.

Referring now to FIG. 52 an SVC occlusion system in combination with an alternative trans-valvular RVAD is described. For example, SVC occlusion system 30 having flow limiting element 32 at distal portion 34 of catheter 31 may be positioned within the SVC, as described above, to at least partially occlude the SVC intermittently, and RVAD system 218 may be positioned in the right side of the heart, offering full hemodynamic support. In one example, RVAD system 218 is an Impella CP® heart pump available from Abiomed® of Danvers, Massachusetts. RVAD system 218 illustratively includes inflow end 219, outflow end 220, impeller pump 221, and anchor 222, disposed on a distal portion of catheter 223. For example, anchor 222 may be a pigtail anchor. During operation, inflow end 219 is positioned in the inferior vena cava (IVC) and outflow end 220 is positioned in the pulmonary artery. As impeller pump 221 is actuated, blood within the IVC is pumped through inflow end 219 and expelled into the pulmonary artery via outflow end 220, thereby mimicking the natural pathway of blood flow, unloading the right ventricle. For example, impeller pump 221 may deliver up to 5.0 L/min of forward blood flow from the IVC to the pulmonary artery. As will be understood by one having ordinary skill in the art, any suitable pump may be used.

In addition, RVAD system 218 includes controller 224 configured to be operatively coupled to catheter 223 to actuate pump 221 to pump blood from the IVC to the pulmonary artery, thereby unloading the right ventricle. Controller 224 and controller 33 may be the same and/or incorporated into the same housing unit, such that a single controller is operatively coupled to flow limiting element 32 and pump 221. Controller 33 may actuate flow limiting element 32 to at least partially occlude the SVC simultaneously as controller 224 actuates pump 221 to pump blood from the IVC to the pulmonary artery.

Figure 53:
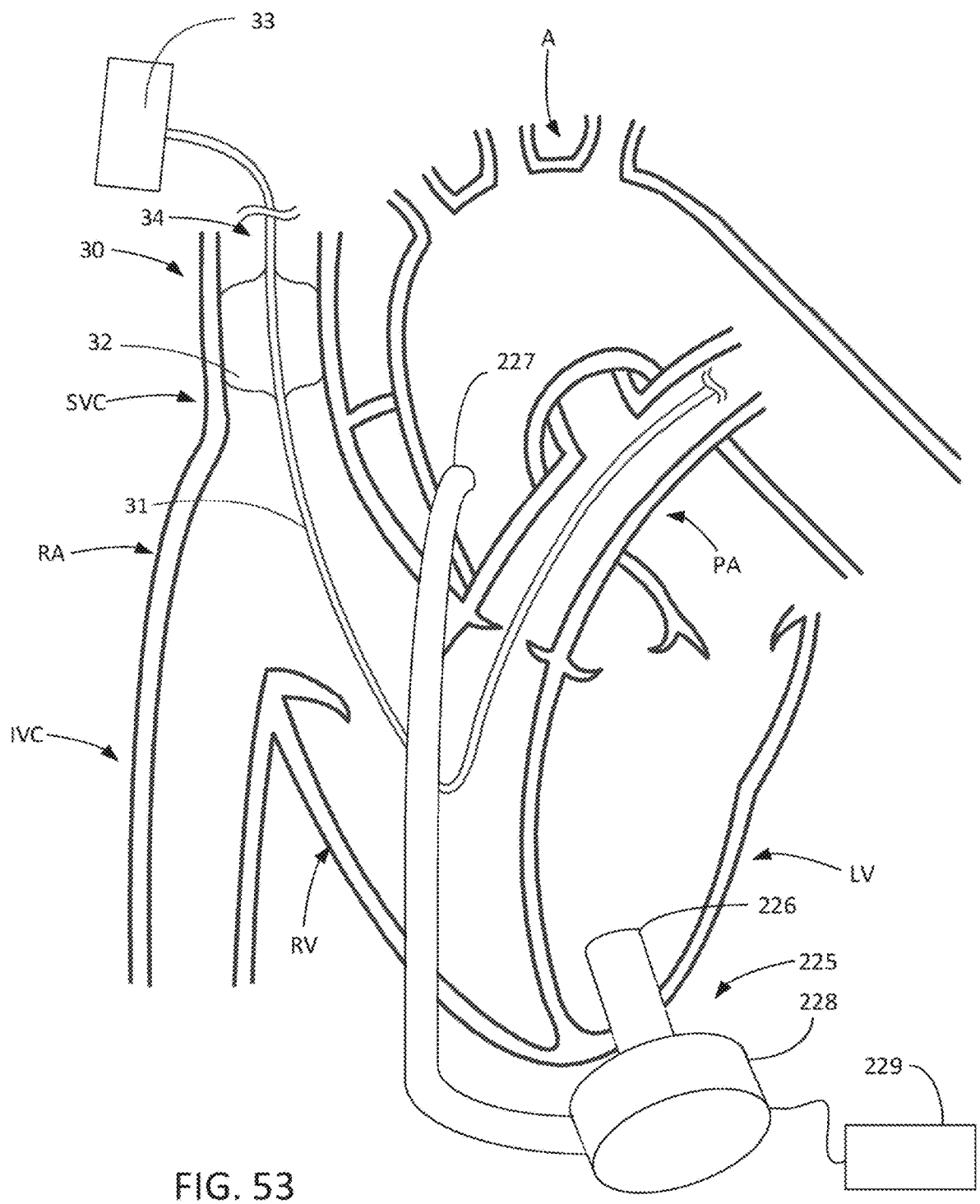
FIG. 53 illustrates an SVC occlusion system in combination with an LVAD.

Referring now to FIG. 53 an SVC occlusion system in combination with a transapical LVAD is described. For example, SVC occlusion system 30 having flow limiting element 32 at distal portion 34 of catheter 31 may be positioned within the SVC, as described above, to at least partially occlude the SVC intermittently, and LVAD system 225 may be positioned transapically in the left side of the heart, offering full hemodynamic support. In one example, LVAD system 225 is an HeartWare™ HVAD™ System available from HeartWare, Inc. of Miami Lakes, Florida. LVAD system 225 illustratively includes inflow end 226, outflow end 227, and pump 228, implanted near the apex of the left ventricle. During operation, inflow end 226 is positioned in the left ventricle and outflow end 227 is positioned in the ascending aorta. As pump 228 is actuated, blood within the left ventricle is pumped through inflow end 226 and expelled into the aorta via outflow end 227, thereby mimicking the natural pathway of blood flow, unloading the left ventricle, and increasing coronary and systemic perfusion. As will be understood by one having ordinary skill in the art, any suitable pump may be used.

In addition, LVAD system 225 includes controller 229 configured to be operatively coupled to pump 228 to actuate pump 228 to pump blood from the left ventricle to the aorta. Controller 229 and controller 33 may be the same and/or incorporated into the same housing unit, such that a single controller is operatively coupled to flow limiting element 32 and pump 228. Controller 33 may actuate flow limiting element 32 to at least partially occlude the SVC as controller 229 simultaneously actuates pump 228 to pump blood from the left ventricle to the aorta.

Figure 54:
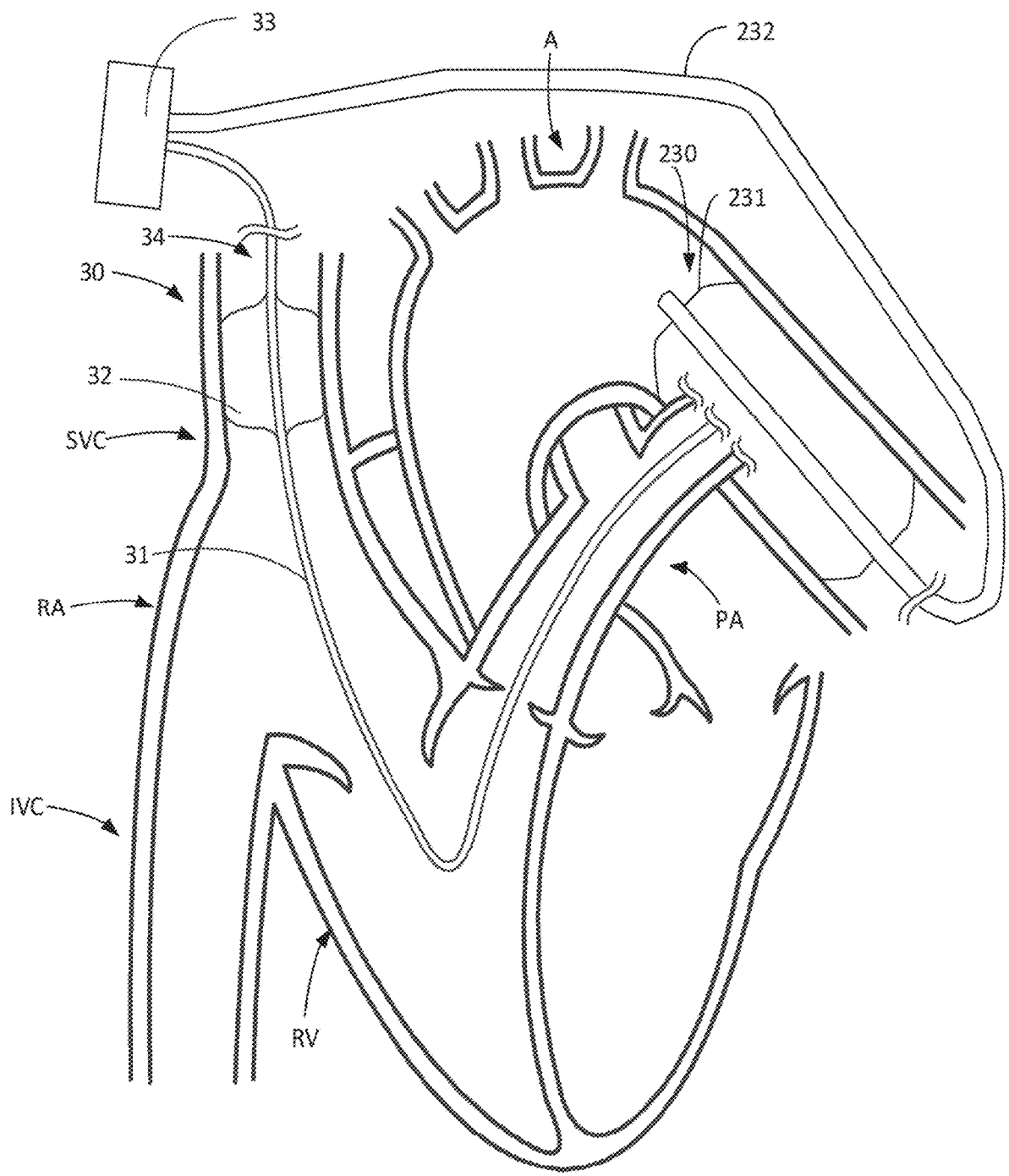
FIG. 54 illustrates an SVC occlusion system in combination with an intra-aortic balloon pump (IABP).

Referring now to FIG. 54 an SVC occlusion system in combination with an intra-aortic balloon pump (IABP) is described. For example, SVC occlusion system 30 having flow limiting element 32 at distal portion 34 of catheter 31 may be positioned within the SVC, as described above, to at least partially occlude the SVC intermittently, and IABP 230 may be positioned the descending aorta. IABP may include flow limiting element 231 and catheter 232 coupled to flow limiting element 231. Flow limiting element 231 illustratively comprises a balloon capable of transitioning between a contracted state, allowing transluminal placement, and an expanded, deployed state. Flow limiting element 231 is preferably sized and shaped so that it partially or fully occludes flow in the aorta in the expanded state. Catheter 232 may be coupled to controller 33 at a proximal end. Controller 33, houses drive mechanism 36 for independently actuating flow limiting element 32 and flow limiting element 231. As shown in FIG. 54, flow limiting element 231 and flow limiting element 32 may be coupled to the same controller such that a single controller is operatively coupled to flow limiting element 32, flow limiting element 231, and pump 221. However, it is understood that flow limiting element 32 and flow limiting element 231 may be coupled to different controllers and/or different pumps. During operation, flow limiting element 231 will be positioned within the descending aorta and will intermittently inflate and deflate. Inflation may be timed to coincide with diastole and deflation timed to coincide with systole. As flow limiting element 231 deflates, a suction effect is created in the aorta, facilitating the transfer of blood from the left ventricle to the aorta during systole.

The combination of the SVC occlusion system with a VAD, RVAD or LVAD may reduce the required flow rate of the VAD to achieve the same hemodynamic response in the patient. This would lower the required speed of the pump, thereby reducing the potential complications associated with the higher speed of the pump required to generate higher flow rates. Further, intermittent occlusion of the SVC following implantation of the pump may help unload the right ventricle while the LVAD is being brought up to operational speed.

It is to be understood that the foregoing description is intended to illustrate and not to limit the scope of the invention, which is defined by the scope of the appended claims. Other embodiments are within the scope of the following claims.

What is claimed is:

1. A system for unloading of cardiac preload and afterload, the system comprising:
a cardiac assist device configured to pump blood within a patient to reduce cardiac afterload;
a flow limiting element configured to be positioned at a superior vena cava (SVC) of the patient; and
a controller configured to be coupled to the flow limiting element, the controller configured to cause the flow limiting element to fully occlude the SVC over multiple cardiac cycles to reduce cardiac preload.

2. The system of claim 1, wherein the flow limiting element is disposed on a catheter configured to be intravascularly positioned within the SVC, and
wherein the controller is configured to fully occlude the SVC by expanding the flow limiting element.

3. The system of claim 1, wherein the controller is configured to cause the flow limiting element to expand and contract within the SVC to reduce the cardiac preload.

4. The system of claim 3, wherein the controller is configured to cause the flow limiting element to repeat the expansion and the contraction over a course of a treatment.

5. The system of claim 4, wherein the controller is configured to cause the flow limiting element to expand to fully occlude the SVC for a first predetermined time interval and to contract for a second predetermined time interval over multiple cardiac cycles.

6. The system of claim 5, wherein the first predetermined time interval is at least five times greater than the second predetermined time interval.

7. The system of claim 5, wherein the first predetermined time interval is 5-20 minutes and the second predetermined time interval is 10-100 seconds.

8. The system of claim 1, wherein the controller is configured to cause the flow limiting element to fully occlude the SVC for more than a minute during expansion.

9. The system of claim 1, wherein the cardiac assist device comprises a catheter.

10. The system of claim 9, wherein the cardiac assist device comprises an impeller pump disposed at a distal portion of the catheter.

11. The system of claim 9, wherein the cardiac assist device is a left ventricular assist device (LVAD).

12. The system of claim 1, wherein the cardiac assist device is a percutaneous left ventricular assist device (LVAD).

13. The system of claim 1, wherein the cardiac assist device is an intra-aortic balloon pump (IABP).

14. The system of claim 1, wherein the controller is configured to cause the flow limiting element to fully occlude the SVC to reduce the patient's diastolic volume and improve cardiac performance as measured by at least one of: reduced cardiac filling pressures, increased left ventricular relaxation, increased left ventricular capacitance, increased left ventricular stroke volume, increased lusitropy, reduced left ventricular stiffness or reduced cardiac strain.

15. The system of claim 1, wherein the controller is configured to cause the flow limiting element to fully occlude the SVC to create a negative pressure sink in a right atrium of the patient, accelerating flow from a renal vein, thereby enhancing renal decongestion and promoting blood flow across a kidney of the patient.

16. The system of claim 1, further comprising a sensor for monitoring pressure differential across the flow limiting element in the SVC indicative of an amount or degree of occlusion in the SVC.

17. The system of claim 1, further comprising:
a first pressure sensor disposed proximal to the flow limiting element, the first pressure sensor configured to output a first pressure signal; and
a second pressure sensor disposed distal to the flow limiting element, the second pressure sensor configured to output a second pressure signal,
wherein the controller is configured to determine pressure in the SVC based on the first pressure signal or the second pressure signal or both.

18. The system of claim 1, wherein the cardiac assist device and the flow limiting element utilize coaxial catheters.

19. The system of claim 1, further comprising a sensor configured to generate a signal corresponding to a physiologic parameter indicative of the patient's hemodynamic state,
wherein the controller is configured to permit adjustment of actuation of the flow limiting element responsive to the signal.

20. The system of claim 1, wherein the flow limiting element is a balloon.

21. A system for unloading of cardiac preload and afterload, the system comprising:
a percutaneous heart pump configured to pump blood within a patient to reduce cardiac afterload;
a balloon catheter configured to be positioned within a superior vena cava (SVC) of the patient; and
a controller configured to be coupled to the balloon catheter, the controller configured to cause a balloon of the balloon catheter to expand to fully occlude the SVC over multiple cardiac cycles to reduce cardiac preload.

22. The system of claim 21, wherein the controller is configured to cause the balloon to expand and contract within the SVC over a course of a treatment to reduce the cardiac preload.

23. The system of claim 22, wherein the controller is configured to cause the balloon to expand to fully occlude the SVC for a first predetermined time interval and to contract for a second predetermined time interval over multiple cardiac cycles.

24. The system of claim 23, wherein the first predetermined time interval is at least five times greater than the second predetermined time interval.

25. The system of claim 24, wherein the first predetermined time interval is 5-20 minutes and the second predetermined time interval is 10-100 seconds.

* * * * *